(12) United States Patent
Xie et al.

(10) Patent No.: US 11,428,638 B2
(45) Date of Patent: Aug. 30, 2022

(54) SPECTROSCOPIC BIOLOGICAL MATERIAL CHARACTERIZATION

(71) Applicant: THE REGENTS OF THE UNIVERSITY OF CALIFORNIA, Oakland, CA (US)

(72) Inventors: Ya-Hong Xie, Dana Point, CA (US); Owen Liang, West Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 108 days.

(21) Appl. No.: 16/961,675

(22) PCT Filed: Jan. 11, 2019

(86) PCT No.: PCT/US2019/013355
§ 371 (c)(1),
(2) Date: Jul. 11, 2020

(87) PCT Pub. No.: WO2019/140305
PCT Pub. Date: Jul. 18, 2019

(65) Prior Publication Data
US 2021/0372933 A1  Dec. 2, 2021

Related U.S. Application Data

(60) Provisional application No. 62/616,808, filed on Jan. 12, 2018, provisional application No. 62/619,610, (Continued)

(51) Int. Cl.
*G01N 33/574* (2006.01)
*G01N 21/65* (2006.01)
(Continued)

(52) U.S. Cl.
CPC .......... *G01N 21/658* (2013.01); *G01J 3/0275* (2013.01); *G01J 3/4412* (2013.01);
(Continued)

(58) Field of Classification Search
CPC ............. G01J 3/0275; G01N 33/56911; G01N 33/574; G01N 2021/3595
See application file for complete search history.

(56) References Cited

U.S. PATENT DOCUMENTS

| 2004/0044481 A1 | 3/2004 | Halpern |
| 2004/0177804 A1 | 9/2004 | Finkelstein et al. |

(Continued)

FOREIGN PATENT DOCUMENTS

| WO | WO-2014129970 A1 * | 8/2014 | ........... A61B 5/0075 |
| WO | WO-2016135194 A1 * | 9/2016 | ................ G01J 3/44 |

(Continued)

OTHER PUBLICATIONS

De Luca, "Raman Spectroscopy for Biomedical Applications: From Label-free Cancer Cell Sorting to Imaging", Jun. 20, 2019 (Year: 2019).*

(Continued)

*Primary Examiner* — Maurice C Smith
(74) *Attorney, Agent, or Firm* — Vista IP Law Group LLP

(57) ABSTRACT

Systems and methods for characterizing biological specimens, which may involve identifying a cell type or state corresponding to a disease or health condition of a subject. A biological specimen is subjected to electromagnetic radiation for spectroscopic analysis such as Surface Enhanced Raman Spectroscopy (SERS) to determine the relative abundance of proteins or amino acids in the cells, which is used in a comparison to previously stored relative abundance data of a database to automatically identifies at least one of cell type and/or cell state of the cells (or the disease/health state (Continued)

of the subject with the disease state including the possibility of virus infection, or drug susceptibility of a subject to bacteria or fungus). The method may also be employed with biological entities or cellular structures such as exosomes and even protein or nucleic acid fragments to determine disease states or health states of the subject.

24 Claims, 34 Drawing Sheets

Related U.S. Application Data filed on Jan. 19, 2018, provisional application No. 62/649,396, filed on Mar. 28, 2018.

(51) Int. Cl.
    *G01J 3/02*       (2006.01)
    *G01J 3/44*       (2006.01)
    *G01N 33/569*    (2006.01)
    *G01N 33/68*     (2006.01)
    *G01N 21/35*     (2014.01)

(52) U.S. Cl.
    CPC ..... *G01N 33/56911* (2013.01); *G01N 33/574* (2013.01); *G01N 33/6803* (2013.01); *G01N 33/6893* (2013.01); *G01J 3/0264* (2013.01); *G01N 2021/3595* (2013.01)

(56) References Cited

U.S. PATENT DOCUMENTS

| | | | |
|---|---|---|---|
| 2008/0122878 A1 | 5/2008 | Keefe et al. | |
| 2009/0082220 A1* | 3/2009 | Krause | G01N 21/658 506/12 |
| 2012/0219506 A1* | 8/2012 | Moore | C12N 9/1051 424/9.2 |
| 2017/0138845 A1* | 5/2017 | Birarda | G01N 15/1463 |
| 2017/0216425 A1 | 8/2017 | Ahmed et al. | |
| 2017/0283845 A1 | 10/2017 | Holmes et al. | |

FOREIGN PATENT DOCUMENTS

| | | | | |
|---|---|---|---|---|
| WO | WO-2018030785 A1 * | 2/2018 | ........... | G01N 33/543 |
| WO | WO-2018121122 A1 * | 7/2018 | ............. | G01N 21/65 |

OTHER PUBLICATIONS

Chih-Yi Liu, "Plasmonic coupling of silver nanoparticles covered by hydrogen-terminated graphene for surface-enhanced Raman spectroscopy", Aug. 29, 2011 (Year: 2011).*
PCT International Preliminary Report on Patentability (Chapter I of the Patent Cooperation Treaty) for PCT/US2020/036436, Applicant: The Regents of the University of California, Form PCT/ISA/210 and 220, dated Jul. 23, 2020 (16 pages).
PCT International Search Report for PCT/US2019/013355, Applicant: The Regents of the University of California, Form PCT/ISA/210 and 220, dated May 23, 2019 (5pages).
PCT Written Opinion of the International Search Authority for PCT/US2019/013355, Applicant: The Regents of the University of California, Form PCT/ISA/237, dated May 23, 2019 (14pages).
Pu Wang, etal., Giant Optical Response from Graphene_Plasmonic System, ACSNANO, vol. 6, No. 7, 6244-6249 (2012).
Pu Wang, et al., Ultra-Sensitivie Graphen-Plasmonic Hybrid Platform for Label-Free Detection, Adv. Mater. 2013, 25, 4918-4924.
Chrisafis Andreou, et al., Surface-Enghanced Ramanspectroscopy: A New Modality for Cancer Imaging, J Nucl Med. 2015;56:1295-1299, Published online: Jul. 16, 2015.
Holly J. Butler, et al., Using Raman spectroscopy to characterize biological materials, 664, vol. 11, No. 4, 2016, nature protocols.
M.R. Hoonejani, et al., Surface Enhanced Raman Spectroscopy and Microfluidics for Rare Cancer Cell Identification, 18th International Conference on Miniaturized Systems for Chemistry and Life Sciences, Oct. 26-30, 2014, San Antonio, Texas, USA.
I-Hsien Chou, et al., Nanofluidic Biosensing for B-amyloid Detection Using Surface Enhanced Raman Spectroscopy (SERS), Nano Lett. Jun. 2008; 8(6): 1729-1735, doi:10.1021/nl0808132.
Xu Wang, et al., Detection of Ciculating Tumor Cells in Human Peripheral Blood using Suface-Enhanced Raman Scattering Nanoparticles, Cancer Res. Mar. 1, 2011; 71(5): 1526-1532. Doi:10.1158/0008-5472.CAN-10-3069.
Pu Wang, et al., Label-Free SERS Selective Detection of Dopamine and Serotonin Using Graphene-Au Nanopyramid Heterostructure, Anal. Chem. 2015, 87, 10255-10261.
Ming Xia, et al., SERS optical fiber probe with plasmonic end-facet, J. Raman Spectrosc. 2017, 48, 211-216.
Xinke Yu, et al., Surface enhanced Raman spectroscopy distinguishes amyloid B-protein isoforms and conformational states, Protein Science 2018 vol. 27:1427-1438.

* cited by examiner

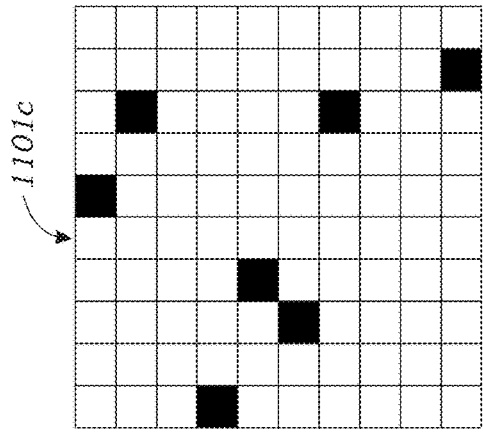
FIG. 11C
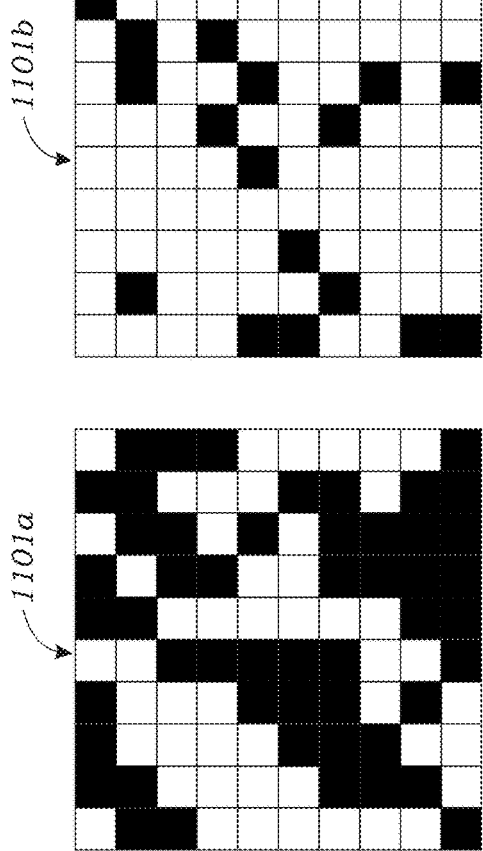
FIG. 11B
FIG. 11A
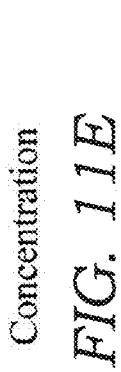
FIG. 11E
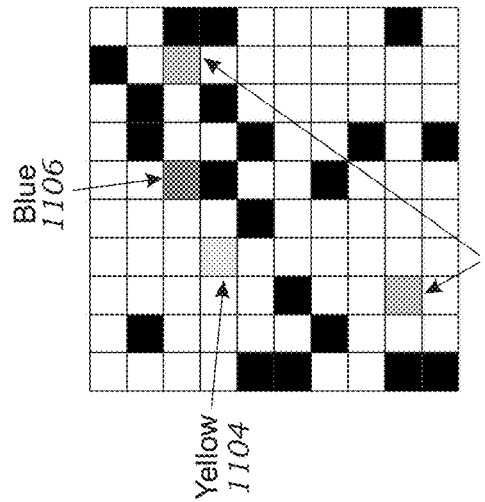
FIG. 11D

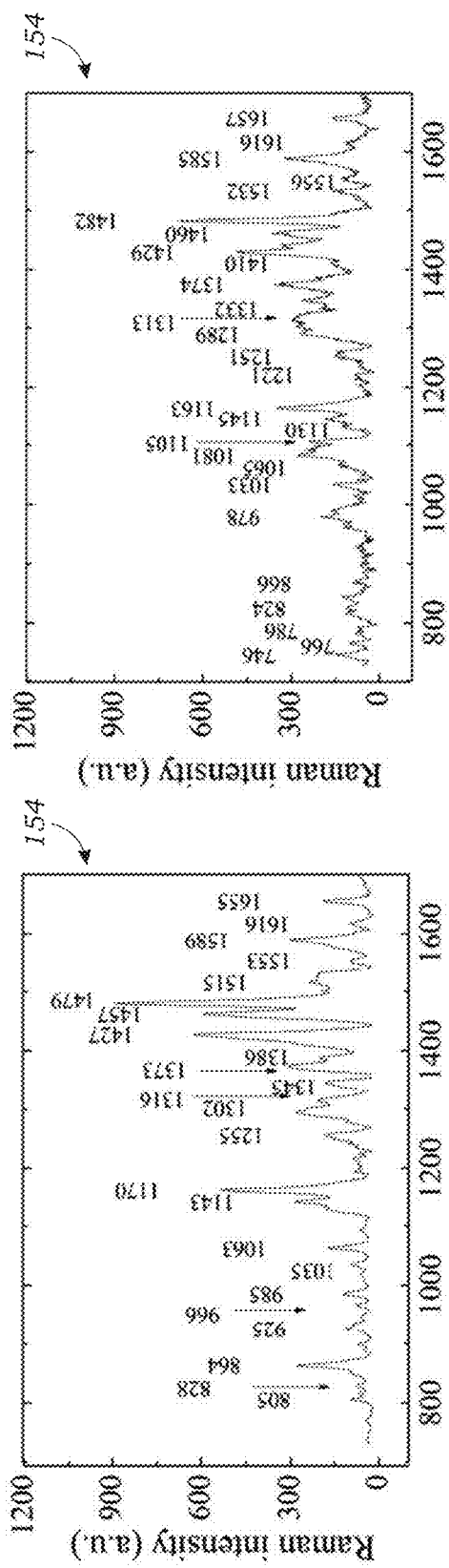
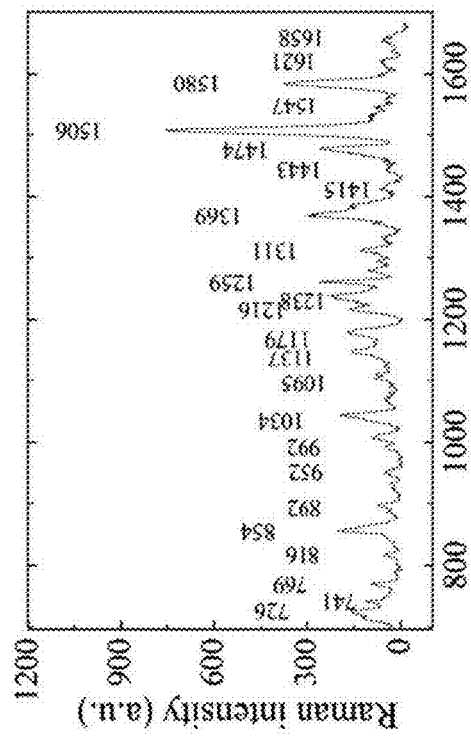
FIG. 13A  FIG. 13B  FIG. 13C  FIG. 13D

SPECTROSCOPIC BIOLOGICAL MATERIAL CHARACTERIZATION

CROSS-REFERENCE TO RELATED APPLICATIONS

This application is a U.S. National Stage filing under 35 U.S.C. § 371 of International Application No. PCT/US2019/013355, filed Jan. 11, 2019, which claims priority to U.S. Provisional Application No. 62/616,808, filed Jan. 12, 2018 and entitled DEVICE AND METHOD OF DETECTING BACTERIA USING SURFACE ENHANCED RAMAN SPECTROSCOPY AND HYBRID PLASMONIC-VAN DER WAALS PLATFORM, U.S. Provisional Application No. 62/619,610, filed Jan. 19, 2018 and entitled METHODS AND SYSTEMS FOR USING BIOMARKERS BASED ON THE MOLECULAR COMPOSITION OF CELLS AND BODILY FLUIDS, and U.S. Provisional Application No. 62/649,396, filed Mar. 28, 2018 and entitled DEVICE AND METHOD FOR LABEL-FREE IDENTIFICATION AND DISCRIMINATION OF CELL-SPECIFIC EXOSOMES, the contents of which are incorporated herein by reference as though set forth in full.

TECHNICAL FIELD

The technical field generally relates to the spectroscopic detection methods, and more particularly, to spectrographic molecular or cellular detection methods for unlabeled biological specimens.

BACKGROUND

Cells are ubiquitous in the biological world. Each cell is a self-contained entity much like a factory that consumes raw material and energy and generates products. Cells are the basic biological building blocks that are used to form higher order structures such as organs in the mammalian body. Some types of cells are considered not an inherent part of the human or mammalian body but are nonetheless extremely important to health and wellbeing. An example of this may include, for example, bacteria that exist inside the gut or digestive system of humans. Other types of cells may be non-native and the source of infection. For example, *Escherichia coli* and *Salmonella enterica* are two examples of prokaryotic bacteria types that are prone to cause infections in humans. There are still other types of cells that are native to the human body but become diseased. An example of this includes cancer cells where normal, healthy cells become cancers.

The basic construction and functionality of cells differ by their types. However, the most common eukaryotic (and some prokaryotic) cells include a cell membrane composed of lipid bi-layers. Inside the membrane are the cellular plasma, a fluid containing proteins, mRNA, ATP, biomolecules, etc., and the cell nucleus which contains DNA. Cell metabolism involves a portion or segment of the DNA being expressive, i.e. producing proteins. The proteins that are produced inside the cell may have any number of final destinations. Some proteins remain in the cell intracellular fluid while other proteins are integrated into the outer cell membrane. Still other proteins may be transported across the cell membrane and deposited into the extra cellular space. The composition and/or the time evolution these proteins are generally known as the cell proteome. The proteins, peptides, amino acids, nucleic acids and their fragments present in bodily fluids due either to normal metabolism or as results of burst cells constitute the basis for biomarkers in addition to those as part of intact cells.

In Raman spectroscopy light from a light source such as a laser is directed to a test surface. Most of the photons that are scattered by the surface have exactly the same wavelength of the incident photos and are known as Rayleigh scatter. Unlike Rayleigh scatter, a small number of photons will scatter and have a slightly shifted wavelength. This effect whereby scatted photons have a shifted wavelength as compared to the incident wavelength is known as the Raman effect or Raman scattering. The shift in wavelength is due to the interaction of the incident photon with the vibrational quanta of the molecule(s) or atoms contained on the surface known as phonons. This shift in wavelength can be monitored to obtain vibrational spectra of the proteome that exists in examined cells.

Traditional Raman spectroscopy is not that useful because of the poor yield of the Raman process. Surface enhanced Raman Spectroscopy (SERS) overcomes this deficiency by incorporating surface plasmon resonance into the Raman process. For example, Wang et al. uses SERS to indirectly measure targeted Circulating Tumor Cells (CTCs) in the presence of White Blood Cells (WBCs). See Wang et al., Detection of Circulating Tumor Cells in Human Peripheral Blood Using Surface-Enhanced Raman Scattering Nanoparticles, Cancer Research, 71(5), March 2011. The method of Wang et al. used SERS nanoparticles with epidermal growth factor peptide as a targeting ligand which bind preferentially to CTCs. As such, the Raman spectra obtained bear the vibrational information of the nano-particles as opposed to that of the biomolecules.

Hoonejani et al. has proposed a somewhat similar platform that uses spectrally rich SERS active biotags that discriminate between health and cancerous cells. Cells that are pre-labeled with SERS biotags were injected into a microfluidic device and the Raman signature of each cell passing through the laser was acquired. See Hoonejani et al., Surface Enhanced Raman Spectroscopy and Microfluidics for Rare Cancer Cell Identification, 18$^{th}$ International Conference on Miniaturized Systems for Chemistry and Life Sciences, October 2014. In both the Wang et al. and Hoonejani et al. platforms, SERS probes are used to identify the CTCs. Both of these platforms rely on labels or bio-tags for the detection specificity. A shortcoming to all bio-tag based detection methods is that the biological label could change due to, for example, cell mutations which are common in cancer cells.

Further, when dealing with bacterial analysis, clinical testing can be time consuming, labor-intensive and costly. Infections caused by bacteria require clinical testing to properly identify and treat the bacterial infection with the appropriate antibiotic drug or spectrum of antibiotic drugs. Current clinical practice is to perform a blood culture whereby a venipuncture is performed and several milliliters (e.g., at least 10 mL) is obtained and injected into pre-prepared blood bottles or the like that contain specific growth media for anaerobic and aerobic organisms. The bottles containing the blood sample are then incubated in a machine at around body temperature. This incubation process is time consuming and can take several days to ensure that proper quantities of bacterium have had a chance to grow and multiply. The blood culture will report if the sample is positive with bacteria present indicating that the patient is bacteremic. If the blood culture is positive, the microbiologist will perform a Gram staining operation on the blood. The Gram staining test is a rapid, general identification of the bacteria that is present. Bacteria are classified as either Gram positive or Gram negative based on the results of the staining. Whether or not the bacteria are stained is used to classify the bacteria into one of two broad classifications (Gram positive or Gram negative) which can be used to generally infer the possible types of bacteria that caused the infection.

Often, in conjunction with the Gram staining process, the blood sample is then subcultured onto agar plates to isolate the bacteria for further culture and susceptibility testing. The culture and sensitivity process identify the species of bacteria and is used to assess antibiotic susceptibility to inform clinicians on the appropriate treatment. Unfortunately, this culture and sensitivity process takes several additional days to perform. There obviously is a long time lag of many days and possibly a week or more between when the blood is drawn from the subject until a final determination is made on the particular species of bacteria that has infected a subject. During this time period, the infection may have significantly progressed in the patient. In some cases, the infection may have spread so rapidly that a patient could die from the infection. Because of this risk, many clinicians may treat a patient with a broad spectrum antibiotic in the hope that antibiotic will be successful against the infection. This, however, poses problems related to the overuse of antibiotics and antibiotic resistance. Over time, bacteria can become unresponsive or immune to antibiotic treatments.

SUMMARY

In one embodiment, a method is described for identifying a disease or health state of a subject, such as a bacterial infection, cancer, Alzheimer's disease and other diseases or health states. A spectroscopy device renders vibrational spectra of the biological specimen reflecting the relative abundance of proteins or amino acids in a biological element of the biological specimen. A computing system, local or remote relative to the spectroscopy device, then executes instructions of programs dedicated to analysis of the spectroscopic data. In certain embodiments, the algorithms are machine learning, neuron network or artificial intelligence. The programs are executed to compare the spectra from an unknown specimen to those of known diseases stored in a database. The method provides for automatic diagnoses and identifications based on spectral feature similarities. This procedure serves as a novel form of biomarker.

For example, Surface Enhanced Raman Spectroscopy (SERS) can be used to develop the library or database that contains cellular proteome signatures. Cell proteome has a one-to-one correlation with their SERS spectroscopy. Highly specific identification of cells and cell metabolic states can be achieved by comparing the Raman spectra of a sample containing cells with a database of all known cell types (or cellular metabolic states), much like the way fingerprints are used to identify criminals.

Thus, in one embodiment, a method is described that characterizes and/or detects a particular biological entity or sample based on the molecular composition of the entity or sample, and in particular, based on the composition of the most abundant proteins (CMAP) in the biological entity or sample. The CMAP proteins (or their respective amino acids which can be used as a proxy of protein composition) is used to characterize and/or detect biological entity or sample. In one embodiment, the method is used to identify cells (eukaryotic or prokaryotic) or organisms of a certain type or the particular state or phenotype in which the cell or organism resides. Each cell type has, for example, its own unique proteome. Related to this, cell proteome can be used as the highly specific identifier of the particular cell type. Furthermore, cells of the same type but that exist at a different "state of health" are also believed to have their unique proteome. For example, healthy cells may have a certain proteome while un-healthy or diseased cells may express a different proteome. In one embodiment, a testing device measures or analyses CMAP and uses this data to determine the state of health of the cell. In another embodiment, the sample involves bodily fluid and the bodily fluid is characterized to diagnose or provide a prognosis for the subject from which the bodily fluid was obtained (e.g., a mammal).

In another embodiment, a method is described for identifying a cell type of a biological specimen. A spectroscopy device of a computerized cell type analysis system subjects a plasmonic substrate containing a biological specimen including one or more unlabeled cells to electromagnetic radiation for spectroscopic analysis. The plasmonic substrate includes plasmonic nanofeatures disposed on a surface of the plasmonic substrate and a van der Waals (vdW) material over the plasmonic nanofeatures such that the biological specimen being analyzed is loaded or deposited atop the vdW material and onto the plasmonic substrate or deposited by flow of a fluid containing the biological specimen. The spectroscopy is employed to collect the vibrational spectra data of the one or more unlabeled cells located on or adjacent to the plasmonic substrate, and a computing system receives the vibrational spectra data that was output by the spectroscopy device. The computing system of the computerized cell type analysis system executes a subject analysis program or system to access a database of previously stored vibrational spectra data, compare collected vibrational spectra data received from the spectroscopy device and the previously stored vibrational spectra data in the database, and automatically identify the cell type of the one or more unlabeled cells in the biological specimen based at least in part upon the comparison.

Thus, in one embodiment, the method is employed that analyzes the CMAP in the cell proteome to differentiate cell types. That is to say, the cell proteome may be analyzed using the systems and platforms described herein and the cell type may be automatically determined by comparing the analyzed proteome with a known library or database that contains proteome data for cells of known types. Alternatively, in another embodiment, the method involves identifying a particular cellular state (e.g., metabolic state) of a given cell type. For example, the proteome may be analyzed to determine whether the cell is healthy or diseased based on the nature of the analyzed proteome. Again, a known library or database that contains proteome data for cells in different metabolic states can be queried to identify the metabolic state of cells in an unknown sample.

In yet another embodiment a method is described for characterizing a health state of a subject. A spectroscopy device subjects a plasmonic substrate to electromagnetic radiation for spectroscopy analysis. The plasmonic substrate includes plasmonic nanofeatures disposed on a surface of the substrate, a vdW material disposed on the plasmonic substrate and over the plasmonic nanofeatures, and a biological specimen of the subject and including one or more unlabeled exosomes is loaded onto the plasmonic substrate, e.g., atop the vdW material. The spectroscopy device collects the resulting vibrational spectra data of the one or more unlabeled exosomes located on or adjacent to the plasmonic substrate, and the vibrational spectra data is provided to a computing system that executes a program to access a database, compare the collected vibrational spectra data against previously stored vibrational spectra data contained in the database, and automatically characterize the health state of the subject based on the comparison.

In a further embodiment, a method is described for identifying a cell type and/or cell state of cells contained in a biological specimen. A spectroscopy device subjects the biological specimen to electromagnetic radiation for spectroscopic analysis to determine data of a relative abundance of proteins, amino acids, or nucleic acid in cells of the biological specimen. This relative abundance data is provided to a computing system, which inputs the relative abundance data into a software analysis program that is executed to access a database, compare the relative abundance data against previously stored relative abundance data contained in the database, and automatically identify at least one of cell type and cell state of the cells in the biological specimen based on a comparison of the determined relative abundance data with the previously stored relative abundance data contained in the database.

In another embodiment, a system is described for identifying a disease or health state in a subject. The system includes a spectroscopy device and a computing system in communication with the spectroscopy device. The spectroscopy device is configured to subject a biological specimen of the subject to electromagnetic radiation for spectroscopic analysis, generate spectroscopic data of the biological specimen, and determine data of a relative abundance of proteins or amino acids in a biological element of the biological specimen. The computing system is also in communication with or includes a computerized database of previously generated vibrational spectra data of label free cells. The computing system is operable to execute a subject analysis program that accesses the database, compares the relative abundance data of the biological specimen against previously stored relative abundance data contained within the database, and automatically identifies a disease or health state of the subject based at least in part upon the comparison.

In a further embodiment, a system for identifying a cell type of a biological specimen includes a spectroscopy device and a computing system in communication with the spectroscopy system and a database of previously stored vibrational spectra data. The spectroscopy device is configured to subject the biological specimen on a plasmonic substrate to electromagnetic radiation for spectroscopic analysis and collect resulting vibrational spectra data of one or more unlabeled cells located on or adjacent to the plasmonic substrate. The biological specimen is deposited onto a plasmonic substrate that includes plasmonic nanofeatures disposed on a surface of the plasmonic substrate. A van der Waals (vdW) material is disposed on the plasmonic substrate and over the plasmonic nanofeatures such that the biological specimen including one or more unlabeled cells is loaded atop the vdW material and onto the plasmonic substrate. The computing system receives the vibrational spectra data from the spectroscopy device, access the database, compares the collected vibrational spectra data and the previously stored vibrational spectra data in the database, and automatically identifies the cell type of the one or more unlabeled cells in the biological specimen based at least in part upon the comparison. System embodiments may also include the computerized database, which may be local or remote relative to the spectroscopy device.

In a further embodiment, a system for characterizing a health state of a subject includes a spectroscopy device and a computing system in communication with the spectroscopy device and a database of previously stored vibrational spectra data. The spectroscopy device is configured to subject a biological specimen on a plasmonic substrate to electromagnetic radiation for spectroscopic analysis and collect resulting vibrational spectra data of the one or more unlabeled exosomes located on or adjacent to the plasmonic substrate, which includes plasmonic nanofeatures disposed on a surface of the plasmonic substrate, and vdW material disposed on the plasmonic substrate and over the plasmonic nanofeatures such that the biological specimen including one or more unlabeled exosomes is loaded onto the plasmonic substrate. The computing system receives the resulting vibrational spectra data from the spectroscopy device, accesses database, compares the collected vibrational spectra data against previously stored vibrational spectra data contained in the database, and automatically identifies the health state of the subject based on the comparison.

In another system embodiment for identifying a cell types or state of cells contained in a biological specimen, a spectroscopy device is configured to subject a biological specimen to electromagnetic information for spectroscopic analysis and determine data of a relative abundance of proteins, amino acids or nucleic acid in cells of the biological specimen, and a computing system in communication with the spectroscopy device and a computerized database of previously stored relative abundance data is configured to receive the relative abundance data from the spectroscopy device, access the database, compare the relative abundance data against previously stored relative abundance data contained in the database, automatically identify at least one of cell type and cell state of the cells in the biological specimen, based on the comparison.

In a further embodiment, a system for characterizing a biological specimen of a subject includes a substrate carrying a biological specimen, a spectroscopy device and a computing system. The substrate is a plasmonic substrate that includes plasmonic nanofeatures disposed on a surface of the plasmonic substrate. A vdW material disposed on the plasmonic substrate and over the plasmonic nanofeatures, and the biological specimen is loaded onto the vdW material and the plasmonic substrate. The spectroscopy device is configured to subject the biological specimen to electromagnetic radiation and collect resulting vibrational spectra data of the biological specimen, which is provided to the computing system, which is also in communication with a computerized database of previously stored vibrational spectra data of known biological specimen components. The computing system compares the received vibrational spectra data of the biological specimen and previously stored vibrational spectra data contained in the database and automatically characterizes the biological specimen based on the comparison.

Embodiments may include different components including, for example, the spectroscopy device and the computing system; the spectroscopy device, the computing system and the database, which may, for example, be generated by multiple different types of spectroscopic analyses; the spectroscopy device, the computing system and the substrate; the spectroscopy device, the computing system the substrate and the database. System embodiments may also include an actuator for biological specimen scanning, which may involve scanning with different pixel sizes and scan areas. Embodiments may also utilize different system configurations in which components and processing are performed locally, or the computing system is remote relative to the spectroscopy device such that data acquisition can be performed in one location, and analysis thereof can be performed in another location.

Embodiments may also involve different substrate/specimen configurations. For example, the vdW material may be graphene, $MoS_2$, $WSe_2$, or hexagonal BN, and the plasmonic substrate may include wells with plasmonic nanofeatures and vDW material, and different wells can be used for different specimens or portions thereof or different component or element concentrations, e.g., different exosome concentrations.

Embodiments may be used for analysis and characterization or identification of different biological specimens and elements or components thereof without the need for specimen labeling. In a single embodiment or multiple embodiments, the biological element that is characterized or identified is a cellular structure such as an exosome, and exosome analysis may involve the spectroscopy device determining data of the relative abundance of proteins or amino acids of a bodily fluid. Different bodily fluids may be analyzed according to embodiments including blood, sweat, urine, cerebrospinal fluid, saliva, semen or pleural fluid. Biological specimens may also be dried or wet specimens and analysis thereof may identify cell types, cell structures, bodily fluid components or health conditions including bacteria, fungus, cancer, a circulating tumor cell, a cell mutation, Alzheimer's disease, an extracellular vesicle (EV) type, or an exosome.

Different spectroscopy devices may be utilized in embodiments including a Raman spectroscopy device, a SERS device, a mass spectrometry device and a Fourier Transform Infrared (FTIR) spectroscopy device.

In a single embodiment or multiple embodiments, the data received from the spectroscopy device, such as relative abundance data, is analyzed by the computing system using multivariate analysis or machine learning analysis.

BRIEF DESCRIPTION OF THE DRAWINGS

FIG. 5B depicts a hybrid plasmonic substrate that includes nanofeatures on the substrate and a vdW material such as graphene, FIG. 5C illustrates a method of how the vibrational spectra of a bacteria is obtained and its spectra is compared with spectra stored in a library or database and matched to determine the species of bacteria, and FIG. 5D illustrates an example of a two dimensional scatter plot of data showing principal components PC1 and PC2 from two different bacteria types;

FIGS. 7A-F depict system and methods for identifying or characterizing cellular elements or structures such as exosomes according to one embodiment, wherein FIG. 7A illustrates a system for identifying exosomes in a biological specimen according to one embodiment, FIG. 7B depicts a hybrid plasmonic substrate that defines a plurality of wells and includes nanofeatures on the substrate and a vdW material, FIG. 7C illustrates a method of how the vibrational spectra of an exosome is obtained and its spectra is compared with spectra stored in a library or database and matched to determine The type of exosome, FIG. 7D illustrates an example of a two dimensional scatter plot of data showing principal components PC1 and PC2 from two different exosome types, FIG. 7E illustrates a schematic representation of a portion of a plasmonic surface undergoing a coarse spectroscopy scan, and FIG. 7F illustrates a schematic representation of a portion of a plasmonic surface undergoing a finer resolution spectroscopy scan;

FIGS. 11A-11C illustrate Raman mapping of the same undiluted (FIG. 11A), 3-times diluted (FIG. 11B), and 10-times diluted (FIG. 11C) exosome preparation, FIG. 11D illustrate a demonstration of the method used to determine the Raman signature of exosomes. The red, yellow and blue pixels represent the presence of 1012, 1509, and 1613 cm−1 peaks, respectively, in the Raman spectrum. The black pixels are pixels in which all three peaks were detected. Only black pixels were considered as containing exosomes, FIG. 11E is a graph showing the comparison of the exosome density obtained through Raman mapping and SEM at three different exosome concentrations.

FIG. 13A illustrates Raman spectra of exosome extracted from serum of healthy individual 1, FIG. 13B illustrates Raman spectra of exosome extracted from serum of healthy individual 2, FIG. 13C illustrates Raman spectra of exosome extracted from lung cancer cell line HCC827, FIG. 13D illustrates Raman spectra of exosome extracted from lung cancer cell line H1975 and FIG. 13E illustrates PCA of exosomes from the different sources shown in FIGS. 13A-13D and the spectrum shown in FIG. 10 demonstrating that they are clearly distinguishable;

FIGS. 19A-19D are averaged Raman spectra of exosomes from four different origins including two healthy individuals (FIG. 19A and FIG. 19B), lung cancer cell line HCC827 (FIG. 19C) and lung cancer cell line H1975 (FIG. 19D)

DETAILED DESCRIPTION OF ILLUSTRATED EMBODIMENTS

Embodiments of the invention provide for intelligent and automated biological specimen characterization or identification of cell types and particular diseases or conditions of a subject or patient while doing so with improved accuracy and efficiency and eliminating the need for human input and judgment. Embodiments provide for these improvements while addressing shortcomings of known systems and methods that rely on biotags or pre-labeled cells and addressing further shortcomings of such known systems and methods since a biological label may change due to, for example, cell mutations which are common in cancer cells since embodiments do not require pre-labeling biological specimens before they are analyzed.

Figure 1:
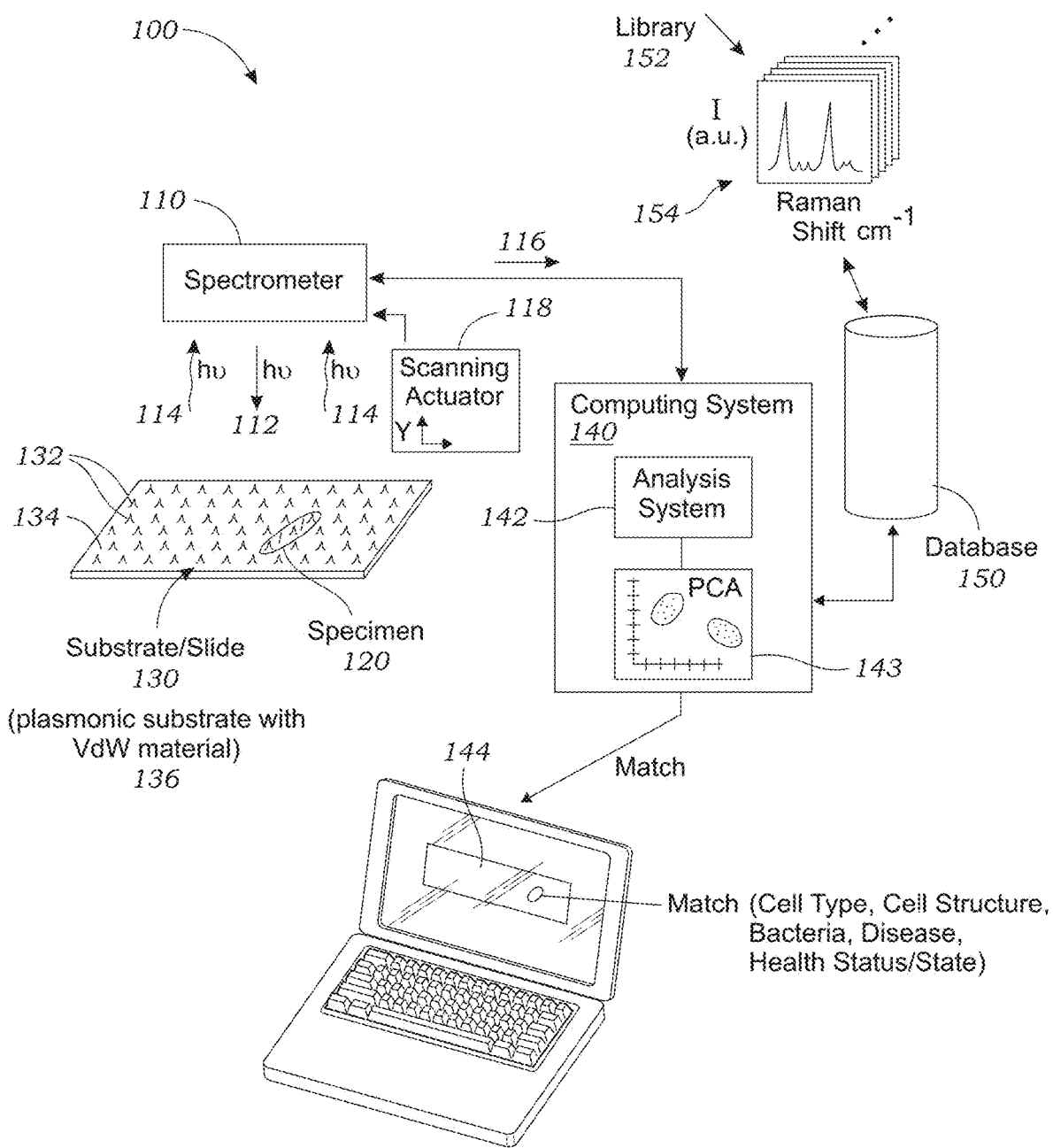
FIG. 1 depicts a system for identifying or characterizing biological specimens according to one embodiment.

With reference to FIG. 1, a biological specimen characterization system 100 (generally, system 100) constructed according to one embodiment includes a spectrometer 110 operable to direct electromagnetic radiation 112 incident upon a biological specimen 120 containing live and/or dead cells carried by a slide or substrate 130, a computing system 140 in communication with spectrometer 110, and a database 150 accessible by computing system 140.

Embodiments may utilize different types of spectrometers 110. Spectrometer 110 may be a Raman spectroscopy device, a Surface Enhanced Raman Spectroscopy (SERS) device, a mass spectroscopy device, a Fourier Transform Infrared (FTIR) spectroscopy device or other spectrometer device. For mass spectrometry, rather than electromagnetic radiation, electrons may be used with the sample to create positively charged ions that are then detected using a detector as is well known in the art. A typical Raman spectrometer 120, for example, includes a laser excitation source and delivery optics. Collection optics are provided that are used to capture the Raman scattered light. A wavelength separation device (e.g., grating) is used to separate the wavelengths of light.

Embodiments may also be utilized to analyze, characterize or identify different types of unlabeled biological specimens 120, which may be a dried specimen (e.g., dried before spectroscopic analysis) or a wet specimen (e.g., contained in a fluid at time of spectroscopic analysis). Examples of biological specimens 120 that can be characterized or identified according to embodiments include, by way of example, a bodily fluid in the form of blood, sweat, urine, cerebrospinal fluid, saliva, semen and pleural fluid. Biological specimen 120 may be dry, semi-solid form, or wet, or in fluid/liquid form, when loaded onto substrate 130. Different biological specimen 120 preparation devices and methods and biological specimen delivery devices and methods 212 may be employed as described in further detail below depending on the type of biological specimen 120 and analysis to be performed. For example, a specimen preparation device in the form of a centrifuge may be used condense biological specimen 120 into a solid or pellet form, which is then subjected to spectroscopic analysis. As another example, biological specimen 120 may be a bodily fluid that is deposited onto substrate 130 by flowing over substrate 110. For ease of explanation, reference is made generally to biological specimen 120, and various embodiments are discussed with reference to specific types of biological specimens 120 and preparation of same.

Substrate 130 may be in the form of a slide, wafer or die obtained from a wafer and be a plasmonic substrate. A substrate 130 (generally, substrate 130) may include plasmonic nanofeatures 132 disposed on a surface 134 of substrate 130, and a van der Waals (vdW) material 136 that is disposed on substrate 130 and over the plasmonic nanofeatures 132 such that biological specimen 120 is loaded onto substrate 130 and over vdW material 136.

For example, substrate 130 may include Si/SiO$_2$ substrate. Plasmonic nanofeatures 132 are typically metallic surfaces that include a nanostructured surface. For example, a metal such as gold (Au), silver (Ag), or copper (Cu) can be deposited onto substrate surface 134 along with periodic or quasi-periodic nanofeatures 132 patterned on substrate surface 134. An example of such nanofeatures 132 includes nanometer-sized pyramids or tips arranged in a hexagonal pattern or other symmetry types that can be created using standard lithographic techniques. Nanopyramids have nearly identical size and topology and support significantly enhanced electromagnetic fields (i.e., they demonstrate plasmonic resonance). In an alternative embodiment, nanopyramids can be arranged into patches of limited size with neighboring patches containing arrays of nanopyramids of different sizes. While nanofeatures 132 in the form of nanopyramids are illustrated in FIG. 1 and other figures, substrate 130 may include nanofeatures 132 of different shapes such as posts, gratings, or even apertures or wells. The vdW material disposed atop substrate 130 may be a family of two-dimensional (2D) materials including graphene, $MoS_2$, $WSe_2$, hexagonal BN, phosphorene. The key characteristic of vdW material 136 is its anisotropic bond strength such that atoms are connected in the 2D plane via covalent bonding (i.e., strong bonds) with out-of-plane bonding being very weak such as through van der Waals bonding. Different substrate 130 configurations may be utilized for processing and analysis of different biological specimens 120.

Computing system 140 executes instructions of analysis program 142 that uses one or more types of statistical analysis algorithms 143 such as one or more of multivariate analysis, clustering algorithms, principal component analysis, neuron networks, machine learning and artificial intelligence algorithms. For ease of explanation, reference is made to an analysis system or analysis program 142. Analysis program 142 generates a new data structure or transforms vibrational spectra data 116 to have a structure suitable for comparison with stored vibrational spectra data or Raman shift library data of database 150. For example, analysis program 142 executes a software routine or executable file for performing an algorithm of multivariate analysis such as principle component analysis (PCA) on the spectra or Composition of Most Abundant Proteins (CMAP) data of biological specimen 120.

PCA is a variable dimension reduction algorithm that uses an orthogonal transformation to convert a set of observations of possibly correlated variables into a set of values of linearly uncorrelated variables called principal components (or sometimes, principal modes of variation). For SERS, as an example, the correlated variables are the vectors including Raman shift and the related Raman intensity each Raman spectrum. This orthogonal transformation is defined so that the first principal component (PC1) had the largest possible variance (i.e., accounted for as much of the variability in the data as possible), and each succeeding component (PC2, PC3, etc.) in turn had the highest variance possible under the constraint that it is orthogonal to the preceding components. PCA analysis may be performed by analysis program 142 executed on computing system 140. Prior to performing PCA analysis, background of the vibrational Raman spectra data 116 may be subtracted.

While PCA analysis is described and illustrated in FIG. 1 and other figures, it should be understood that any different data analysis algorithms 143 may be used. Examples of other multivariate analysis algorithms 143 include hierarchical clustering analysis (HCA), support vector machine (SVM), countless variation of algorithms categorically known as machine learning, etc.

Database 150 includes a vibrational spectra or Raman shift library 152 of known biological specimens or elements or components thereof and their respective vibrational spectra or Raman shift data 154 (generally, vibrational spectra data). For example, database 150 may include vibrational spectra data 154 on different known specimens including different cell types (e.g., WBCs, CTCs, bacteria, yeast cells, fungi, etc.), bodily fluids, or cellular structures (e.g., exosomes), and alternatively, or additionally, database 150 may contain vibrational spectra data 154 of known metabolic of health state of cells of a single type (e.g., metabolic state or cell proteome of healthy cells, un-healthy or diseased cells, or stressed cells).

In one embodiment, database 150 contains CMAP data of known biological specimens and may contain known or "gold standard" data corresponding to cells, exosomes, bodily fluids, or other biological entities having a known identity or state that has been confirmed using different testing or analytical processes. Database 150 may contain CMAP data that has been previously generated one or more different types of spectrometers, such as those noted above. In this manner, different CMAP testing platforms can access the corresponding database that contains the relevant "gold standard" data. The "gold standard" data may be generated in parallel with the spectroscopic data of the same biological specimen. That is to say a biological specimen 120 may be tested on spectrometer 110 (e.g., SERS, conventional Raman spectroscopy, mass spectrometry, FTIR spectroscopy, or other type) while also being characterized or tested with a non-spectroscopic "gold standard" method so that the tested biological specimen 120 is properly characterized (e.g., healthy, diseased, drug-resistant, and the like).

Database 150 may contain vibrational spectra or SERS data 154 on different cell types (e.g., WBCs, CTCs, bacteria, yeast cells, fungi, etc.), bodily fluids, or cellular structures (e.g., exosomes). Alternatively, or in addition to, the database 150 may contain vibrational spectra or SERS data 154 on the known metabolic of health state of cells of a single type. Of course, for other modalities besides SERS, CMAP data produced by the respective platform is stored in the database 150. The data that is stored in database 150 may contain SERS spectra of all known specimens to which the unknown biological specimen 120 may be compared. For example, the metabolic state or cell proteome of healthy cells, un-healthy or diseased cells, or stressed cells may be recorded in database 150. The data that is stored in database 150 is used to identify cells of a particular type or identify the cellular state of a particular cell. The data that is stored in database 150 may also be used to characterize the health or disease state of the subject based on results of analysis of biological specimen 120.

It will be understood that database 150 may contain records of thousands or millions of cells (or other cellular entities), bodily fluids, cell types, cellular metabolic states that are known in advance and loaded into database library 152 and updated as needed. For example, database 150 updates may be executed using analysis program 142 as it identifies and/or classifies cells of biological specimen 120 or classifies biological specimen 120 in the form of a bodily fluid. Database 150 may be maintained and sponsored by, for example, a government entity that provides access to the same. Database 150 may also be a commercial or proprietary database 150 whereby users obtain permission to access vibrational spectra data 154 of known specimens.

Spectrometer 110 is positioned relative to substrate 130 so that biological specimen 120 loaded onto substrate 130 is subjected to incident electromagnetic radiation 112 (such as excitation source of laser or infrared radiation depending on the type of spectrometer utilized) emitted by spectrometer 110. Reflected electromagnetic radiation 114 is detected by spectrometer 110, and corresponding vibrational spectra data 116, or wavelength or Raman shift data of biological specimen 120, is based on the interaction of electronic magnetic radiation and biological specimen 120/substrate 130 and generated by spectrometer 110. Vibrational spectra data 116 is communicated to or retrieved by computing system 140.

Computing system 140, by a processor, executes programmed instructions of an analysis system or program 142 to process vibrational spectra data 116 and utilizes one or more statistical analysis algorithms 143 such as multivariate analysis, clustering algorithms, principal component analysis (PCA) and machine learning. The results of the statistical analysis algorithm 143 are used by the analysis program 142 to identify a matching record in library 152, and the matching record is presented to a user through a display 144 of computing system 140 or other computing device. Thus, computing system 140 automatically performs biological specimen 120 characterization or identification, e.g., biological specimen is, or contains, bacteria, cancer, Alzheimer's disease as non-limiting examples, and informs the user of the determined identification or characterization.

Figure 2:
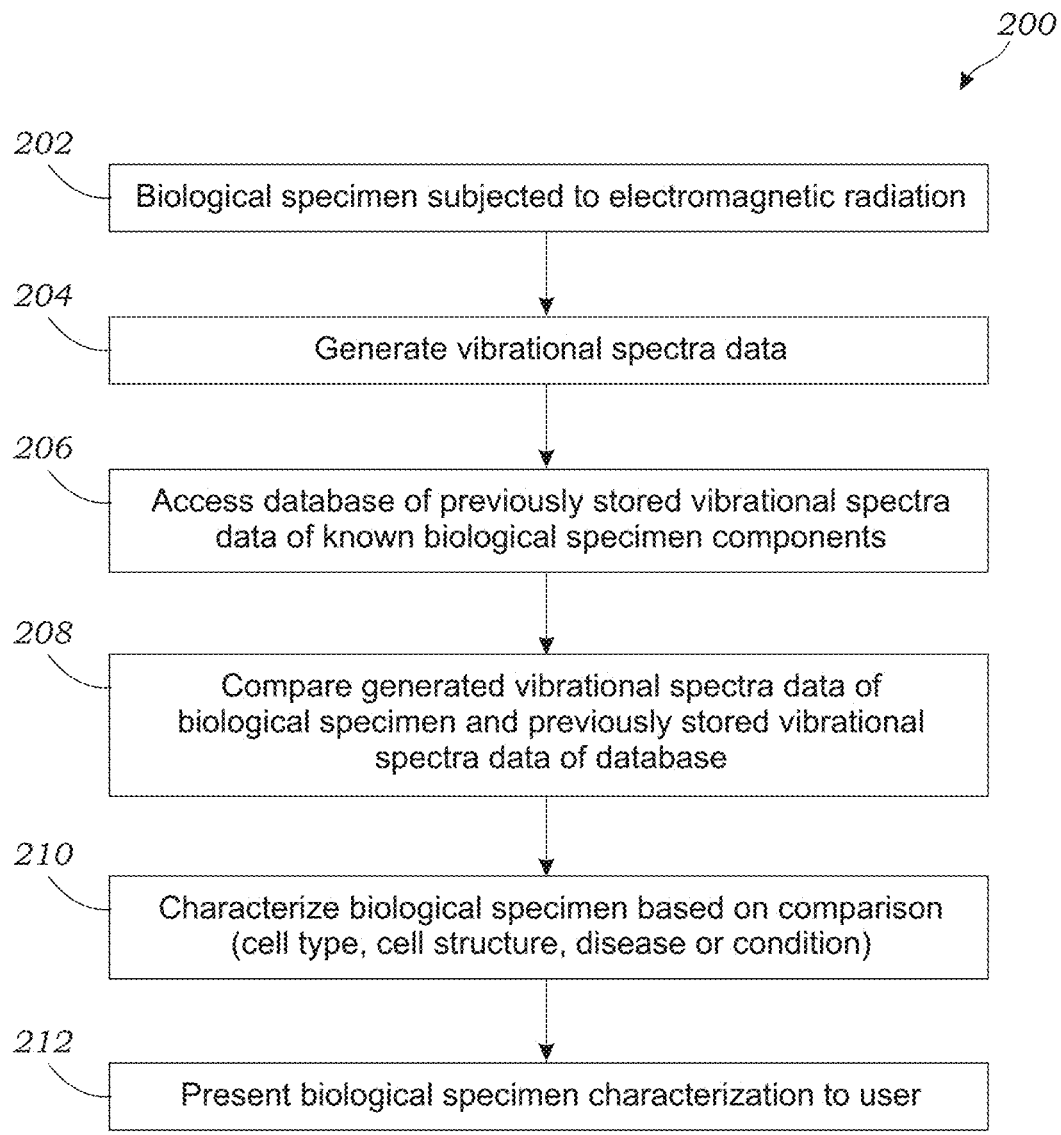
FIG. 2 is a flow diagram of a method for identifying or characterizing biological specimens according to one embodiment.
Figure 3:
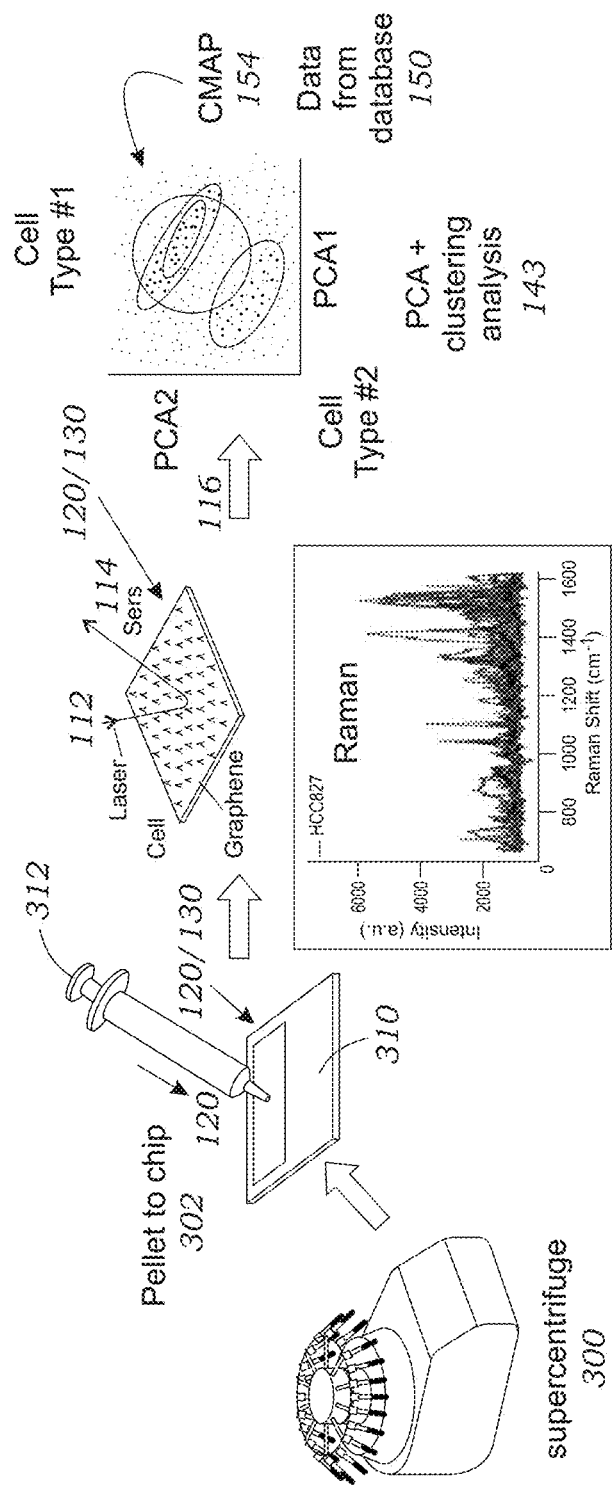
FIG. 3 illustrates a sequence of operations used to preprocess a biological specimen and then subject the biological specimen to spectroscopy, principal component and clustering analysis used to identify or characterize a biological specimen according to one embodiment.

Referring to FIGS. 2 and 3, and with continuing reference to FIG. 1, at 202, biological specimen 120 is provided or prepared 300 and loaded onto substrate 130 that is provided or prepared and supported by a platform 310. Biological specimen 120 may be loaded by being deposited onto substrate 130 or applied via flow of fluid over substrate 130 via specimen delivery device 312 as shown in FIG. 3. At 204, spectrometer 110 is activated to subject biological specimen 120 to electromagnetic radiation, biological specimen 120/substrate 130 is scanned, and resulting vibrational spectra data 116 is generated by spectrometer 110. For example, light source of spectrometer 110 is able to map the surface of the substrate 130 in x and y directions. In this regard, the entire surface of the substrate 130 can be scanned or mapped, and for this purpose, the light source may be coupled to a x and y motion actuator 118, or instead of moving the light source, substrate 130 could be moved in the x and y directions by actuatable platform or stage 210.

More specifically, spectrometer 110 is activated so that biological specimen 120 and substrate 130 are subjected to incident electromagnetic radiation 112 and reflected 114 electromagnetic radiation is detected by optical detector and associated electronics of spectrometer 110 to record light intensity and wavelength changes compared to the excitation source and incident electromagnetic radiation 112. Reflected electromagnetic radiation 114 reflects of vibrations of molecules or groups of molecules and associated energy transitions and wavelength/frequency changes that result from absorption or scattering of the electromagnetic radiation as detected by spectrometer 110.

System 100 includes computing device 140 executing analysis program 142 to analyze the results obtained by spectrometer 110. Spectrometer 110 determines or obtains vibrational spectra data 116 of biological specimen components deposited on substrate 130. Vibrational spectra data 116 that is recorded includes the intensity of Raman scattering as well as the Raman shift which is expressed in wave numbers ($cm^{-1}$). Vibrational spectra data 116 is obtained at a plurality of locations on the surface of the substrate 130. Vibrational spectra data 116 may be associated with a particular x, y location on substrate 130. In one aspect, vibrational spectra data 116 may be associated with particular "hot spots" on hybrid substrate surface where the SERS enhancement is particularly strong. For example, the signal-to-noise ratio of the enhanced SERS signal may be improved at these "hot spots."

For ease of explanation, reference is made to spectrometer 110 emitting radiation or incident radiation 112, detecting reflected radiation 114 and generating corresponding vibrational spectra 116 and/or associated relative abundance data for proteins and/or amino acids of biological specimen 120.

Continuing with reference to FIG. 2, at 206, computing system 140 receives the generated vibrational spectra data 116 from spectrometer 110 and accesses database 150. Computing system 150 may be local relative to spectrometer 110 or remote relative to spectrometer 110 and in communication with spectrometer 110 by a communications network such as a wide area network (WAN) or Internet. Database 150 may also be local relative to computing system 140 or remote relative to computing system 140 and in communication with communication system through a communication network, e.g., if database 150 is a third party or government database.

At 208, computing system 140 processes vibrational spectra data 116 received from spectrometer 110 and compares processed vibrational spectra or Raman shift data 116 with stored vibrational spectra or Raman shift data 154 of database 150 to characterize or identify biological specimen at 210. The characterization or identification may be based on a cell type or type of cell in biological specimen 120, cell structure, disease, condition or health state.

For this purpose, analysis program 142 executed by computing system 140 may utilize different statistical analyses or machine learning such as deep neuron networks (DNN), which serves as a post-analysis technique whereby possible similarities in spectral features of known and unknown biological specimens can be determined. For example, with a biological specimen 120 in the form of a cell structure such as an exosome, spectral features that can be extracted include the peak intensity values at a particular wavelength shifts as well as peak width to height ratios (or other ratios) at particular wavelength shifts. Thus, a statistical analysis technique such as PCA that reduces the variables in a data set by transforming the data into a new coordinate system can be employed to transform data into a first principal component PC1 and a second principal component PC2 that can be used to extract the most obvious distinctions between data sets. Data that cannot be distinguished with a dimensionality reduction algorithm such as PCA may then be subjected to more advanced data analysis algorithms such as DNN.

For example, as generally illustrated in FIGS. 1 and 3, the first principal component PC1 and the second principal component PC2 may be plotted on a new coordinate system whereby each principal component is represented by orthogonal axis. If the test data based on the vibrational spectra data 116 falls within the oval that is representative of bacteria type #1, then the unknown biological specimen 120 can be identified as known specimen type #1. Similarly, if the test data based on the vibrational spectra data 116 falls within the oval that is representative of specimen type #2, then the unknown biological specimen 120 can be identified as specimen type #2. While the description and FIGS. 1 and 3 provide an example of how an analysis program 142 in the form of PCA may be applied and using two principal components PC1 and PC2, it should be understood that additional principal components may be used to identify differences biological specimens, in which case vibrational spectra data 116 would be represented in higher order dimensional plots.

In one aspect of the invention, the software analysis system 28, which is executed on or by the computer 26, includes a software routine or executable file for performing multivariate analysis such as principle component analysis (PCA) on the spectra (or other CMAP data) of the known and unknown cells, biological entities, or sample. Principal component analysis (PCA) is a statistical procedure that uses an orthogonal transformation to convert a set of observations of possibly correlated variables into a set of values of linearly uncorrelated variables called principal components (or sometimes, principal modes of variation). For SERS, the correlated variables are the vectors including Raman shift and the related Raman intensity of each Raman spectrum. This orthogonal transformation is defined so that the first principal component (PC1) had the largest possible variance (i.e., accounted for as much of the variability in the data as possible), and each succeeding component (PC2, PC3, etc.) in turn had the highest variance possible under the constraint that it is orthogonal to the preceding components. PCA analysis may be performed by the software analysis system 28 which is executed on the computer 26. Prior to performing PCA analysis the background of the Raman spectra is background subtracted.

While PCA analysis is described and illustrated in the Figures, it should be understood that any different types of data analysis algorithms may be used. Examples of other data analysis algorithms include hierarchical clustering analysis (HCA), support vector machine (SVM), DNN, countless variation of algorithms categorically known as machine learning, etc. It should be understood that any number of analysis algorithms may be employed to look for proteins, amino acids, or nucleic acid fingerprints as explained herein.

Computing system 140, having the results generated by analysis program 142, identifies or flags the biological specimen 120 or portion thereof based on a match between the collected vibrational spectra 116 obtained with spectrometer 110 and vibrational spectra or Raman shift data 154 of library 152 of database 150. The identified match is then presented to the user through a display of computing system 140 or display of other associated computing device utilized by user at 212.

Figure 4:
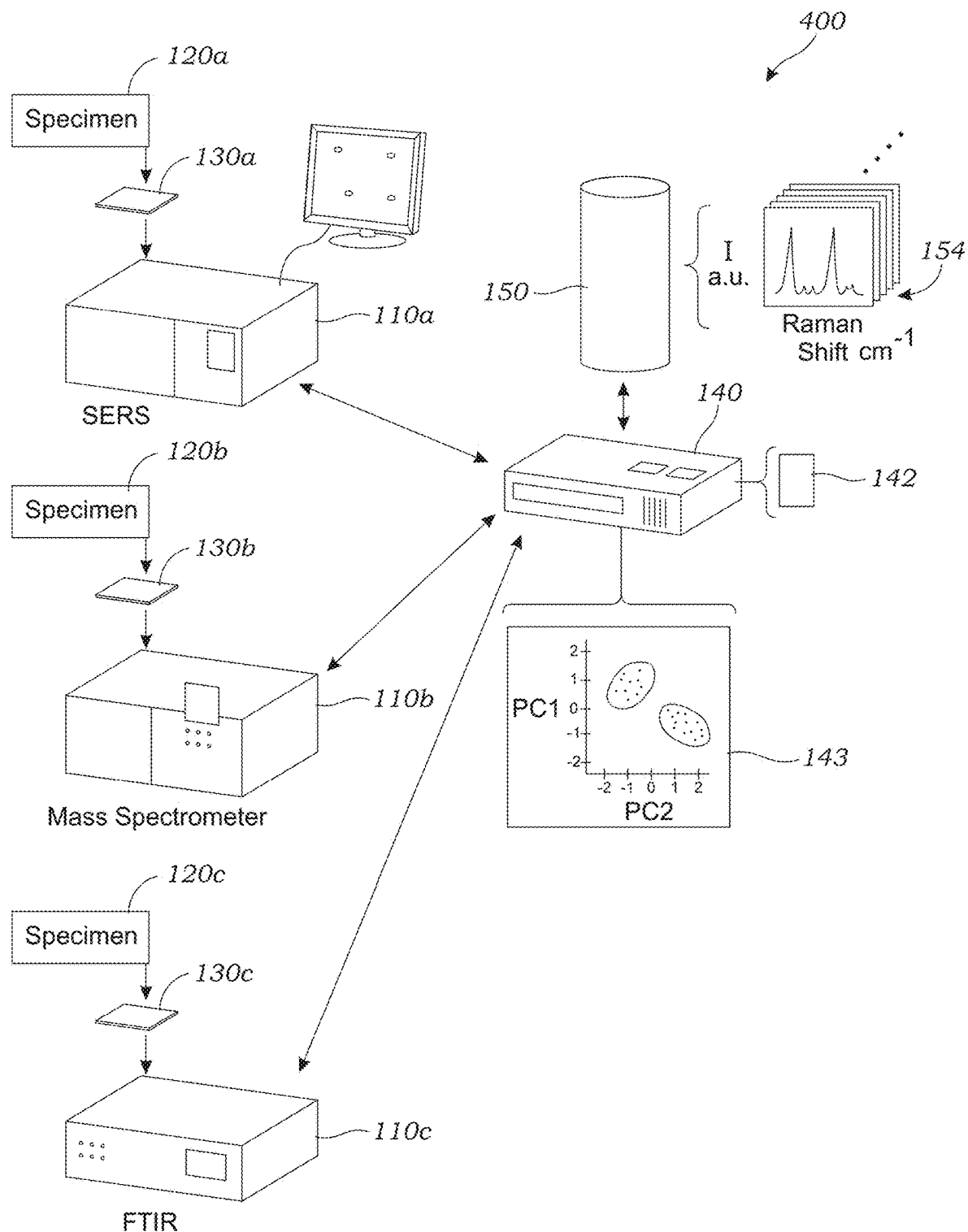
FIG. 4 depicts a system for identifying or characterizing biological specimens utilizing multiple types of spectrometer devices according to one embodiment.

Referring to FIG. 4, while FIG. 1 illustrates system 100 including one spectrometer 110, system 400 embodiments may involve one or multiple spectrometer devices and associated components (identified as "a," "b" and "c"). As an illustrative example, FIG. 4 illustrates a system 400 configuration that includes three different spectrometers 110a-c (SERS, mass spectrometer, FTIR) (generally, spectrometers 110) for respective biological specimens 120a-c (generally, biological specimen 120) loaded onto respective substrates 130 (generally, substrates 130). Spectrometers 110 interface with computing system 140, which may be a local computing system or remote computing system in communication with one or more spectrometers 110 through one or more communication networks. For example, computing system 140 may interface with multiple Raman spectrometers 110 that are at different locations or testing sites, and respective vibrational spectra data 116a-c can be transmitted between respective spectrometers 110 and computing system 140. For ease of explanation, reference is made to processing involving a single spectrometer device 110 that is in communication with computing system 140.

Having described how biological specimen analysis systems 100, 400 may be structured, component operation and their interoperability to identify or characterize unlabeled biological specimens 120, examples of how embodiments may be implemented involving particular biological specimens 120 and associated system operations are described in further detail with reference to FIGS. 5A-20B. Embodiments involving analysis and characterization of bacteria biological specimens 120 are described with reference to FIGS. 5A-6B, embodiments involving analysis and characterization of biological specimens 120 in the form of cellular elements, entities or structures, e.g., exosomes, are described with reference to FIGS. 7A-13B, and embodiments involving analysis and characterization of biological specimens 120 based on relative abundance data from the spectrometer 110 and executing an analysis program 142 that accesses a database 150 of previously stored relative abundance data, executes a comparison of the relative abundance data of the biological specimen 120 against previously stored relative protein and/or amino acid abundance data are described with reference to FIGS. 14A-20B. It will be understood that while certain embodiments are described with reference to different types of biological specimens 120, which may in solid, semi-solid, wet or fluid/liquid form and different biological specimen preparation devices and methods and biological specimen 120 forms and delivery devices and analysis are described, such components and processing may also be applicable to various other biological specimens and characterizations thereof to identify a health state or condition, bodily fluid, cell type, element or structure. Accordingly, the particular embodiments and examples described below with reference to figures are intended to be non-limiting examples of how embodiments may be implemented and different system configurations for same.

Referring to FIGS. 5A-D and 6A-B, a biological specimen characterization system 500 constructed according to one embodiment is operable to identify or characterize a biological specimen 200 including or in the form of a bacteria, e.g., to determine whether a subject has a bacteria infection.

Figure 6A:
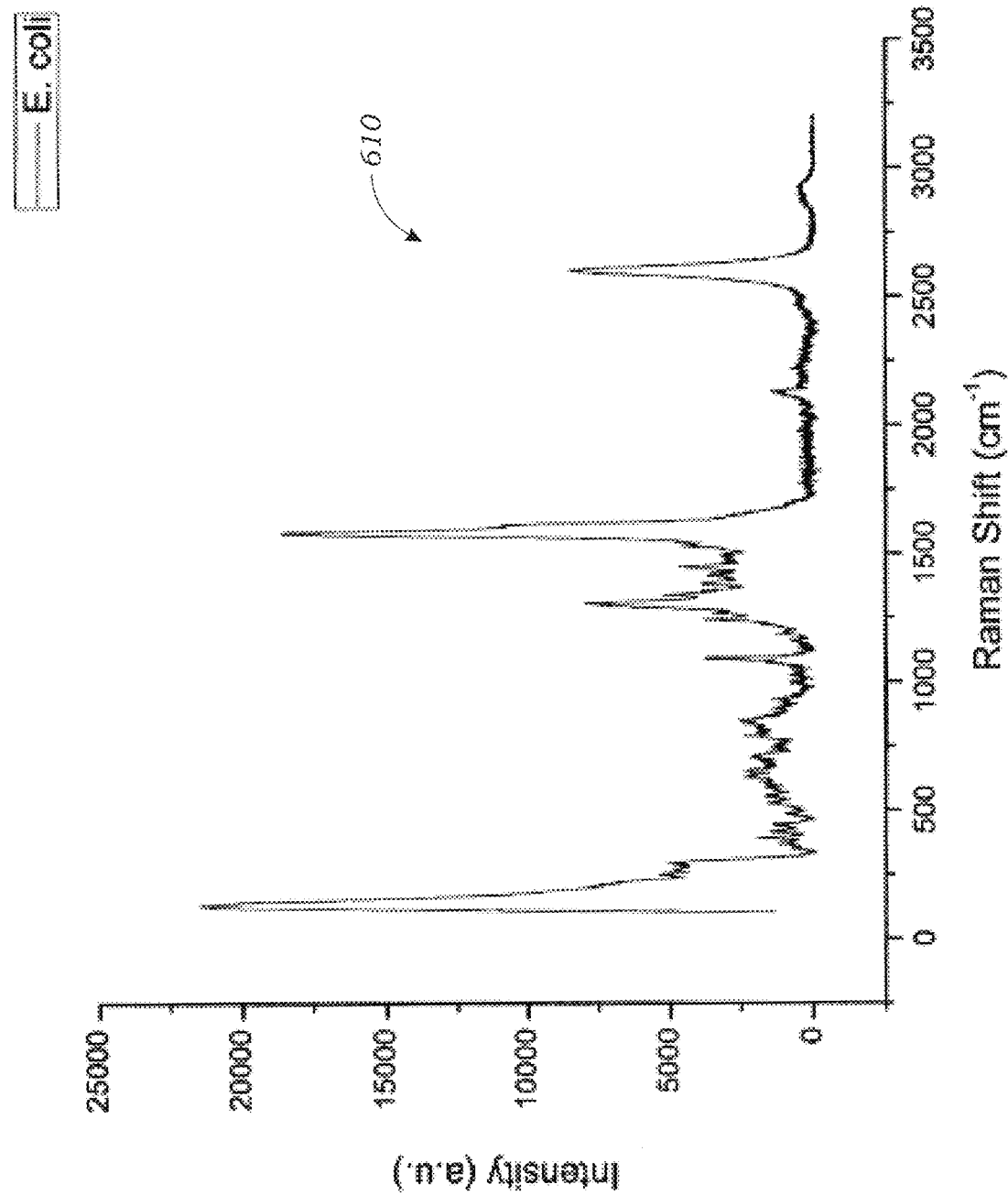
FIG. 6A is the Surface Enhanced Raman Spectroscopy spectra obtained of *E. Coli* K12 ($10^{11}$ cells/ml) in extended mode.
Figure 6B:
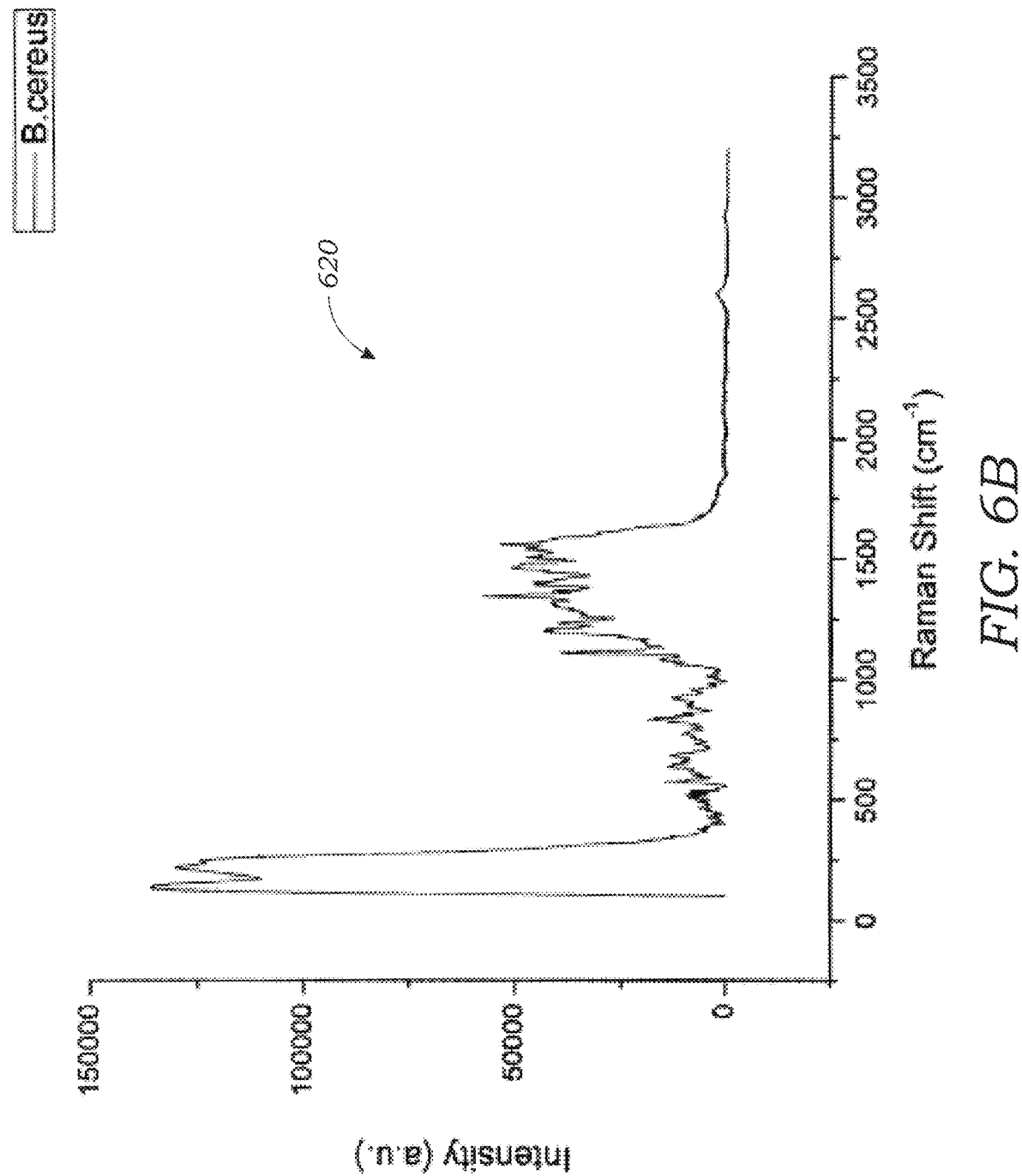
FIG. 6B is the Surface Enhanced Raman Spectroscopy spectra obtained of *B. cereus* K12 ($10^9$ cells/ml) in extended mode.

In the illustrated embodiment, library 152 includes vibrational spectra or Raman shift data 154 of various types of bacteria. FIGS. 6A-B are examples of known vibrational spectra or Raman shift data 154 of bacteria library 152. FIG. 6A depicts a SERS Raman spectra obtained of $E.\ Coli$ K12 ($10^{11}$ cells/ml) 610 in extended mode using plasmonic substrate 130 having a plurality of plasmonic nanofeatures 132 disposed on a surface of substrate 130 and a vdW material 136 further disposed on plasmonic substrate 130 and over plasmonic nanofeatures 132. FIG. 6B depicts a SERS Raman spectra obtained of $B.\ cereus$ K12 ($10^9$ cells/ml) 620 in extended mode using the same substrate 130. It will be understood that these vibrational spectra data or Raman shift data 154 of bacteria library 152 are provided as illustrative examples, and embodiments may utilize many more known bacteria profiles. Each bacterium species has a unique vibrational spectra or Raman shift signature 154 and thus a unique statistical profile (such as PCA) that represents molecules (e.g., proteins) that are expressed or found on the exterior of the bacteria. The signature is represented by the various intensity peaks found in the Raman shift data and relationships between the various peaks. The Raman signature or fingerprints based on intensity peaks and/or relationships between peaks are stored in database 150.

In the illustrated embodiment, the system 500 includes spectrometer 110, a substrate 130 on which biological specimen 120 has been loaded (e.g., by fluid flow such a bodily fluid or blood sample), computing system 140 and database 150. For example, peripheral blood without further processing may be placed on plasmonic substrate 130 (e.g., using one or more drops via a fluid delivery device or dropper) and the blood is allowed to dry either naturally or using vacuum drying. Whole blood may be tested. Alternatively, the blood may undergo pre-processing such as centrifugation to remove red blood cells (RBCs). Additional pre-processing may be done to remove WBCs, proteins, and cell remnants before the biological specimen 120 is subjected to electromagnetic radiation for spectroscopy analysis.

In one embodiment, biological specimen (e.g., blood or other biological sample) is incubated for a period of time in increase the relative concentration of the bacteria with respect to other background components such as red blood cells, white blood cells, and platelets. Because of the rapid multiplication of bacteria over other cells present in bodily fluids, incubation serves the purpose of enriching the bacteria in the sample relative to other cells and constituents. Once the biological specimen 120 has been incubated for a sufficient period of time (e.g., hours or few days), spectrometer 110 can be activated to determine the vibrational spectra data 116 for comparison with bacteria library 152 records or bacteria profiles.

In the illustrated embodiment, biological specimen 120 in the form of a single bacterium is disposed atop plasmonic substrate 1320. Bacterium may be located directly on top of one or more nanofeatures 132 (e.g., pyramids) or bacterium may reside in region between where nanofeatures 132 are located. Regardless of the bacterium location, the presence of bacterium in combination with hybrid plasmonic surface 134 boosts SERS enhancement factor considerably.

In the illustrated embodiment, spectrometer 110 generates vibrational spectra data 116 of the blood components that are deposited onto plasmonic substrate 1230. Vibrational spectra data 116 that is recorded includes the intensity of the Raman scattering as well as the Raman shift which is expressed in wave numbers ($cm^{-1}$). Vibrational spectra data 116 is obtained at a plurality of locations on surface of plasmonic substrate 130 by scanning 118 and vibrational spectra may be associated with a particular x, y location on plasmonic substrate 130. In some embodiments, background subtraction may need to be employed to reveal the spectra of the bacteria. For example, some culturing media may contain one or more compounds that fluoresce in response to SERS imaging. This fluorescence by the medium can be subtracted out to reveal the vibrational spectra of the bacteria.

Database 150 may be a proprietary database that is developed internally based on prior experiments and tests run using the same plasmonic substrate 130 that is used to test the unknown samples. Alternatively, the database may be an open or publicly accessible database. For example, a government institution such as the National Institutes of Health may generate or maintain such a database. Thus, database 130 may be generated in different ways and different databases may be utilized to serve as a library 152 for Raman signatures for different bacteria, and database may be generated by using multiple conventional test methods to identify a particular bacterial species while, in parallel, run on the platform described herein to obtain the Raman signature for this particular bacterium.

In one embodiment, database 150 generation and/or updates are executed using the hybrid plasmonic substrate 130 that was utilized to test blood or biological specimens 120 having unknown bacteria, and this data is used to generate the signature or fingerprint data of known bacteria that is stored in the database 150. Known bacteria whose identity is known in advance by other testing procedures can be placed on hybrid plasmonic substrate 130 and used to generate database 150 of vibration spectra or Raman shift data 154. With this protocol and in view of current manufacturing technology, the vibrational spectra data 116 obtained with a first substrate 130 may not match with vibrational spectra data 116 obtained with a second, different substrate 130. Manufacturing improvements and spectra response consistencies may improve in the future such that different hybrid platform surfaces may be used.

Figure 5A:
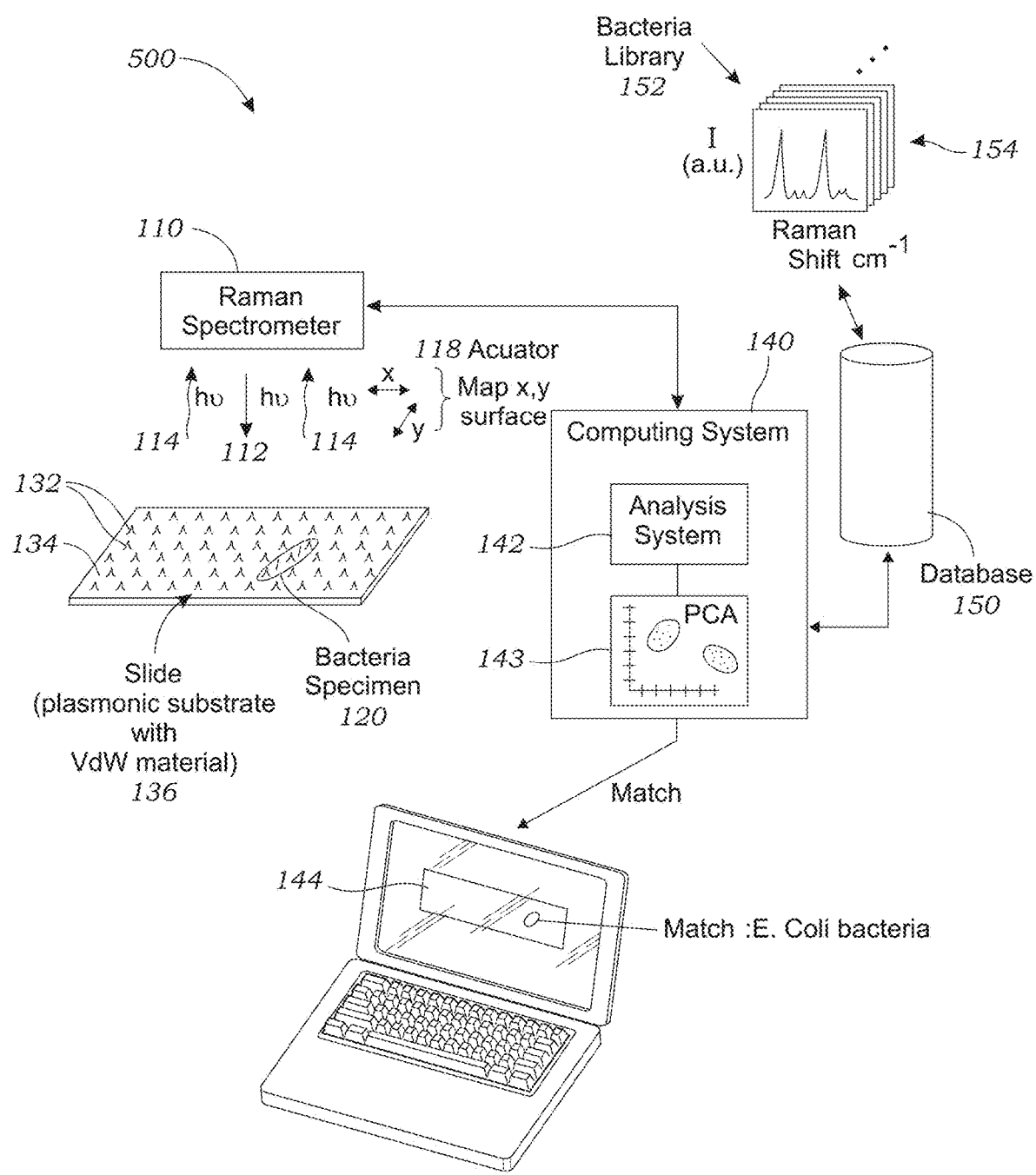
FIGS. 5A-D depict system and methods for identifying or characterizing bacteria biological specimens according to one embodiment, wherein FIG. 5A Illustrates a system for detecting bacteria according to one embodiment.
Figure 5B:
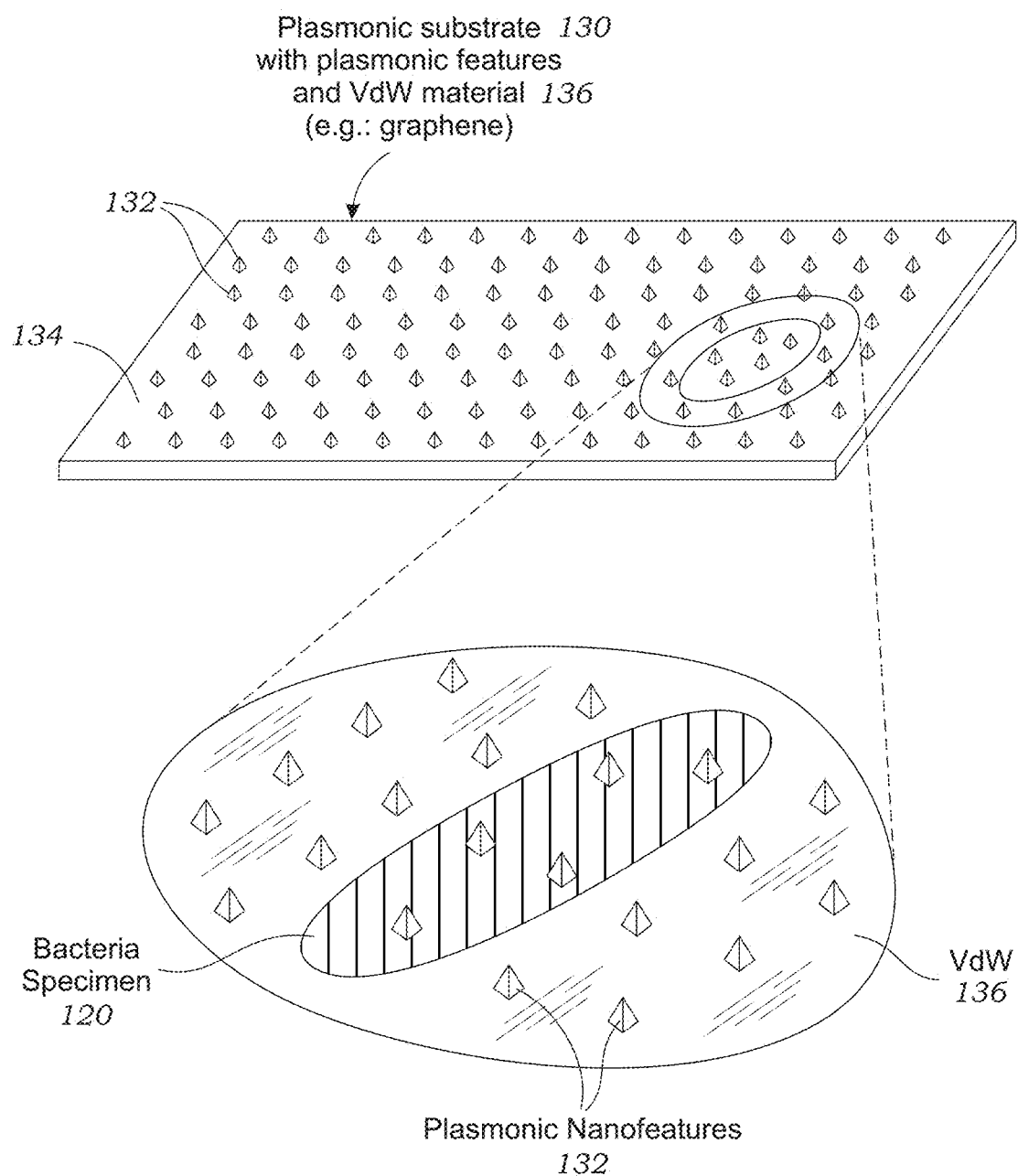
Figure 5C:
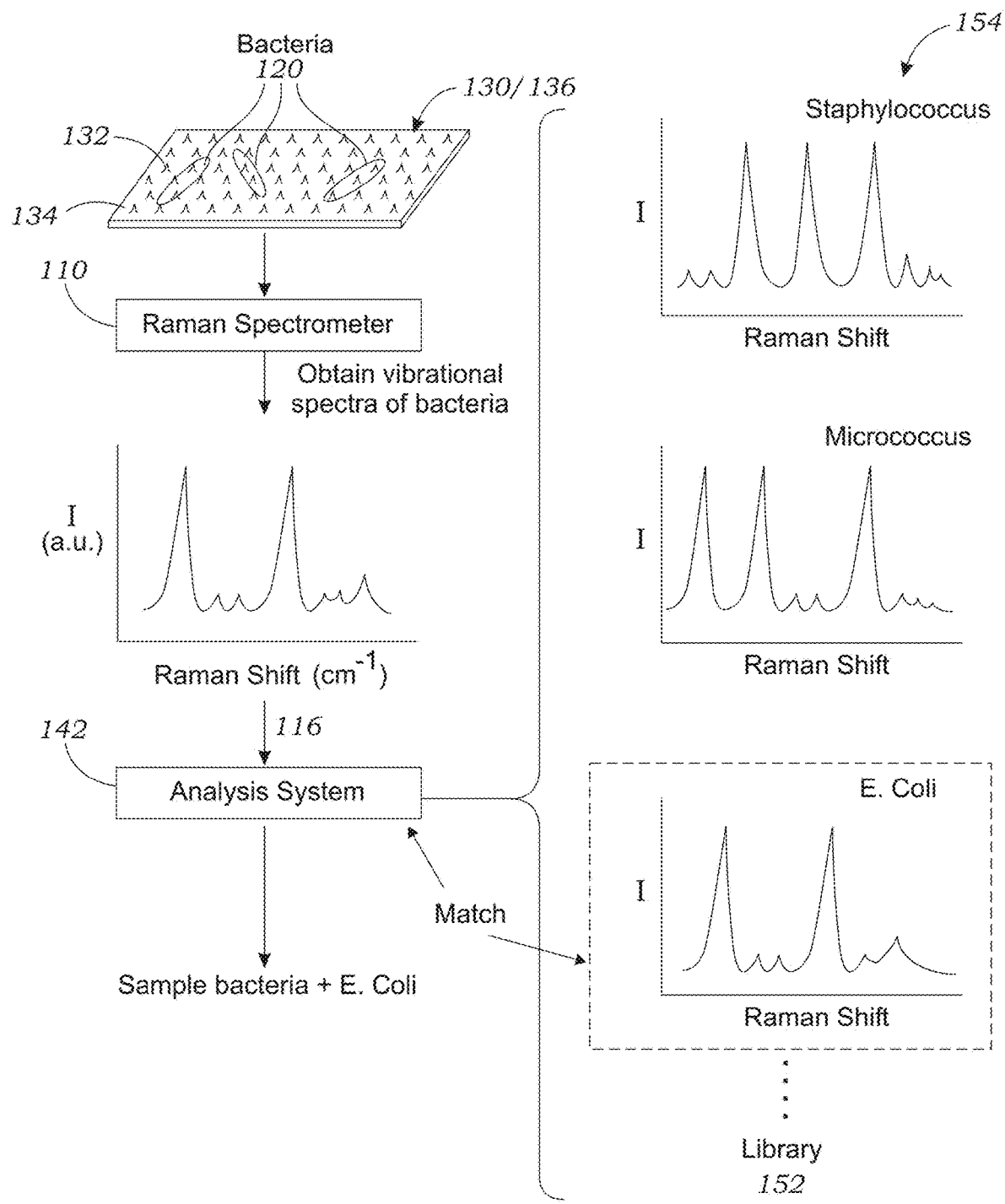
Figure 5D:
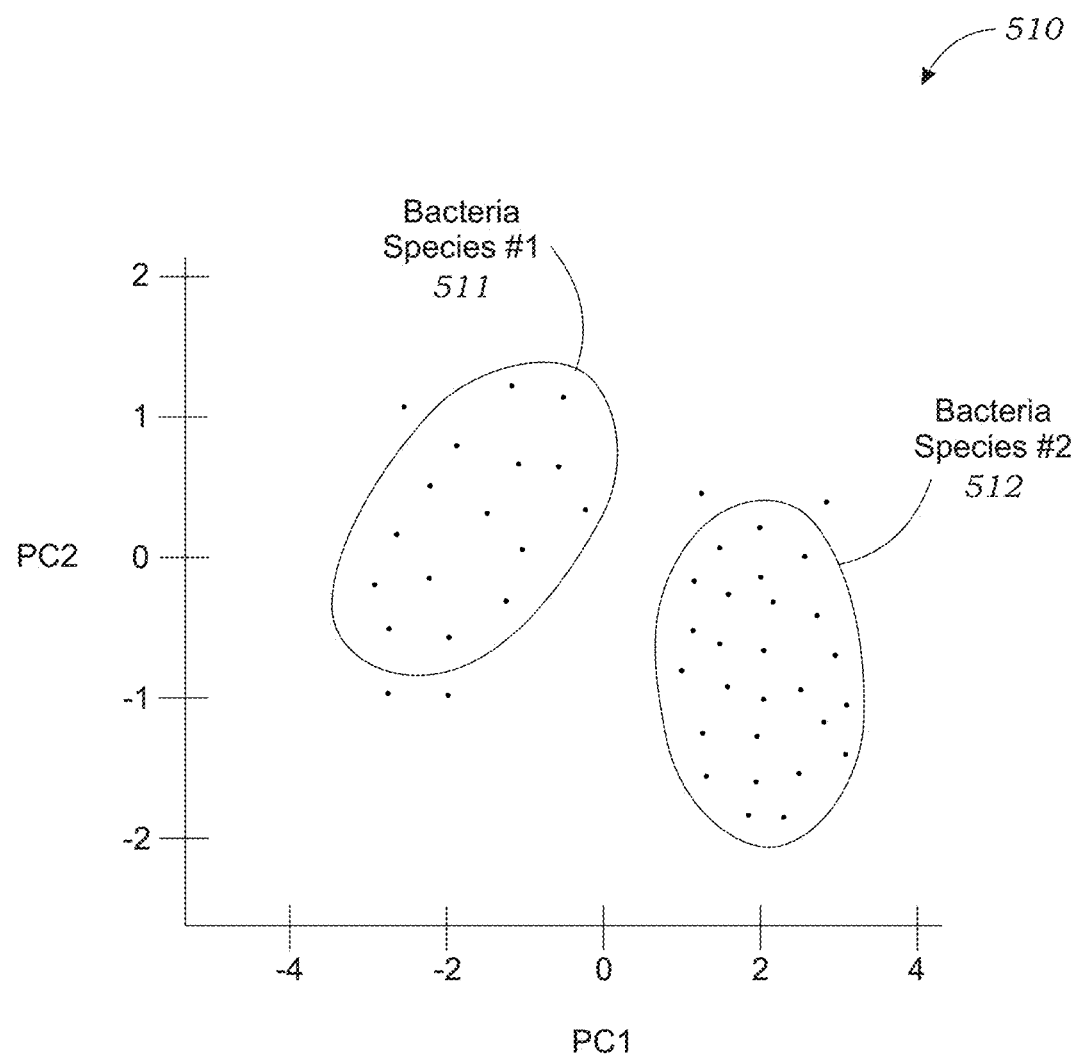

In one aspect of the invention, and with further reference to FIG. 5D, software analysis system 142, which is executed on or by computing system 140, includes a software routine or executable file for performing multivariate analysis such as principle component analysis (PCA) on the spectra of known and unknown bacteria. Software analysis program 142 interfaces with database 150 that includes library 152 containing known signature or "fingerprints" of different types of bacteria using, for example, PCA signatures. Identification or characterization of the bacteria in the tested biological specimen 120 is made possible by comparing the collected vibrational spectra 116 with the library 152 of stored vibrational spectra or Raman shift data 154 for other bacteria in database 150. In the illustrated embodiment, a match or hit was found and analysis program 142 presents the identified bacteria of E. coli. to the user through a display.

FIG. 5D depicts a graph 510 that illustrates how vibration spectra or Raman shift data 154 from a number of known bacteria types (e.g., bacteria types #1 and #2) are identified by their different principal components PC1 and PC2. In this example, a plot 510 of PC1 and PC2 clearly shows that the bacteria of different types are located on different regions of the graph 510 as represented by respective ovals 511, 512. The Raman spectra of an unknown bacterium can be obtained and the principal components obtained to find the species of the bacterium based on the PC1 and PC2 components 511, 512.

Thus, a system 500 constructed according to one embodiment illustrated in FIGS. 5A-D and 6A-B is able to identify or flag bacteria biological specimen 120 or biological specimen 120 containing bacteria based on a match between the collected vibrational spectra data 116 generated by spectrometer 110 and stored vibrational spectra or Raman shift data 154 in database 150, and the identified matching bacteria (e.g., E. coli. Bacteria in the illustrated embodiment) is presented to the user through display of computing system 150 or other computing device.

In one aspect of the invention involving characterization or identification of bacteria, plasmonic substrate 130 is first imaged by spectrometer 110 without any biological specimen 120 loaded thereon. This way, the predetermined positions of nanofeatures 132 and "hot spots" can be determined and recorded. vdW material 136, with its uniform Raman yield, serves the function as a built-in electromagnetic field (EM) gauge of individual hot spots. The locations of these amplifying hot spots can then be noted and used when spectrometry is performed on the same plasmonic substrate 130 holding biological specimen 120. For example, in some embodiments, data from or near these hot spots is used to identify bacteria since these regions give the highest response. The recorded vibrational spectra data 116 can be analyzed and matched against the spectra of known bacteria of database 150 as described above.

Because the principle of bacteria detection using, for example, the hybrid SERS platform, is by detecting molecular vibration fingerprints of molecules expressed on the external surface of the bacteria (e.g., proteins expressed on the outer surface of the bacteria that contact the plasmonic substrate 130), embodiments may also provide for differentiation of detection of a bacterium from the protein background present in human blood. Some residual proteins are extended even in pre-processed blood samples. To distinguish bacteria from the protein background, Raman mapping over plasmonic substrate 130 surface is employed. Background proteins are typically distributed across the substrate 130 surface uniformly whereas the proteins that are displayed on bacteria are crowded across a region comparable to the size of the bacterium (e.g., under 10 µm along a given dimension). Analysis program 142 can look for such regions of concentration and ignore the remaining background signals. In this regard, mapping over the substrate 130 surface in the x and y directions can reduce the chance of false positives.

The platform and system described herein are suitable for use in all medical laboratories and the skill requirement of the operators is minimal as a result of system automation that reduces human interactions and judgment as a result of offloading data analysis and eliminating or reducing human error and uncertainty such that various trained medical laboratory technicians can perform tests. Another benefit is that plasmonic substrate 130 can be prepared in advance and has a long shelf life. A biological specimen 120 is simply loaded onto hybrid plasmonic substrate 130 and then spectrometer 110 can be activated for automated scanning or mapping 118 of same.

Compared to the current blood culture practice, embodiments provide for clear improvements in accuracy and efficiency. For example, the orders of magnitude higher sensitivity of SERS over that of the currently employed methods for Gram typing allows the incubation time to be greatly shortened by a factor of two or more. Further, the labor-intensive steps of Gram type determination and the subsequent culture and sensitivity process can be eliminated and replaced by collection of Raman spectra of the analyte with the subsequent type determination being performed by computing system 150. Additionally, the types of bacteria that can be identified using embodiments is as large as the database 150 to include all the bacteria known to man, which could be order of magnitude larger than in the current practice (current culture and sensitivity processes are limited by the types of antibiotics used in the plated growth media).

Referring now to FIGS. 7A-13B, another example of how embodiments may be implemented involves identifying or characterizing biological specimens 120 in the form of cellular structures or vesicles such as exosomes. Extracellular vesicles (Extra-cellular vesicles) are complex structures comprising a lipid bilayer that contains transmembrane proteins and encloses soluble hydrophilic components derived from the cytosol or other organelles of the donor cell. Extra-cellular vesicles play an important role in intercellular communication by serving as vehicles for transferring biochemical messages among cells. Exosomes are the most abundant and best-characterized type of Extra-cellular vesicles and are distinguished from other Extra-cellular vesicles by their small diameter of 30-200 $nm^3$. Exosomes contain abundant proteins, signaling lipids, and nucleic acids, including mRNA and miRNA. They are capable of mediating a wide variety of biological functions.

Figure 7A:
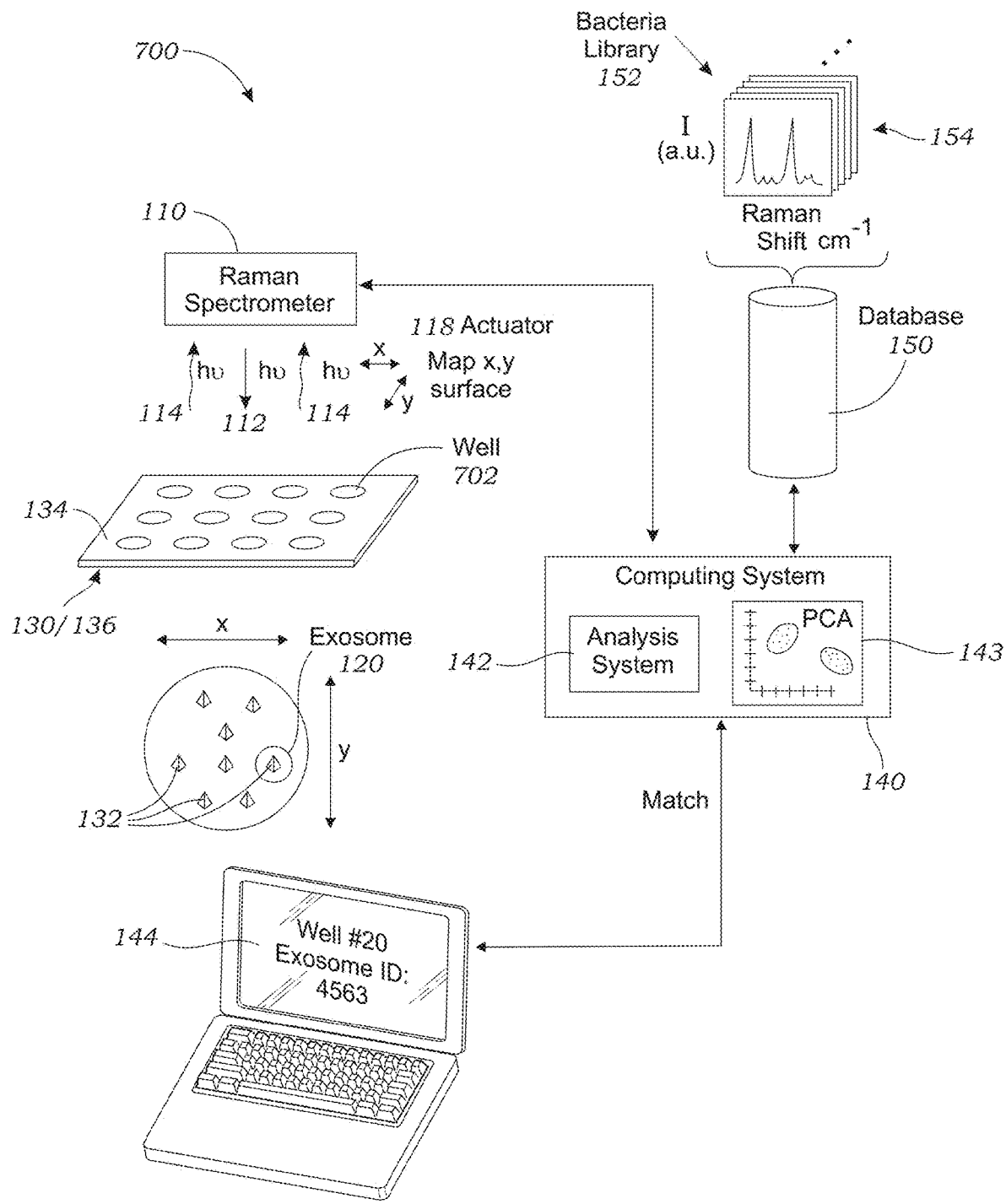
Figure 7B:
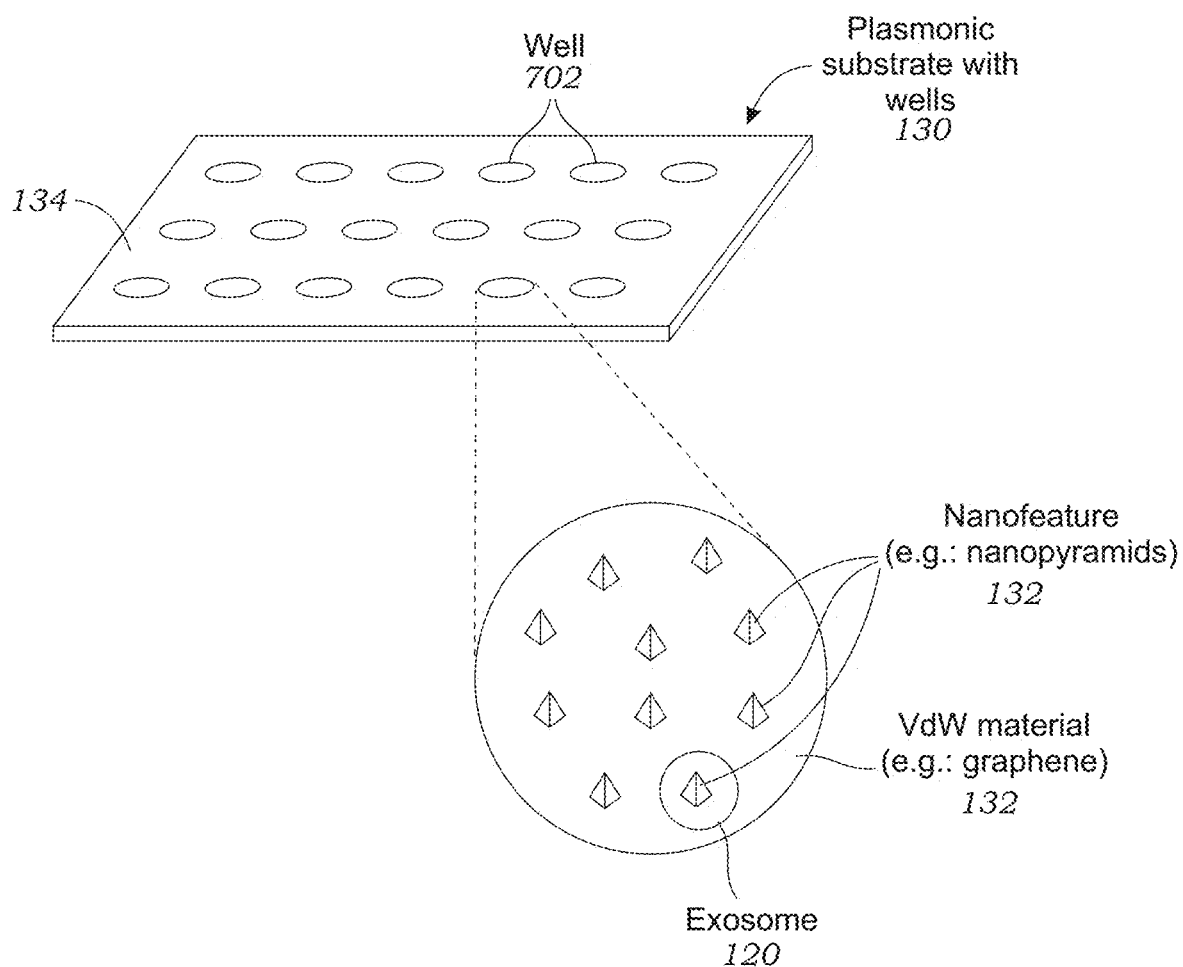
Figure 7C:
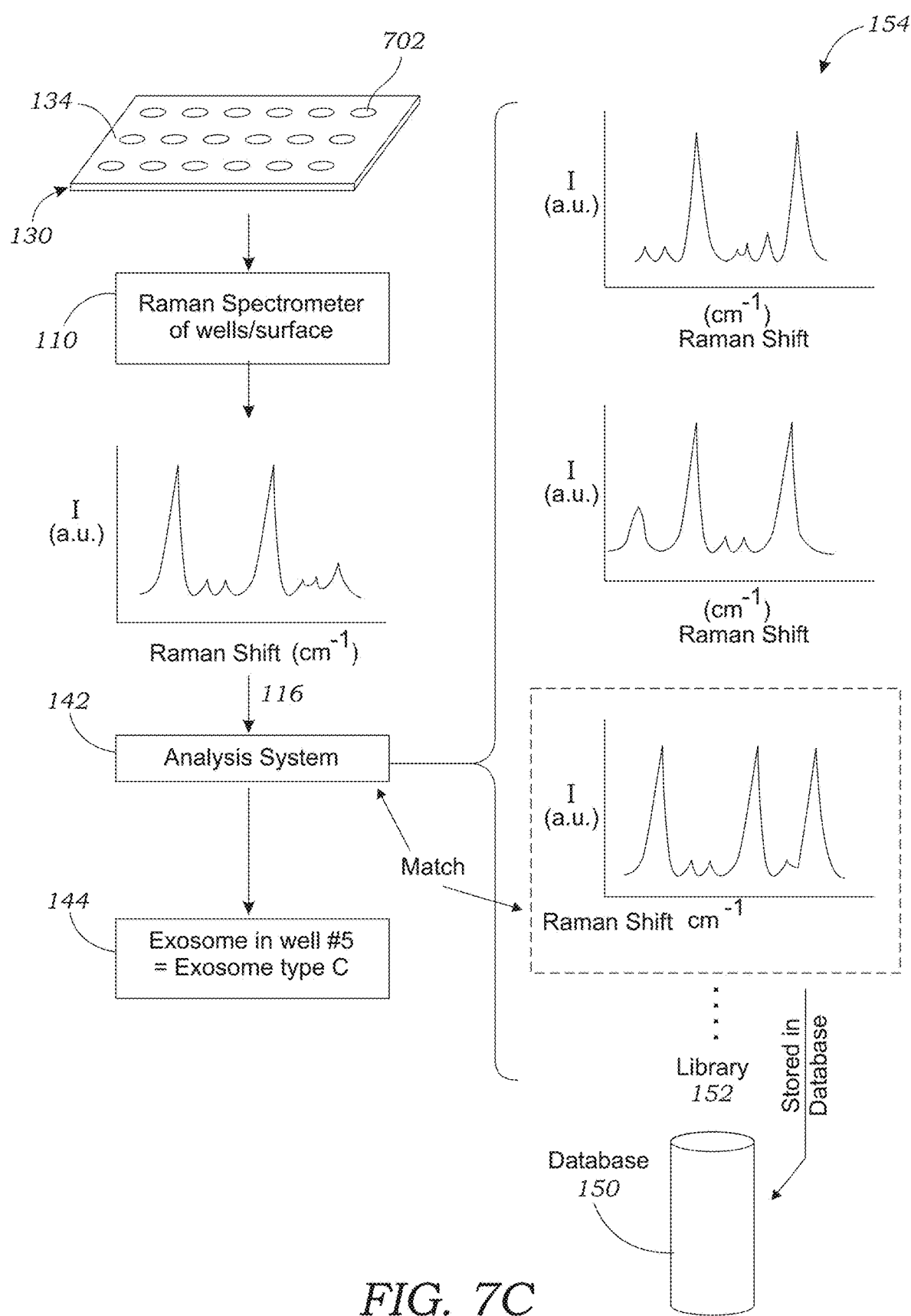

Referring to FIGS. 7A-C, specimen characterization or identification system 700 includes spectrometer 110, a substrate 130 on which biological specimen 120 has been loaded, computing system 140 and database 150 components, various aspects of which are described above and not repeated. In these embodiments, a different substrate 130 configuration may be utilized. In the illustrated embodiment, the substrate 130 defines a plurality of wells 702 for holding biological specimens 120, and nanostructures such as nanopyramids 132 are formed on a bottom surfaces of wells 702.

An exosome-containing specimen 120 is prepared and placed on the plasmonic substrate 130 and in wells 702 and dried (e.g., using applied vacuum). Spectrometer 110 is activated to generate vibrational spectra data 116, and for this purpose, substrate 130 is scanned or mapped 118. Scanning 118 may be executed as shown in FIGS. 7E-F using a multi-stage scan process including a coarse scan (FIG. 7E) and a fine scan (FIG. 7F). For example, an initial scan of a 20 μm×20 μm with a 1 μm pixel size may be performed followed by a subsequent fine scan performed over a 2 μm×2 μm region (within the coarse scanned region) with a 0.1 μm pixel size. For the coarse scan, any pixel containing a surge in the Raman peaks that correspond to those of protein, RNA (typically in the spectral range of 500 to 2,000 cm−1), and lipid (typically in the spectral range of 2,000 to 3,000 cm−1) is presumed to correspond to the presence of an exosome. The finer scan process is used to verify that the surge in Raman signals was indeed due to the presence of exosomes.

Computing system 150 executes analysis program 152 that includes a software routine or executable file for performing multivariate analysis such as principle component analysis (PCA) on the spectra of known and unknown exosomes as well as other extra-cellular vesicles (extra-cellular vesicles). Analysis program 152 interfaces with database 150 that contains signature or "fingerprints" of different types of exosomes or Extra-cellular vesicles using, for example, PCA signatures. The signature is unique to a particular exosome or exosome type and represents the molecules (e.g., proteins) that are contained on or located within the exosome. The signature is represented by the various intensity peaks found in the Raman shift data and relationships between the various peaks.

System 700 is operable to identify biological specimen 120 in the form of exosomes or exosomes in biological specimen 120 based on a match between the collected vibrational spectra 116 generated by spectrometer 110 and stored vibrational spectra or Raman shift data 154 of database 150. As seen in FIG. 7A, for example, the respective identities of two exosomes on plasmonic substrate 130 are determined and presented to user through display. This identification was made by comparing collected vibrational spectra data 116 with the library 152 of stored vibrational spectra or Raman shift data 154 for known exosomes in database 150. In addition, or as an alternative, to the exosome identity, the cellular origin or the exosome may also be displayed or otherwise provided to the user.

Figure 7D:
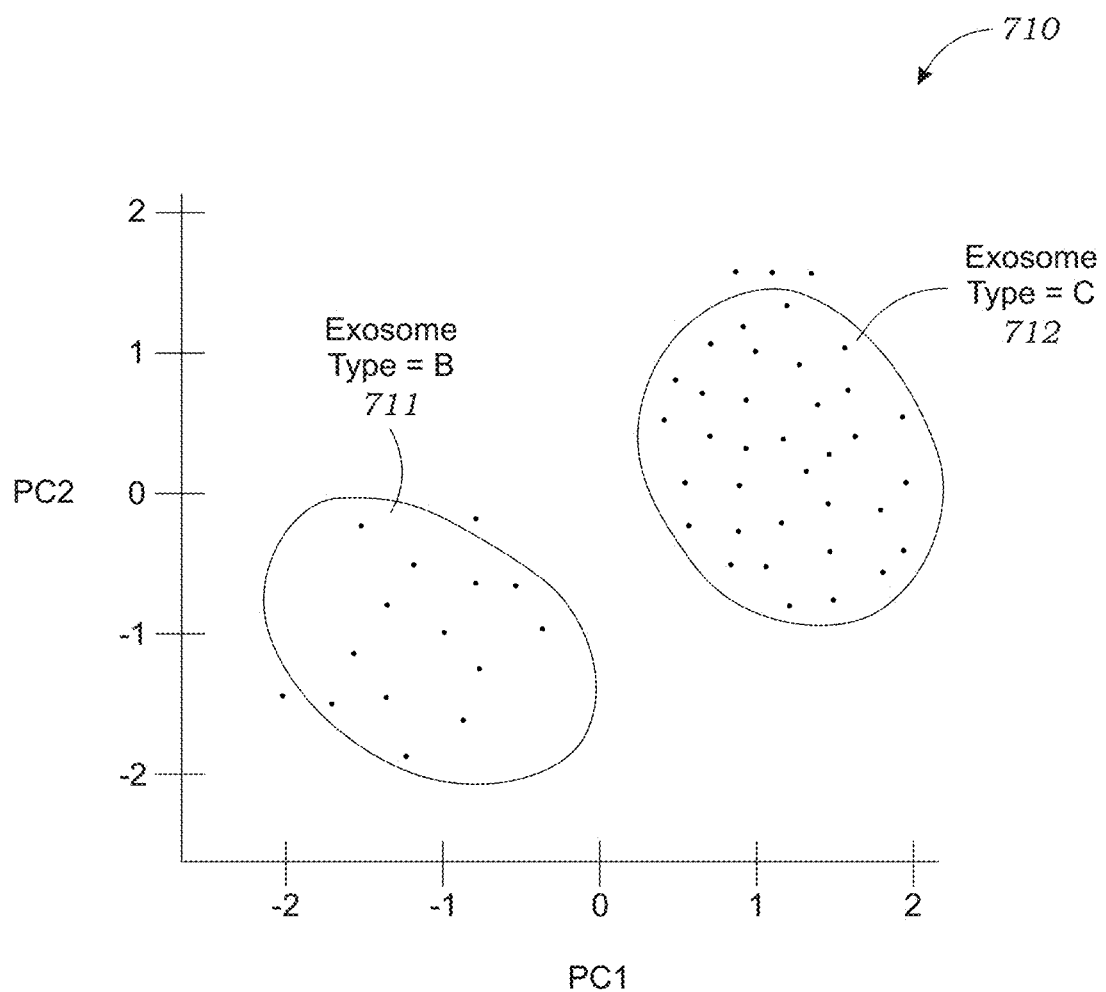
Figure 7E:
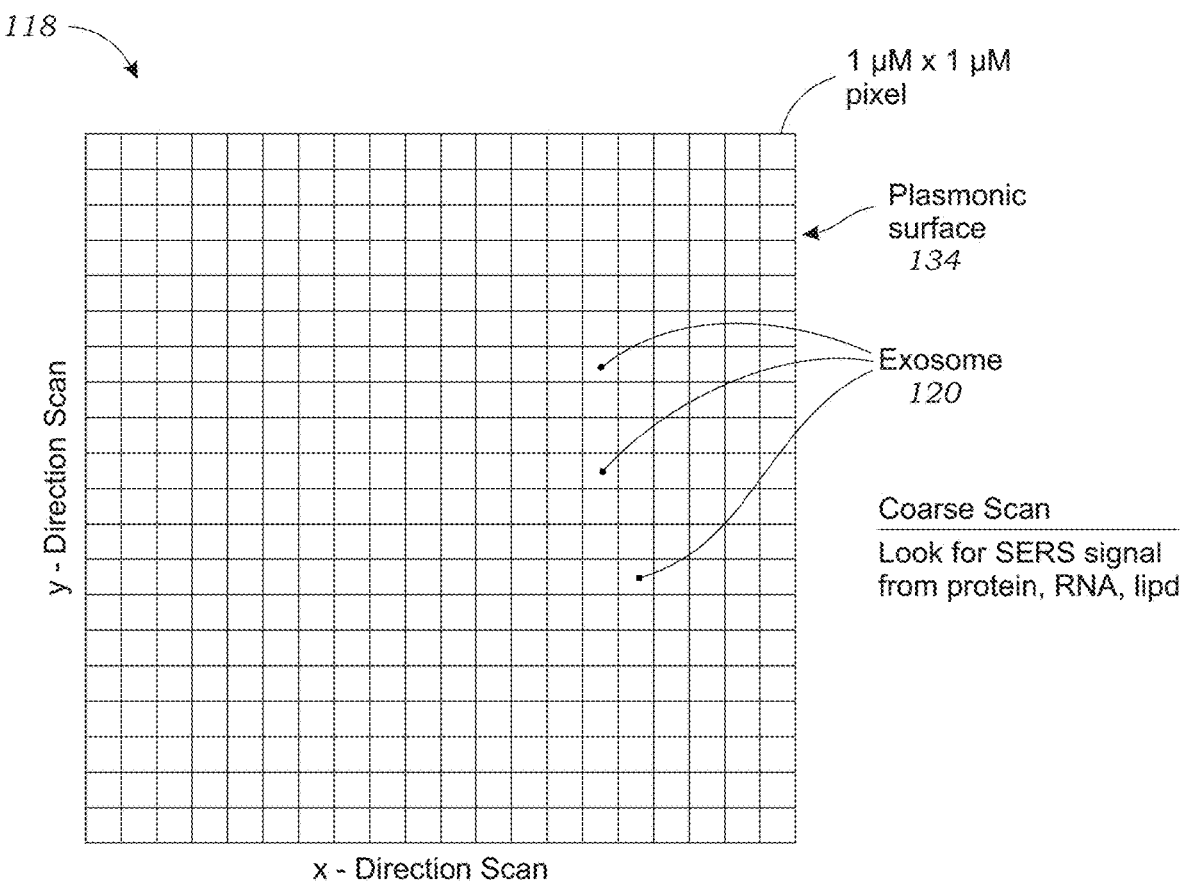
Figure 7F:
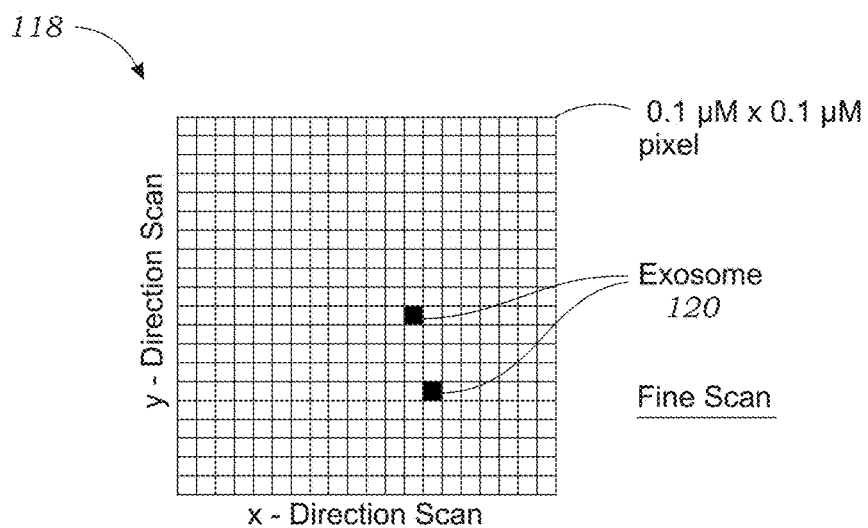

FIG. 7D illustrates how vibrational spectral or Raman shift data 154 from a number of known exosomes are identified by their different principal components PC1 and PC2 in graph 710. In this example, a plot of PC1 and PC2 clearly shows that the different exosomes are located on different regions of the graph 710 as represented by respective ovals 711, 712. The Raman spectra of an identified exosome can be obtained and the principal components obtained to find the type exosome based on the PC1 and PC2 components. If the Raman spectral test data falls within the oval that is representative of exosome type B, then the identified exosome can be identified as exosome type B. Similarly, if the test data falls within the oval that is representative of exosome type C, then the exosome can be identified as exosome type C. While the description is given in terms of two principal components PC1, PC2 it should be understood that additional principal components may be used to identify differences in exosomes. In such a case, the data would be represented on higher order dimensional plots.

Analysis program 152 is able to count all exosomes in the biological specimen 120. In one aspect of the invention, plasmonic substrate 130 is first imaged by spectrometer 110 without any biological specimen 120 loaded thereon. In this manner, predetermined positions of nanofeatures 132 and "hot spots" can be determined and recorded and vdW material 136, with its uniform Raman yield, serves the function as a built-in electromagnetic field (EM) gauge of individual hot spots. Locations of these amplifying hot spots can then be noted and used when Raman spectrometry is performed on the same plasmonic substrate 130 that holds the exosome-containing biological specimen 120. The recorded vibrational spectra data 116 can be analyzed and matched against the vibrational spectra or Raman shift data 154 of known exosomes in database 150.

Experimental

Raman-Spectroscopy Characterization of Single Exosomes.

Figure 8A:
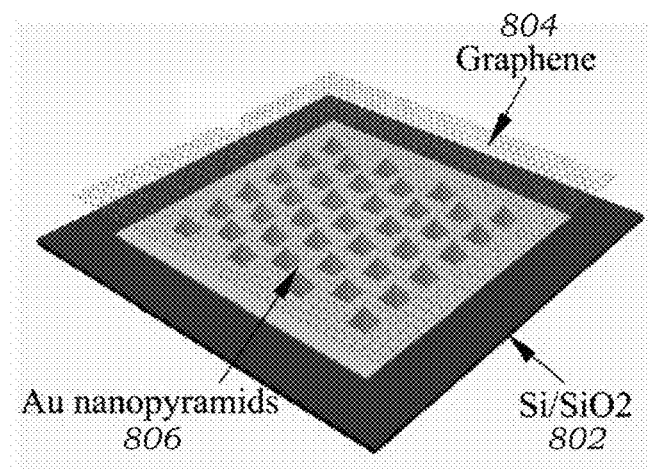
FIG. 8A illustrates a schematic diagram of the hybrid platform used in experiments as described herein.
Figure 8B:
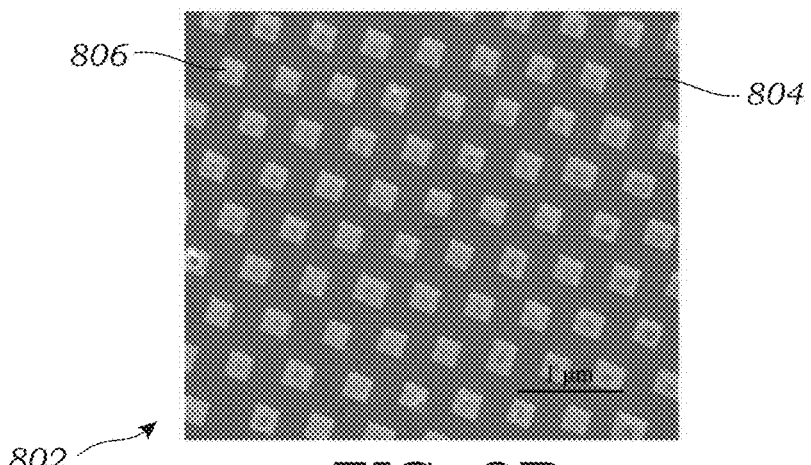
FIG. 8B illustrates a Scanning Electron Microscope (SEM) image of the hybrid platform.

Referring to FIGS. 8A-B, in order to characterize the Raman signature of a biological specimen 120 in the form of or containing exosomes, plasmonic substrate 130 for providing SERS enhancement is utilized, which includes a Si/SiO$_2$ substrate 802 and a graphene 804—Au pyramidal 806 structure, referred to as the hybrid platform. This platform has a demonstrated Raman enhancement factor of up to $10^{12}$. In one embodiment, the base dimension of nanopyramids 132 was ~200×200 nm and the center-to-center distance between adjacent nanopyramids 132 was ~400 nm. This periodic Au nanopyramid structure was fabricated using a patterning method via a layer of self-assembled polystyrene balls, providing a reproducible and uniform SERS response. Such a fabrication process flow can be scaled up to mass production using photolithography of silicon integrated circuit technology.

Figure 8C:
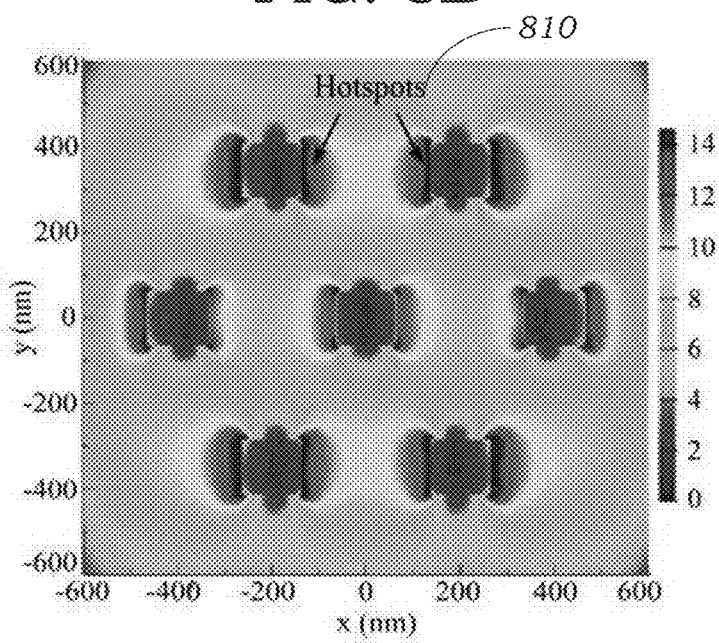
FIG. 8C illustrates the electromagnetic field distribution simulated by FDTD at an input wavelength of 785 nm. The bar represents the electric field intensity.

Graphene layer 804 placed on top of metal surface provides a biocompatible surface, independent of the type of metal used, for supporting plasmon resonance. Graphene layer 804 is chemically inert and impermeable to even He atoms so it protects the metallic nanostructures from possible corrosion including oxidation while preventing biological entities such as cells from being inadvertently affected by certain metals such as silver. The Raman signal of the graphene layer 804 also serves as a built-in gauge of local electromagnetic field intensity. Therefore, the Raman signal intensity from different sets of substrates 130, or different spots measured on the same substrate 130 can be compared quantitatively by normalizing the signal to the graphene Raman peaks. The process flow for the fabrication of the hybrid platform is explained in detail below (Experimental Methods). The local electromagnetic field distribution on the hybrid platform can be simulated using a finite-difference time-domain method (FDTD). A typical result is shown in FIG. 8C and the hotspots 810, where the electromagnetic field is highly enhanced, are on each side of the nanopyramids 806.

In initial experiments, exosomes 120 were isolated from FBS specimens by a series of preparation processing including differential centrifugation, ultrafiltration, and ultracentrifugation to isolate pure exosomes and this is expected to yield a higher signal-to-noise ratio. Alternatively, Extracellular vesicles can be isolated using gentle salting-out solutions.

Figure 9A:
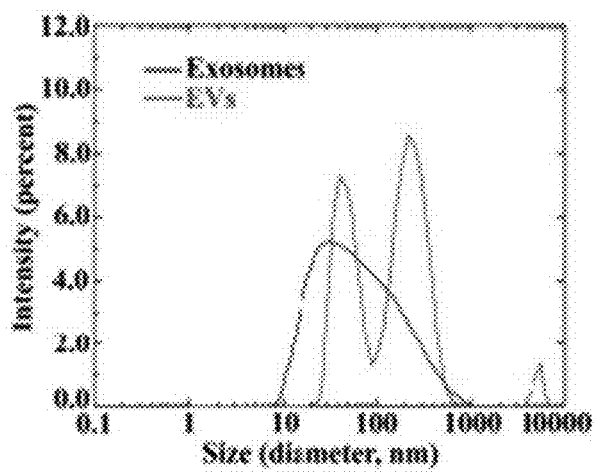
FIG. 9A illustrates DLS spectra showing the particle size distribution of exosomes and EVs.

In one process, as a first step, two preparation s were compared—exosomes 120 isolated by ultra-centrifugation/filtration (referred to as exosome preparation) versus extra-cellular vesicles generated using am ExoQuick kit from System Biosciences. Both preparations were made from FBS specimens. The size distributions of the vesicles were determined using dynamic light scattering (DLS) and tunable resistive pulse sensing (TRPS). The DLS analysis showed that the pure exosome preparation contained a single peak with a maximum at diameter ≈20 nm (FIG. 9A), consistent with the definition of exosomes. Some particles larger than 200 nm were also observed (FIG. 9A). However, the amount of these particles was minute and is highly exaggerated by the DLS spectrum because the intensity of the DLS signal is proportional to the square of the particle mass. The single peak observed following the stringent exosome-isolation protocol was in stark contrast with the substantially broader size distribution of particles observed following isolation of Extra-cellular vesicles using a commercial kit (FIG. 9A), which comprised three peaks at diameter ≈30, 300, and 6,000 nm. TRPS analysis displayed a single peak with a mean diameter of 135±33 with d90 value of 165 nm (i.e., 90% of the vesicles having diameter below 165 nm) when exosomes were isolated by ultracentrifugation/ultrafiltration (FIG. 9B), whereas the Extra-cellular vesicles prepared using a commercial kit had a mean diameter of 143±47 nm and d90 value of 189 (FIG. 9C).

Morphological examination of the isolated vesicles showed that exosomes of similar size existed in both preparation (FIGS. 9D, 9E), yet the EV population contained substantially more structures that looked like cell debris or protein aggregates. Western blot analysis using the exosomal marker proteins Alix, CD9, and CD81 (FIG. 9F) confirmed that these markers were enriched in both populations relative to the serum. The concentration of Alix was somewhat lower in the EV preparation relative to the pure exosomes, whereas the concentration levels of CD9 and CD81 in both preparations were similar.

After establishing the differences and similarities between the two preparation methods in terms of the size distribution, morphology, and presentation of typical protein markers, SERS spectra were collected using the hybrid platform to test if one or both preparation methods yielded representative Raman finger-print information. For each sample, 100 SERS spectra were collected over different spots so that each spectrum was collected from a different exosome or EV (see below). This comparison showed a striking difference between the two populations. In the exosome preparation (FIG. 9G), the spectra showed high homogeneity allowing detection of multiple peaks, including minor ones of intensity <50 a.u. In contrast, overlapping spectra of the EV preparation (FIG. 9H) yielded a highly heterogeneous picture, in which locating useful representative data was impossible. The reason for the large variation in spectral features is that the EV preparation method yields highly non-uniform compositions including exosomes, larger-size Extra-cellular vesicles, and cell fragments. As expected, the Raman spectra in FIG. 9H have substantially higher absolute intensity than those in FIG. 9G because the signal generated by the Extra-cellular vesicles was stronger than of the pure exosome preparation. Nonetheless, this result made it clear that the EV preparation could not be used to obtain SERS fingerprints, whereas the pure exosome preparation offered an abundance of useful information. To extract this information, we averaged the 100 spectra of the pure exosomes (FIG. 10) and could assign 21 distinct peaks in this average spectrum using known assignments of Raman spectra in biological samples (Table 1) below.

TABLE 1

Figure 10:
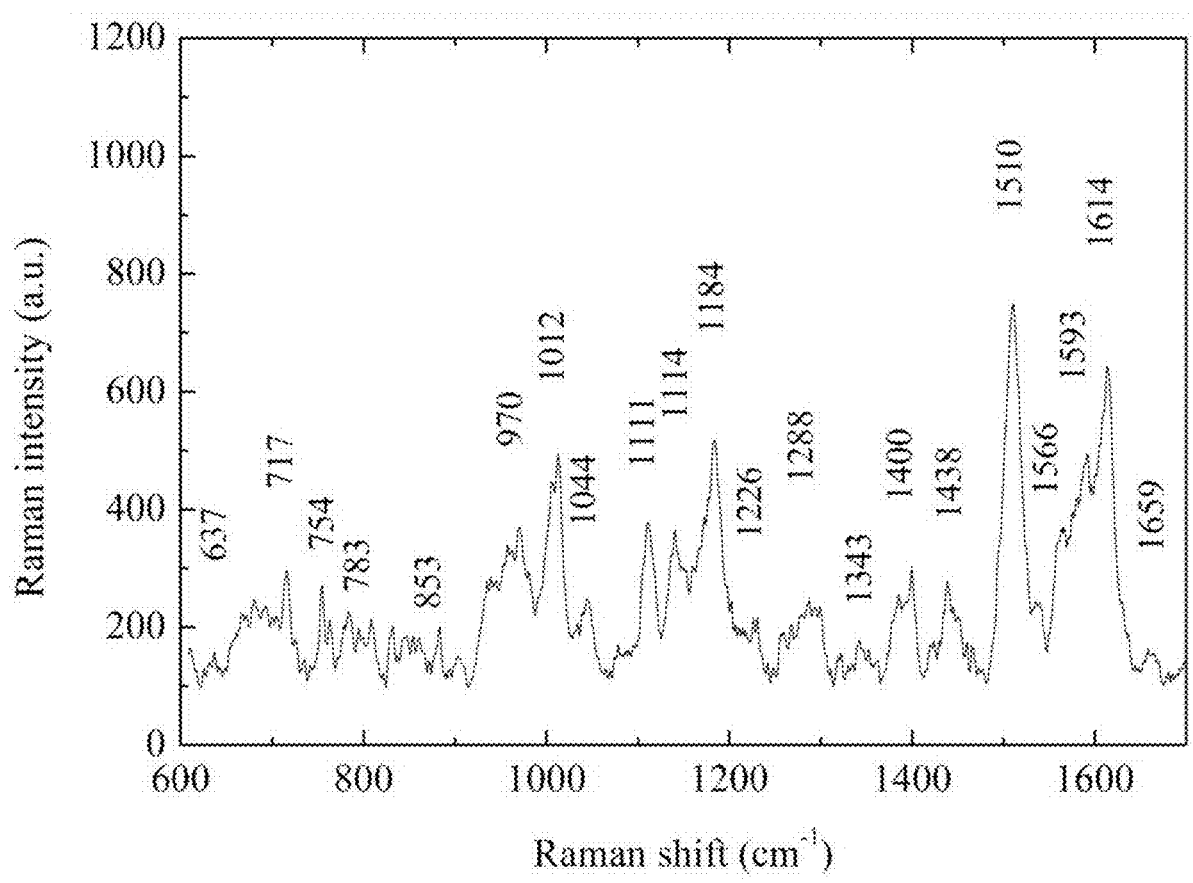
FIG. 10 illustrates an averaged Raman spectrum of exosomes isolated from FBS. The spectrum is an average of the 100 overlaid spectra in FIG. 9G.

Assignment of the Raman peaks shown in the spectrum in FIG. 10

| Raman shift ($cm^{-1}$) | Peak assignment |
|---|---|
| 636 | C—S stretching & C—C twisting of proteins tyrosine |
| 716 | C—N (membrane phospholipids head) |
|  | CN—$(CH_3)_3$ (lipids) |
| 753 | Symmetric breathing of tryptophan |
| 783 | U, T, C (ring breathing modes in the DNA/RNA bases) |
| 853 | Ring breathing mode of tyrosine & C—C stretch of proline ring |

TABLE 1-continued

Assignment of the Raman peaks shown in the spectrum in FIG. 10

| Raman shift (cm$^{-1}$) | Peak assignment |
|---|---|
| 970 | Lipids |
| | Phosphate monoester groups of phosphorylated proteins & cellular nucleic acids |
| 1012 | Phenylalanine |
| 1044 | Proline |
| | $v_3PO_4^{3-}$(symmetric stretching vibration) |
| 1111 | Phenylalanine (proteins) |
| 1140 | Fatty acid |
| 1183 | Cytosine, guanine, adenine |
| 1226 | Amide III |
| 1287 | Cytosine |
| 1342 | G (DNA/RNA) |
| | CH deformation (proteins and carbohydrates) |
| 1400 | C=O symmetric stretch, CH$_2$ deformation |
| | NH in-plane deformation |
| 1438 | CH$_2$ and CH$_3$ deformation vibrations, Cholesterol, fatty acid band |
| 1510 | A (ring breathing modes in the DNA bases) |
| 1566 | Tryptophan |
| 1592 | G (DNA/RNA), CH deformation (proteins, and carbohydrates) |
| 1614 | C=C stretching mode of tyrosine & tryptophan |
| 1659 | Fatty acids, Amide I (collagen assignment), Triglycerides (fatty acids) |

Correlative Study Using Raman Mapping and SEM.

In this section, supporting evidence (through correlation of exosome density obtained using SEM and via Raman mapping) is provided demonstrating that characteristic SERS spectra are indeed that of the exosomes 120 as opposed to extra-cellular vesicles and/or lipid fragments. Due to the heterogeneous nature of the extra-cellular vesicles, the focus was on pure exosome preparation. Because of the small size of the exosomes 120 (30-200 nm), the limited spatial resolution of the optical microscope attached to the Raman spectrometer 110 did not allow for direct visualization of individual exosomes 120 for the purpose of determining the source of the Raman spectra. To reveal the source of the Raman signature, Raman mapping was first carried out on the exosome specimens 120 at three concentrations. To that end, an exosome preparation was either used as-is or diluted 3- or 10-times. At each concentration, Raman spectra across a 10×10-pixel area was collected. The pixel size of the Raman map was set at 2 μm to avoid overlapping of adjacent laser spots. Raman mapping results at the three dilutions 1101a, 1101b, 1101c (FIGS. 11A-1C) showed a density change consistent with the change of the concentration. Three spectral peaks with a high signal-to-noise (S/N) ratio were chosen as characteristic peaks of exosomes: 1012 cm$^{-1}$ (1102) 1509 cm$^{-1}$ (1104) and 1613 cm (1106) representing the vibrational mode of phenylalanine, the ring-breathing mode in DNA bases, and the Raman mode of tyrosine, respectively. The presence of these peaks is indicated by red, yellow and blue pixels, respectively in FIG. 11D. The black pixels represent the existence of the exosomes, which was determined based on the co-existence of all three characteristic Raman peaks in each pixel (FIG. 11D). The Raman mapping results demonstrated that the area density of observed exosomes 120, decreased proportionally with increasing dilution.

Figure 11F:
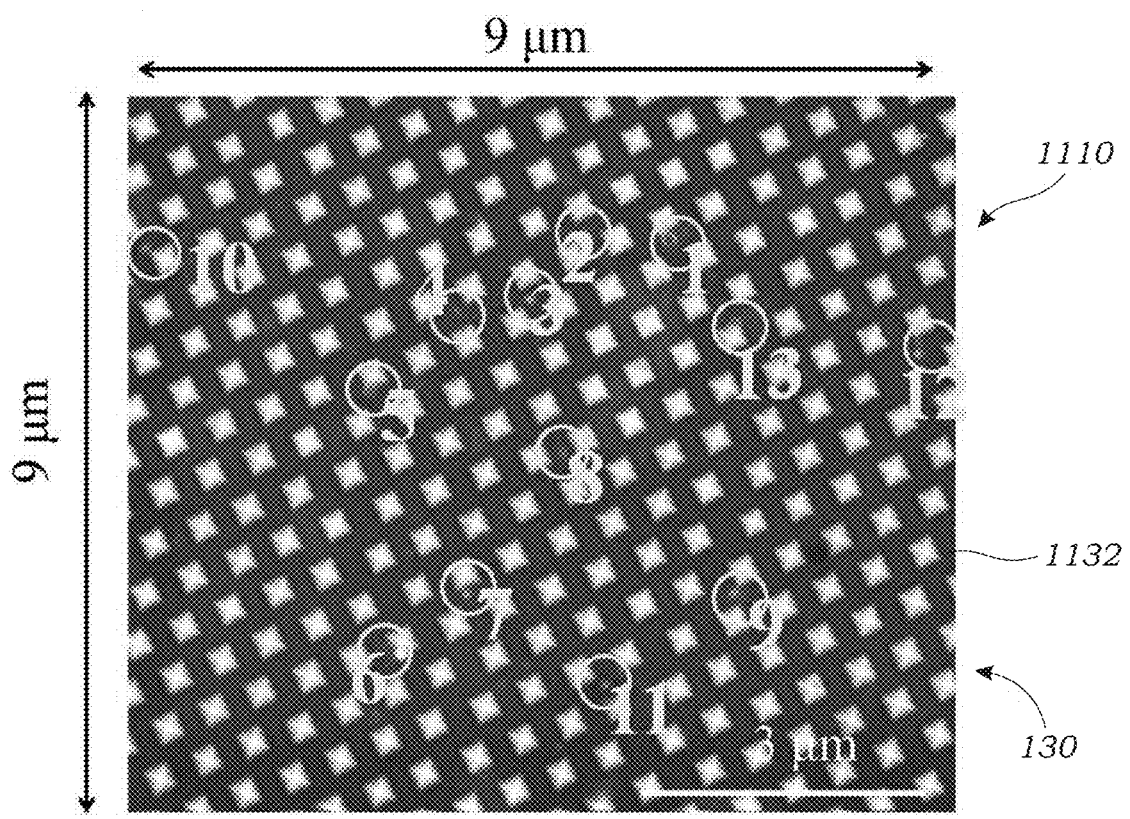
FIG. 11F illustrates a representative 9×9-μm SEM micrograph of exosomes attached to the graphene-covered surface at 35,000× magnification. The yellow circles mark the presence of exosomes within this region.

To visually determine the location of the exosomes on the hybrid platform, SEM 1110 was used to image the exosomes 120 at different concentrations and the results were correlated with the Raman mapping. The exosomes 120 could be observed directly using SEM and their density was calculated by counting the numbers of the exosomes within a randomly selected, 9×9 μm area and comparing it with the Raman mapping results. An example of exosomes observed using SEM in a 3-times diluted sample (FIG. 8E) shows how the exosomes 120 were counted. The final density for each concentration was determined by taking the average of measurements at ten different areas. Comparison of the exosome density obtained separately using Raman mapping and SEM measurement showed a good correlation between the two methods (FIG. 11F). The two measurements showed similar exosome density within experimental uncertainty. Comparison between the Raman mapping and SEM measurement using ANOVA resulted in a p-value of 0.385, indicating no significant difference between these two measurements, whereas the difference among the three dilutions was statistically significant (p=0.017).

Raman Mapping of Individual Exosomes.

Figures 12A, 12B:
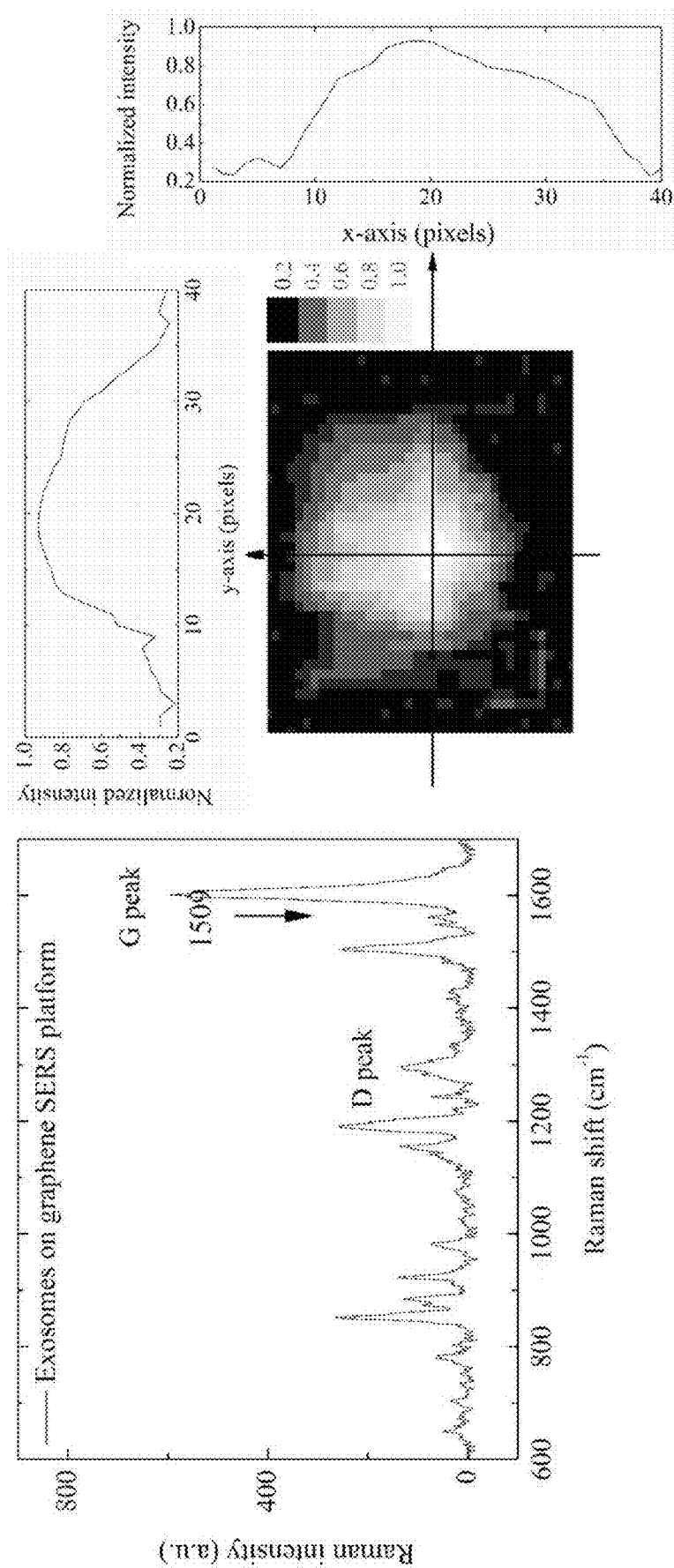
FIG. 12A illustrates the Raman spectrum of a single exosome laid on the hybrid platform, including the graphene D and G peaks.
FIG. 12B illustrates the Raman mapping using a step size of 0.1 μm. The greyscale map is a plot based on the peak intensity at 1509 cm—The peak intensity changes along the x- and y axes across the exosome are shown on the right and top, respectively.
Figure 13E:
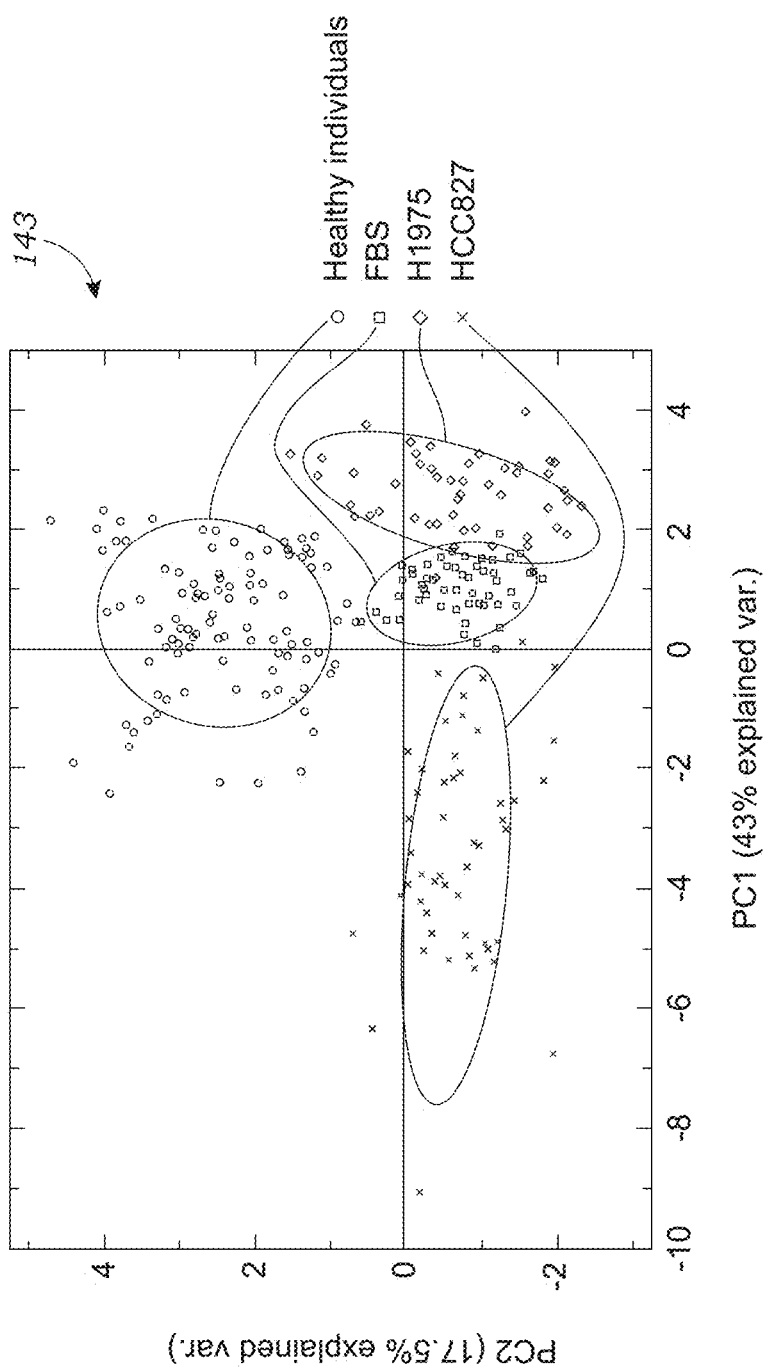

In the Raman mapping shown in FIGS. 11A-11C, variation in the intensity of the Raman signal from pixel to pixel was observed, presumably due to the variation of relative positions between either the exosomes of the Gaussian shaped excitation laser beam and the hotspots 810 (FIG. 8C), where the SERS enhancement mainly comes from. To further validate that the Raman spectra collected indeed was from exosomes, high spatial resolution Raman mapping was performed using 0.1-μm step size (FIGS. 12A-12B). The Raman signal intensity at different pixels was normalized to the graphene G-peak (FIG. 12A) so that the influence of unavoidable hotspot 810 intensity fluctuations was eliminated. Examination of the Raman spectrum of a single exosome showed multiple peaks, among which the graphene peak (G) was easily identified. After normalization to the graphene G-peak, the Raman mapping result was generated based on the intensity of the 1509 cm$^{-1}$ peak by 3D reconstruction of peak intensity changes along the x- and y-axes (FIG. 12B). The lateral spread of ~2 μm of the Raman signal is attributed to the typical diameter of a focused Gaussian beam of the excitation laser convoluted over the ≤200 nm size of individual exosomes. This high-spatial-resolution Raman map provides further support to the likelihood that the Raman spectra at each pixel (8A-8C) were indeed from individual exosomes with the pixel-to-pixel intensity fluctuation being originated from the variation in the relative position between individual hotspots and the exosome or the laser beam.

Distinguishing Exosomes from Different Sources.

SERS spectral features are highly sensitive to the chemical composition of biological molecules. This sensitivity translates directly to specificity when it comes to using SERS for distinguishing exosomes secreted by different types of cells. To test whether SIM could achieve this feat, exosomes 120 from three additional sources were analyzed (two human lung cancer cell lines—HCC827 and H1975, and human serum from two healthy individuals). One hundred Raman spectra from each type of exosomes 120. The spectra of the exosomes 120 from each source showed both similarities and differences (FIGS. 13A-13D). The peak assignments can be found in Tables 2-5 below. Peaks at 1,113, 1,208, 1,340, 1,420, and 1,605 $cm^{-1}$ are characteristic of nucleic acids, peaks at 1,160 and 1,310 $cm^{-1}$ came from lipids, whereas protein peaks included those at 1,260 $cm^{-1}$ (amide III), 1,490 $cm^{-1}$ (amide II), and 1,547 $cm^{-1}$ (amide II). The common Raman peak at about 845 $cm^{-1}$ represents a C-O-C skeletal mode.

TABLE 2

Assignments of the Raman peaks obtained from Raman spectrum of exosomes isolated from serum of healthy individual 1

| Raman shift ($cm^{-1}$) | Peak Assignment |
| --- | --- |
| 805.2 | Phosphodiester |
| 828.6 | Ring breathing tyrosine |
| 864.1 | Ribose vibration, one of the distinct RNA modes |
| 925.5 | Proline & valine (protein band) |
| 966.4 | Lipids |
| 985.2 | C—C stretching β-sheet (proteins) |
| 1035.8 | Collagen |
| 1063.9 | Skeletal C—C stretch of lipids |
| 1170.4 | C-H in-plane bending mode of tyrosine |
| 1255.6 | Lipids |
| 1302.9 | Amide III (protein) |
| 1316.1 | Guanine (B, Z-marker) |
| 1345.7 | $CH_3$, $CH_2$ wagging |
| 1373.3 | T, A, G (ring breathing modes of the DNA/RNA bases) |
| 1386.2 | $CH_3$ band |
| 1427.2 | Deoxyribose (B, Z-marker) |
| 1457.0 | Deoxyribose |
| 1479.6 | Amide II |
| 1515.8 | Cytosine |
| 1553.3 | Amide II |
| 1589.0 | Phenylalanine, hydroxyproline |
| 1616.9 | C=C stretching mode of tyrosine & tryptophan |
| 1655.2 | Amide I of proteins |
| 1728.1 | Ester group |

TABLE 3

Assignments of the Raman peaks obtained from Raman spectrum of exosomes isolated from serum of healthy individual 2

| Raman shift ($cm^{-1}$) | Peak Assignment |
| --- | --- |
| 746.4 | T (ring breathing mode of DNA/RNA bases) |
| 786.8 | DNA: O—P—O, cytosine, uracil, thymine, Pyrimidine ring breathing mode |
| 815.2 | Proline, hydroxyproline, tyrosine, v2 $PO_2$- stretch of nucleic acids |
| 824.6 | O—P—O stretch DNA |
| 844.6 | Monosaccharides (α-glucose), (C—O—C) skeletal mode, disaccharide (maltose), (C—O—C) skeletal mode |
| 866.8 | Ribose vibration, one of the distinct RNA |
| 978.6 | C—C stretching β-sheet (proteins) =CH bending (lipids) |
| 1033.1 | Phenylalanine mode, ν (CO), ν (CC), ν (CCO) (polysaccharides, pectin), C—H in-plane phenylalanine (proteins) |
| 1041.0 | Formalin peaks appearing in fixed normal and tumor tissues |
| 1065.7 | Palmitic acid, Fatty acid |
| 1081.3 | $v_1CO_3$, $v_3PO_4$, ν (C—C) skeletal of acyl backbone in lipid |
| 1091.4 | Backbone-phosphate backbone vibration as a marker mode for the DNA concentration C—N of proteins |
| 1105.9 | Phenylalanine (proteins) |
| 1130.3 | C—C skeletal stretch transconformation |
| 1163.3 | Tyrosine (collagen type I), tyrosine |
| 1221.2 | T, A (DNA/RNA), Amide III (proteins) =CH bending (lipids) |
| 1251.6 | Guanine, cytosine ($NH_2$) |
| 1289.2 | Cytosine, Phosphodiester groups in nucleic acids |
| 1295.6 | $CH_2$ deformation |
| 1302.0 | $CH_3$, $CH_2$ twisting (collagen assignment) $CH_2$ deformation (lipid), adenine, cytosine |
| 1313.8 | $CH_3CH_2$ twisting mode of collagen/lipid |
| 1332.9 | Guanine |

TABLE 3-continued

Assignments of the Raman peaks obtained from Raman spectrum of exosomes isolated from serum of healthy individual 2

| Raman shift (cm$^{-1}$) | Peak Assignment |
|---|---|
| 1374.2 | T, A, G (ring breathing modes of the DNA/RNA bases) |
| 1386.8 | CH$_3$ band |
| 1410.9 | $v_s$COO$^-$ (IgG) |
| 1429.6 | Deoxyribose, (B, Z-marker), CH$_2$ scissoring |
| 1439.0 | CH$_2$ bending mode |
| 1460.8 | CH$_2$/CH$_3$ deformation of lipids & collagen, CH$_2$ wagging, CH$_2$/CH$_3$ deformation, deoxyribose |
| 1482.4 | G, A (ring breathing modes in the DNA bases), nucleotide acid purine bases (guanine and adenine) |
| 1498.9 | C=C stretching in benzenoid ring |
| 1532.6 | Carotenoid |
| 1556.0 | tyrosine, amide II |
| 1569.2 | Guanine, adenine |
| 1589.4 | Graphene D-peak, G (DNA/RNA), CH deformation (proteins, and carbohydrates) |
| 1616.5 | C=C stretching mode of tyrosine & tryptophan |
| 1657.4 | Fatty acids, Amide I (collagen assignment), Triglycerides (fatty acids) |

TABLE 4

Assignments of the Raman peaks from Raman spectrum of exosomes isolated from lung cancer cell HCC827

| Raman shift (cm$^{-1}$) | Peak assignment |
|---|---|
| 607.1 | Cholestrol ester |
| 632.7 | C—S stretching & C—C twisting of proteins-tyrosine |
| 675.2 | Ring Breathing modes in DNA bases |
| 705.3 | Cholesterol, cholesterol ester |
| 726.9 | Phosphatidylserine |
| 741.2 | T (ring breathing mode of DNA/RNA bases) |
| 769.8 | Pyrimidine ring breathing mode |
| 817.0 | C—C stretching (collagen assignment) |
| 854.4 | Ring breathing tyrosine (proteins) |
| 885.8 | (C—O—C) skeletal mode |
| 892.8 | Monosacchardies (β-glucose), (C—O—C) skeletal mode |
| 927.4 | C—C backbone (collagen assignment) |
| 952.6 | Symmetric stretching vibration of phosphate of $v_1$PO$_4^{3-}$ |
| 992.5 | C—O ribose, C—C |
| 999.3 | Carotenoids (absent in normal tissues), Phenylalanine, δ(ring) |
| 1034.3 | Proline (collagen assignment) |
| 1069.1 | Triglycerides (fatty acids) |
| 1095.9 | Phenylalanine (proteins) |
| 1113.6 | The strong C—O band of ribose (serves as marker band for RNA in solutions) |
| 1207.0 | Tryptophan & phenylalanine v (C—C$_6$H$_6$) mode, Stretching of C—N |
| 1238.4 | Amide III |
| 1253.5 | Amide III (protein band), second amide, Amide III (unordered), structural protein modes of tumors, amide III vibration mode of structural protein, triglycerides |
| 1277.2 | Cytosine |
| 1291.1 | Palmitic Acid, Acyl chains, Fatty acids |
| 1302.9 | CH$_3$/CH$_2$ twisting or bending mode of lipid/collagen, CH$_3$/CH$_2$ twisting, wagging &/or bending mode of collagens & lipids |
| 1335.8 | Graphene D-peak, G (DNA/RNA), CH deformation (proteins, and carbohydrates) |
| 1369.6 | CH$_3$/CH$_2$ twisting or bending mode of lipid/collagen |
| 1383.3 | CH$_3$ band |
| 1415.7 | A, G (ring breathing modes of DNA/RNA bases) |
| 1443.8 | Guanine, porphyrins, lipids, T, A, G (ring breathing modes of the DNA/RNA bases) |
| 1474.8 | Amide II (largely due to coupling of CN stretching & in-plane bending of N—H group, |
| 1506.6 | N=H bending, Cytosine |
| 1523.0 | Carotenoid |
| 1547.4 | Amide II |
| 1584.8 | Graphene G-peak, C=C olefinic stretch, Phenylalanine, hydroxyproline |
| 1620.9 | v (C=C), porphyrin |
| 1658.8 | Amide I (collagen) C=O stretching of collagen & elastin (protein assignment) |

TABLE 5

Assignments of the Raman peaks obtained from Raman spectrum of exosomes isolated from lung cancer cell H1975

| Raman shift (cm$^{-1}$) | Peak assignment |
| --- | --- |
| 640.0 | C—S stretching & C—C twisting of proteins-tyrosine |
| 682.4 | Ring Breathing modes in DNA bases, G (ring breathing modes in the DNA bases) |
| 734.1 | Phosphatidylserine |
| 814.6 | Proline, hydroxyproline, tyrosine |
| 847.4 | Monosaccharides (α-glucose, (C—O—C) skeletal mode |
| 899.7 | Monosacchardies(β-glucose), (C—O—C) skeletal mode, Disaccharide (maltose), (C—O—C) skeletal mode |
| 934.3 | C—C backbone (collagen assignment) |
| 970.9 | Phosphate monoester group of phosphorylated proteins & cellular nucleic acids |
| 1006.1 | Carotenoids (absent in normal tissues), Phenylalanine, δ(ring) |
| 1041.1 | carbohydrates peak for solution and solids, Proline (collagen assignment) |
| 1120.3 | The strong C—O band of ribose (serves as a marker band for RNA in solutions) |
| 1168.8 | Lipids, v(C═C), δ(COH) (lipid assignment), v(C—C), carotenoid |
| 1213.5 | Tryptophan & phenylalanine v(C—C$_6$H$_6$) mode, Stretching of C—N |
| 1260.0 | Amide III (protein band), second amide, Amide III vibration mode of structural proteins, CH$_2$ in-plane deformation (lipids), Triglycerides (fatty acids) |
| 1297.5 | Palmitic Acid, Acyl chains, Fatty acids |
| 1309.3 | CH$_3$/CH$_2$ twisting or bending mode of lipid/collagen |
| 1342.2 | Graphene D-peak, G (DNA/RNA), CH deformation (proteins, and carbohydrates) |
| 1422.0 | A, G (ring breathing modes of DNA/RNA bases) |
| 1481.0 | Amide II (largely due to coupling of CN stretching & in-plane bending of N—H group) |
| 1529.1 | Carotenoid (absent in normal tissues) |
| 1553.5 | Amide II |
| 1590.9 | Graphene G-peak, C═C olefinic stretch (protein assignment), Phenylalanine, hydroxyproline |
| 1605.9 | Cytosine (NH$_2$), Ring C—C stretch of phenyl (1), Phenylalanine, tyrosine, C═C (protein) |
| 1664.7 | Amide I (collagen), C═C (of lipids in normal tissue; not that of amide I) Amide I (C═O stretching mode of proteins α-helix conformation)/C═C lipids, C═O stretching of collagen & elastin (protein assignment) |

Each specimen 120 showed uniquely identifiable spectral characteristics manifested primarily in the relative peak intensities. For example, the relative intensity of nucleic acid bands was substantially higher in the human and bovine serum-derived exosomes compared to those from the cancer cell-lines. In contrast, the relative intensity of the lipid bands was discernibly higher in the cancer cell-derived exosomes. Previous reports suggested that excessive lipids and cholesterol were stored in lipid droplets (LDs) in cancer cells. Thus, high content of LDs and cholesterol in tumors are now considered hallmarks of cancer aggressiveness. Findings that exosomes 120 from the two cancer cells contained substantially more lipids than exosomes from normal human or animal serum are consistent with these reports. Although it is known that the serum contains high amounts of free circulating nucleic acids and different hypotheses have been put forward to address this, e.g., an unequal distribution of DNA during separation from whole blood, differences in exosomal nucleic acid content between normal and cancer cells have not been reported.

To quantify the differences and similarities in the spectra described above, principle component analysis (PCA) (FIG. 13E) was applied, e.g., as described to ~50 Raman spectra from each sample. The results clearly show that the exosomes 120 from the four different sources: FBS (FIG. 10), serum of healthy individuals (FIGS. 13A, 13B), and cell lines HCC827 (FIG. 13C) and H1975 (FIG. 13D) clustered into distinguishable groups with <5% overlap between the different groups on average at a sensitivity of >84%. The Raman spectra of exosomes from two healthy individuals largely overlapped, indicating that they shared many common features. These findings show that SIM analysis of exosomes from different bodily fluids has the potential of becoming a disease biomarker without the need of biological labels.

A side-by-side comparison of isolation of exosomes using a combination of ultracentrifugation and ultrafiltration were performed, with a preparation of a heterogeneous mixture of extra-cellular vesicles by salting-out using a commercial kit. Prior to Raman mapping, successful isolation of exosomes was confirmed by combinations of traditional experimental techniques, including DLS, TRPS, TEM and western blot with exosomal marker proteins. To further ensure that each measurement represented a single exosome, we correlated between Raman mapping and scanning electron microscopic (SEM) examination of individual vesicles on the substrate surface.

The methods and platform can be used for the unambiguous identification of exosomes 120 from commonly achievable biological species. Comparing to all previously reported approaches, detection of exosomes 120 according to embodiments was verified by the rigorous correlative study using several complementary techniques including DLS, TRPS, TEM, Western blot, and SEM with Raman mapping. In addition, the "finger-print" capability has been demonstrated in the unambiguous distinction of exosomes from four different sources. Combined with PCA, embodiments have been shown to cluster the exosomes into distinguishable groups with <5% overlap among different groups at a sensitivity of >84%, which to our knowledge is higher than what has been reported to date. With characteristics of being inherently single-exosome-based and label-free, the embodiments can identify disease-specific biomarkers for early-stage disease diagnosis as well as serve as a useful research tool for deepening the understanding of the role of exosomes 120 in normal physiology and disease.

Experimental Methods

Fabrication of Au Nano-Pyramid Hybrid SERS Substrate

The Hybrid SERS substrate 130 used in the present study has been described previously. Briefly, a template using a single layer of self-assembled polystyrene balls was generated. The near-hexagonal pitch periodicity was then transferred to a $SiO_2$ mask over a Si (001) wafer via plasma etching. These two methods produce nanometer-scale, 2-dimensional features of poorly defined shapes. An additional step of anisotropic etching of Si to transfer the fuzzy 2-D features into well-defined 3-D inverted pyramids bounded by {111} facets on a (001) oriented Si wafer. Geometrical hindrance was also employed during thermal oxidation of Si to fine-tune the sharpness of the apex of the inverted pyramids. Two-hundred-nm thick Au films then were deposited over the pitted surface, bonded to a handle substrate using epoxy, and then lifted off the surface thereby completing the nano-casting process. Because of the way the substrate was fabricated, the Au-tipped surface had the unique features of in-plane anisotropy and wafer-scale coherency with the precise orientation and shape of individual pyramids.

Preparation and Transfer of Graphene

Twenty-five μm thick copper foil was cut into a 2×2-inch square and placed at the center of a quartz chemical vapor deposition (CVD) tube of 15-cm diameter. It served the purpose of catalyst during CVD growth. The furnace was heated up to ~1,060° C. under $H_2$ flow at 1 Torr total pressure. After 30-minute annealing, growth commenced under 20 Torr total pressure with a flow of $CH_4$ (~20 standard cubic centimeter per minute (sccm)) and $H_2$ (~1000 sccm) for 15 min. The chamber was cooled down to room temperature over 10 h. A ~500-nm poly(methylmethacrylate) (PMMA) layer was spin-coated on the graphene-covered Cu foil to provide mechanical support to the monolayer of graphene during the subsequent Cu etching step. The Cu foil was removed in an etching solution of $FeCl_3$:$H_2O$ (1:5 vol. %). Then the floating PMMA-graphene structure was transferred onto the surface of de-ionized water and the sample was transferred onto a target substrate. In the final, step the PMMA supporting layer was removed by acetone.

Raman Spectroscopy

Raman spectra were recorded using a Renishaw inVia Raman spectrometer under ambient conditions (20° C. and 1 atm). WiRe 4.2 software was used to control the whole system. The laser excitation wavelength was 785 nm. The power of the laser was kept at 5 mW to avoid sample overheating. The diameter of the laser spot was 1.83 μm. The Raman measurements first were calibrated by the Si Raman mode at 520 $cm^{-1}$. Two μL of the exosome solutions were applied to the hybrid platform surface and allowed to air-dry before the measurement. The acquisition time was 1 second. For coarse Raman mapping, Raman spectra across a 10×10-pixel area were collected with a step length of 2 μm. For fine Raman mapping, Raman spectra across a 10×10-pixel area were collected with a step length of 0.1 μm.

Exosome Isolation

FBS was procured from Invitrogen, USA. Extra-cellular vesicles from FBS were isolated using an ExoQuick® kit (System Biosciences, USA) following manufacturer's instructions.

For human serum, peripheral blood was collected from two healthy volunteers by venipuncture using a BD Vacutainer push-button blood-collection kit and left to coagulate in silicone-coated serum-collection tubes for 20 min at room temperature. After centrifugation at 1,500 g for 15 min, serum was collected and either processed immediately or stored at −80° C.

Human lung cancer cell lines, HCC827 and H1975 were obtained from ATCC and cultured in 75 $cm^2$ tissue culture flasks. Cells were cultured in exosome-free conditioned medium, pre-cleared of exosomes and protein aggregates prior to use for cell culture by ultracentrifugation. Supernatants were collected 48-72 h after changing the medium for exosome isolation.

After thawing quickly in a 37-° C. water bath, protease and phosphatase inhibitors were added and the serum from either source was diluted ten times with chilled PBS. Cell culture supernatants or diluted sera were centrifuged at 2,000 g and 4° C. for 20 min and then further centrifuged at 12,000 g and 4° C. for 45 min to remove small debris particles. The supernatants were filtered using 0.22-μm pore filters, followed by ultracentrifugation (Model, L8-M70, Beckman Coulter, USA) at 110,000 g and 4° C. for 2 h. The resulting pellets were re-suspended in chilled PBS and ultracentrifuged again at 110,000 g and 4° C. for 70 min. The final pellet of exosomes was re-suspended, in 50-100 μL PBS for TRPS measurement, in a 2% paraformaldehyde (PFA) solution in Milli-Q water for SERS and TEM experiments, or lysed in RIPA buffer, aliquoted, and stored at −80° C. for Western blot analysis.

Dynamic Light Scattering

The size distribution (diameter) of exosomes and Extra-cellular vesicles was determined using a Zetasizer Nano instrument (Malvern Instruments Ltd, Worcestershire, UK). After isolation, the exosome pellet was reconstituted in 100 μL of filtered PBS. Fifty μL of purified exosomes were diluted in 1,450 μL of filtered PBS and gently vortexed for 30 s to avoid aggregation. The whole volume was quickly transferred into a disposable cuvette and allowed to equilibrate for 30 s at 25° C. A 20-mW He—Ne laser operating at 632 nm was used at an angle of 173°. The dispersant refractive index value used was 1.37. The size of the observed vesicle populations was determined by Z-average and polydispersity index (PdI). Three independent measurements of 14 counts each were performed per sample and average values are presented.

Tunable Resistive Pulse Sensing (TRPS)

TRPS measurements were performed using a qNano instrument (Izon Science Ltd, Christchurch, New Zealand). All measurements were calibrated with appropriately diluted CPC200 polystyrene beads (Izon Science, UK). A polyurethane nanopore (NP150, Izon Science, UK) was used, and was axially stretched to 48 mm. Forty μL samples diluted in PBS were used for measurement. Data were processed and analyzed using the Izon Control Suite software v3.3.2.2001 (Izon Science, UK).

Transmission Electron Microscopy (TEM)

For TEM observation of isolated exosomes, pellets obtained after ultracentrifugation at 110,000×g were re-suspended in fixative (2% paraformaldehyde (PFA) in Milli-Q water). Formvar carbon-coated grids (FCF400-CU, Electron Microscopy Sciences) were glow-discharged on a Pelco easiGlow instrument (Ted Pella Inc., USA) for 2 min.

Small drops of PFA-fixed exosomes then were placed on the grids and incubated for 20 min. The grids were washed by floating them upside down on drops of Milli-Q water. The exosomes were further fixed in 1% glutaraldehyde for 5 min and the stained successively in freshly prepared 2% uranyl acetate and 2% methylcellulose/0.4% uranyl acetate. Grids were imaged using a FEI Technai T20 transmission electron microscope equipped with a thermionic tungsten filament and operated at an acceleration voltage of 200 kV. Images were taken using a cooled slow-scan CCD camera at a magnification of 80,000×.

Scanning Electron Microscopy (SEM)

SEM imaging was performed using a Nova 230 Nano scanning electron microscope. The accelerating voltage was 10 kV. The samples were viewed at an electron spot size of 3. The detector mode was "through-the-lens" (TLD) secondary electron (SE) detector. The SERS substrate was mounted on the stage by double-coated carbon conductive tape. Images were taken at a magnification of 35,000× or 50,000×.

Western Blot Analysis

Protein concentration was calculated using a BCA protein assay kit (ThermoFisher Scientific, USA). Proteins were mixed with NuPAGE LDS Sample Buffer containing 5% β-mercaptoethanol and heated at 90° C. for 10 min. Twenty μg of protein extracts were fractionated on 4-12% NuPAGE Bis-Tris gels and electro-transferred onto nitrocellulose membranes (ThermoFisher Scientific, USA). The membranes were then blocked with 5% skim milk in tris-buffered saline (TBS)-0.1% Tween-20 (TBST) for 1 h at room temperature and then were incubated overnight at 4° C. with appropriate primary antibodies at 1:2,000 dilution in blocking solution. After three washes with TBST for 10 min each, horseradish peroxidase-conjugated secondary antibodies (ThermoFisher Scientific) at 1:5,000 dilution in blocking solution were added and the membranes were incubated for 1 h at room temperature. SuperSignal West Femto maximum sensitivity substrate (Thermo Fisher Scientific, USA) was added and protein bands were visualized using a Gel-Doc apparatus (Syngene, USA).

Statistical and Principle Component Analyses

Data were analyzed by 2-way ANOVA using Origin 8.0. Results were considered significant at $p<0.05$. Principal component analysis (PCA) is a statistical procedure that uses an orthogonal transformation to convert a set of observations of possibly correlated variables into a set of values of linearly uncorrelated variables called principal components (or sometimes, principal modes of variation). In our study, the correlated variables were the vectors including Raman shift and the related Raman intensity of each Raman spectrum. This orthogonal transformation was defined so that the first principal component (PC1) had the largest possible variance (i.e., accounted for as much of the variability in the data as possible), and each succeeding component (PC2, PC3, etc.) in turn had the highest variance possible under the constraint that it is orthogonal to the preceding components. The results were presented using PC1 and PC2 (FIG. 10E). The procedure was as follows: First, the background of the Raman spectrum was subtracted and the data were saved in txt format. Then, PCA analysis was performed using an in-house coded program running on a Python compiler. Sixteen vectors were chosen along the Raman shift axis (847, 854, 1,043, 1,163, 1,181, 1,202, 1,213, 1,255, 1,269, 1,309, 1,374, 1,384, 1,421, 1,429, 1,482, and 1,506 $cm^{-1}$) for fully regenerating the original spectra. The data were visualized using an in-house written program in R Studio.

Referring now to FIGS. 14A-20B, another example of how embodiments may be implemented involves identifying or characterizing biological specimens 120 based on a relative abundance of proteins or amino acids in a biological element of the biological specimen, e.g., in a biological element in the form of an exosome as described above.

Figure 14A:
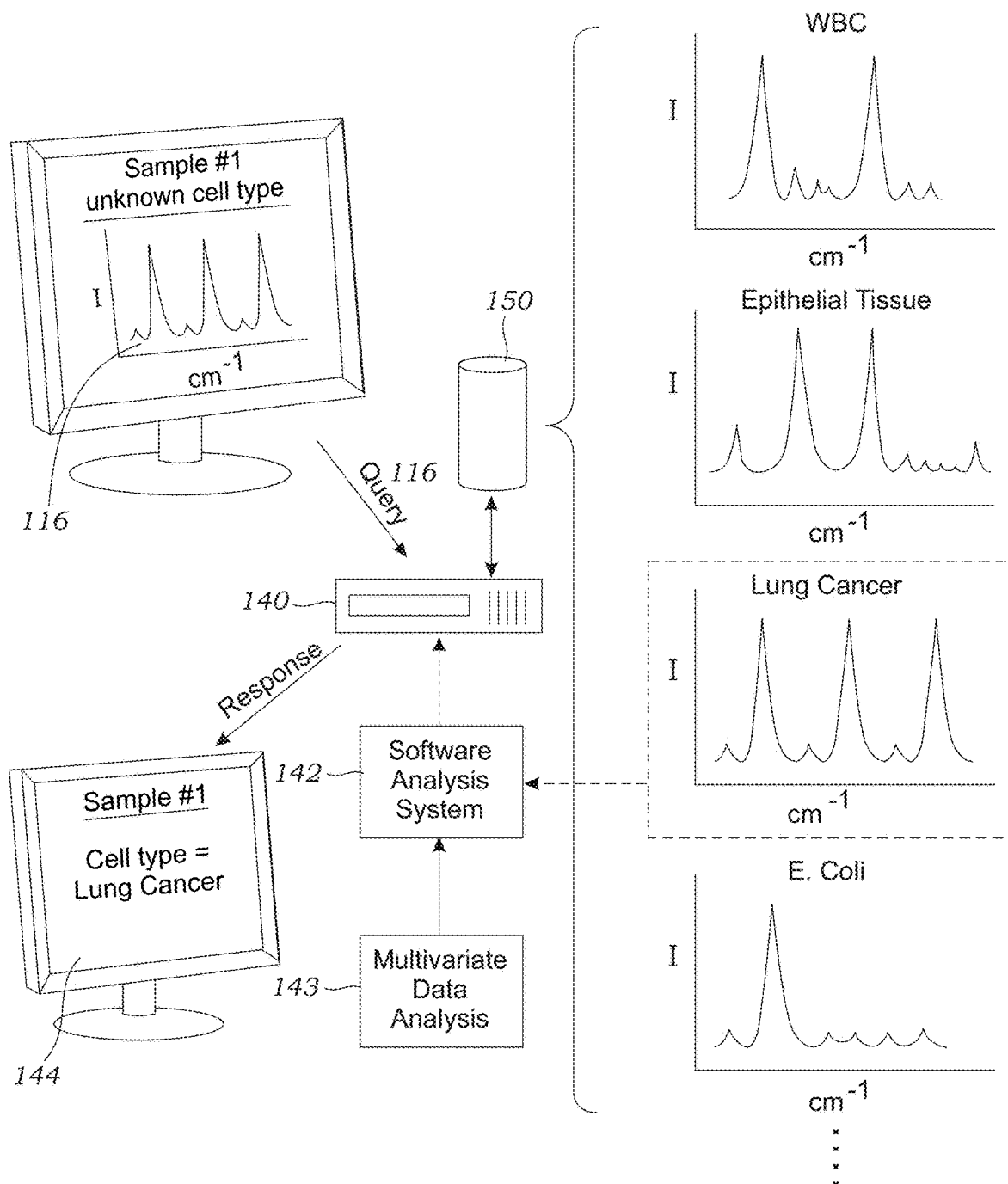
FIG. 14A illustrates a method of using the system according to one embodiment to classify or detect the type of unknown cell using the CMAP signature.
Figure 14B:
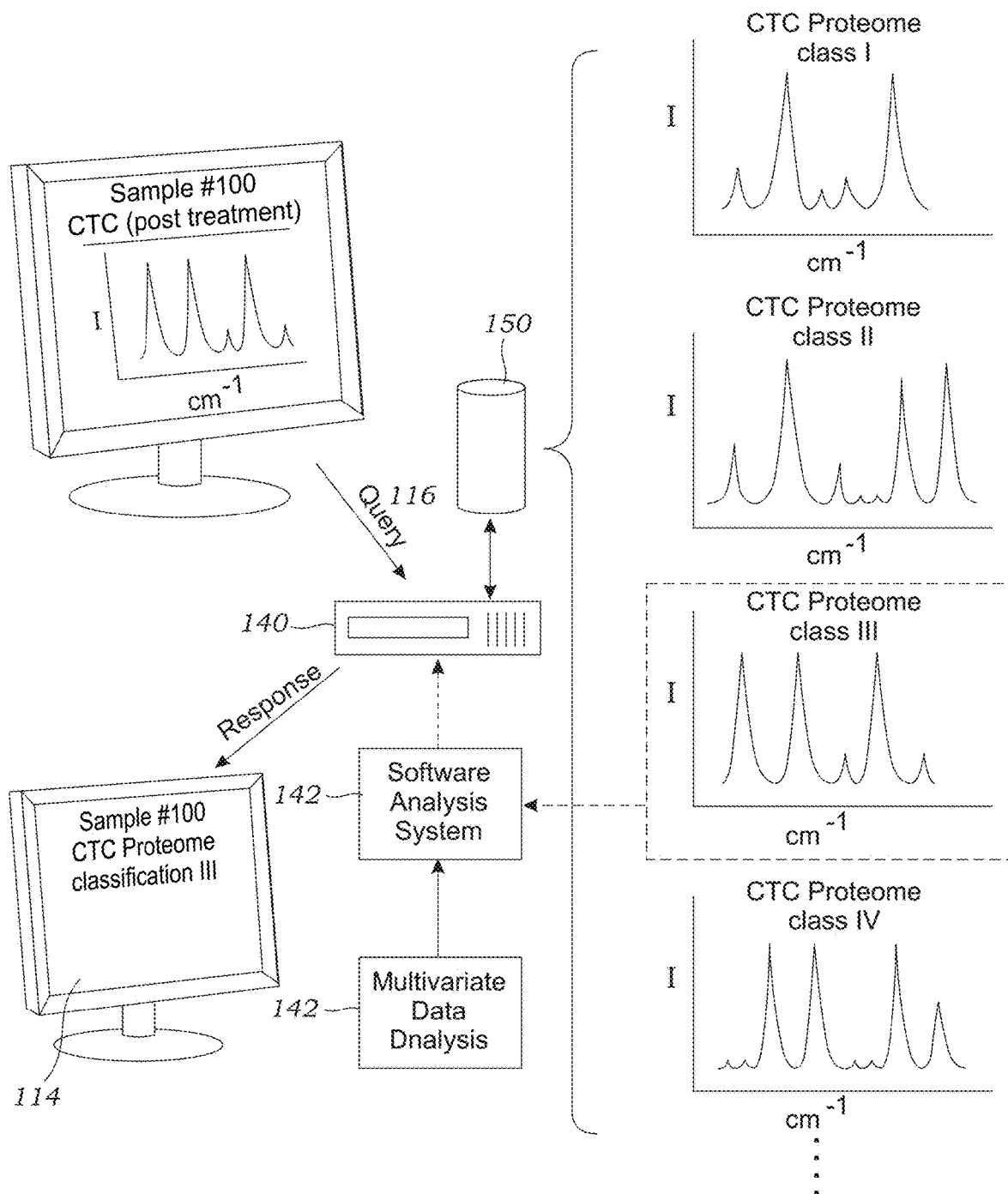
FIG. 14B illustrates a method of using the system according to one embodiment to analyze the state of the proteome of a cell after exposure of the cell to a drug or other therapeutic compound using the CMAP signature.
Figure 15:
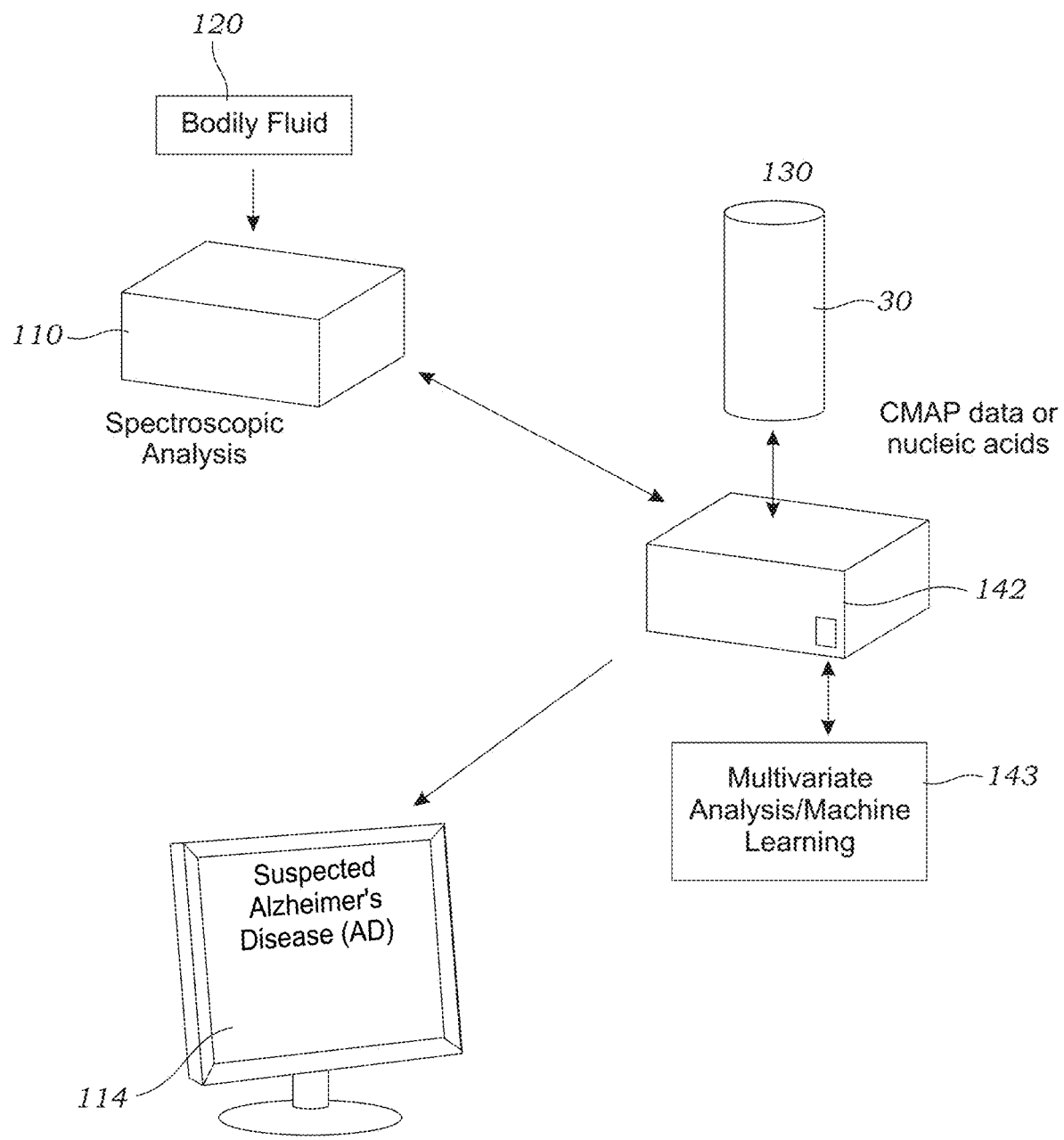
FIG. 15 illustrates a method of using the system according to another embodiment to detect the health/disease state or condition of a subject using a bodily fluid sample.

Referring to FIGS. 14A-B and 15, specimen characterization or identification system 700 includes spectrometer 110, a substrate 130 on which biological specimen 120 has been loaded, computing system 140 and database 150 components, various aspects of which are described above and not repeated. In the illustrated embodiment, the database 150 includes a library 152 of vibrational spectra or Raman shift data 154 of various cell types that may be indicative of a health condition or status or disease, e.g., WBC, epithelial tissue, lung cancer, E. coli, and other cell types, e.g., for Alzheimer's disease.

FIG. 14A illustrates the operation of the system 1400 according to one embodiment where a biological specimen 120 containing an unknown cell type is subject to spectrometry (e.g., SERS) to determine the CMAP "fingerprint" of the unknown cell type and then identify a match of that fingerprint in database 150 to determine the identity of the cell type. While SERS spectrometry is illustrated, it should be understood that other spectrometry methods can be employed (e.g., mass spectrometry, FTIR, etc.).

In this embodiment, SERS testing of the unknown biological specimen 120 is performed to generate SERS spectra that includes CMAP data. Using the computing system 140, the database 150 is queried to find the cell type that most closely matches the CMAP data of the unknown sample. The analysis program 142 executing multivariate analysis of the CMAP data is used to classify unknown cell types into known cell types. In this embodiment, the unknown cell type is identified by the analysis program 142 as a lung cancer cell which can then be reported to the user.

FIG. 14B illustrates another embodiment used to characterize the proteome of a known cell type (in this example a CTC sample). For example, CTC cells that are exposed to a drug (i.e., post treatment) can then be analyzed again using SERS to see how the proteome has changed. In this example, the CMAP of the post-treated cell leads to proteome classification III. These types of classifications may be used to determine the efficacy of treatment for a particular patient. For example, cellular monitoring of the proteome of cells vis-à-vis their CMAP signature can be used to determine if their drug treatment regime is working or if alternative drug therapies need to be tried. For example, using CMAP analysis, a single type of cancer cell that is treated with different types or even amounts of chemo drugs can be distinguished.

Referring to FIG. 15, another embodiment is illustrated and used characterize a bodily fluids specimen 120 obtained from a mammalian subject. Bodily fluids may include by way of example blood, sweat, cerebrospinal fluid (CSF), urine, semen, saliva, etc. as noted above. The bodily fluid is subjected to spectroscopic analysis by spectrometer 110, and testing of the unknown sample is performed to generate spectra or other data that includes CMAP data. Using the computing system 140, database 150 is queried to find the health or disease state of the subject that most closely matches the CMAP data of the unknown biological specimen 120. This may include a disease, disease precursor, or infectious state of a subject (e.g., viral infection, bacterial infection, fungal infection). Multivariate analysis 142 of the CMAP data may be used to generate or classify the health or disease state of the subject. In this example, the software analysis program 142, based on the analysis of CMAP data of the bodily fluid, identifies the subject as being a candidate for or has Alzheimer's disease (AD).

In current detection techniques a single protein or peptide type is used as a biomarker for the identification of cell type or cell state. In contrast, the current inventive method and system does not look to the proverbial "needle in the haystack" but instead looks and the unique composition of the most common (and not-so-unique) biomolecules that are found in cells or cell structures such as exosomes or bodily fluids. With embodiments of the invention, the uniqueness of CMAP of cells (and cell structures) as well as that of bodily fluids including blood, sweat, cerebrospinal fluid (CSF), urine, semen, saliva, etc. are used as biomarkers for disease diagnosis and prognosis. The experimental technique used for extracting information of CMAP can be any technique capable of determining the presence of these proteins and DNA, RNA and/or their fragments. CMAP is a manifestation of the relative population of proteins often being common to many different cell types or bodily fluids. It is their relative abundance being unique thus can be used as biomarkers. This is in clear contrast to the conventional biomarkers that rely on one particular protein type.

As a new biomarker discovery platform, CMAP signatures have the distinctive advantage of being independent of the existence of unique protein markers or being rendered ineffective because of the disappearance of those unique protein markers due, e.g. to cell mutation. In one preferred embodiment, the biomolecules that are analyzed are proteins or the amino acids that makeup the proteins. In some alternative embodiments, the biomolecules may include nucleic acid sequences (e.g., DNA and RNA).

Experimental

Figure 16A:
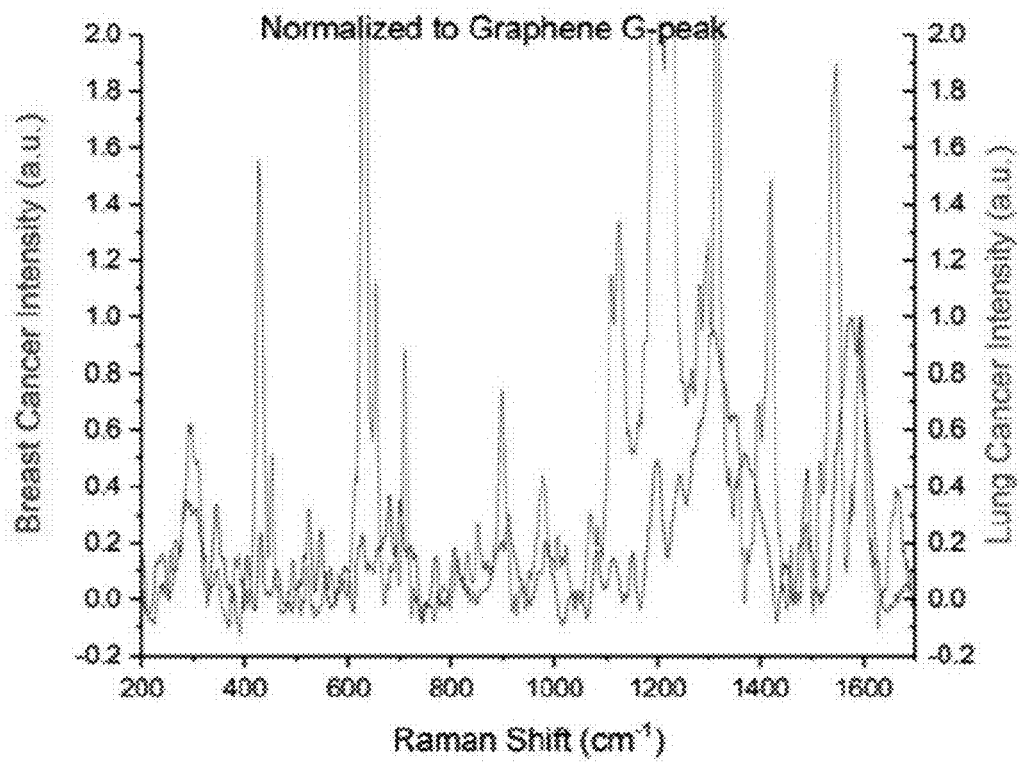
FIG. 16A illustrates the Raman spectra of both breast cancer cells (MCF7) and lung cancer cells (A549)
Figure 16B:
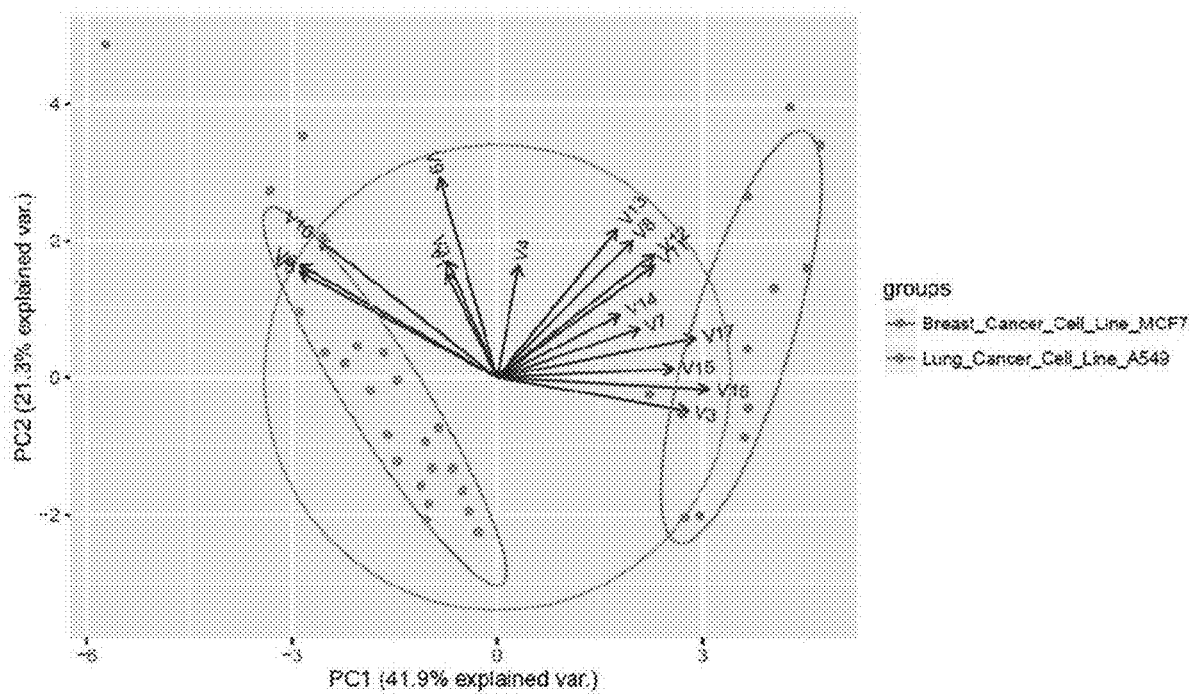
FIG. 16B illustrates the PCA result showing clear distinction in the clustering of these two cell lines into two distinct groupings.

FIG. 16A illustrates the Raman spectra of both breast cancer cells (MCF7) and lung cancer cells (A549). The cells were tested on a SERS platform that used a substrate 130 that included plasmonic nanofeatures 132 that are formed thereon and covered by graphene. The distinction of cell lines is performed with 100% sensitivity and 100% specificity. FIG. 16B illustrates the PCA result showing clear distinction in the clustering of these two cell lines into two distinct groupings.

Figure 17A:
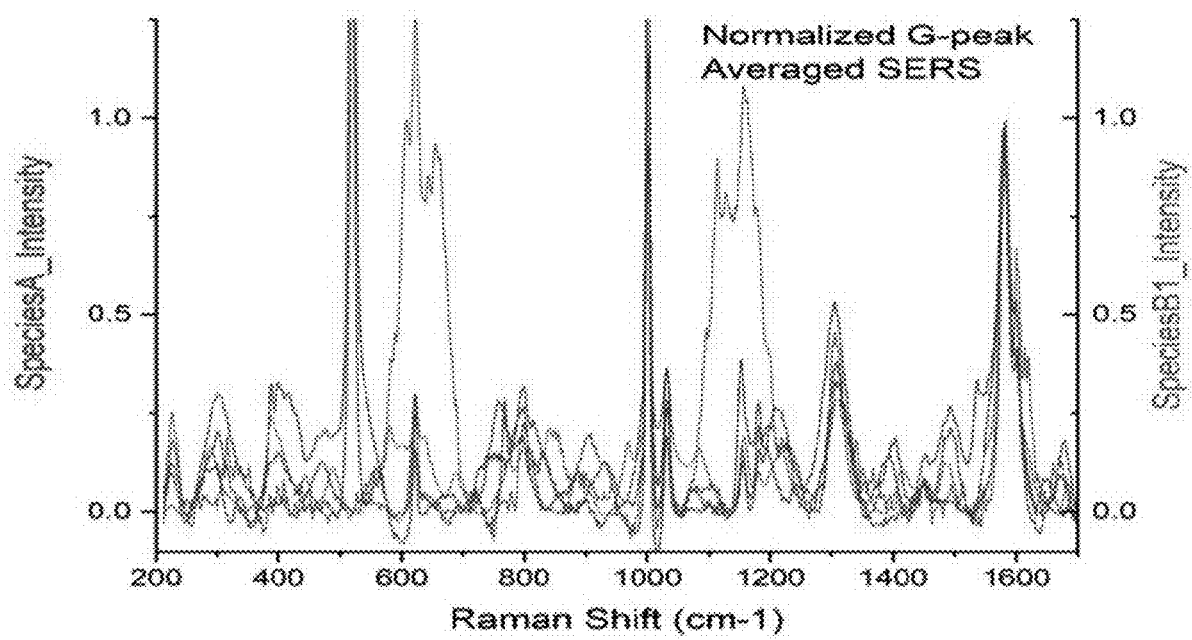
FIG. 17A illustrates the Raman spectra of fungi (*Cryptococcus*) of the same genus but different species.
Figure 17B:
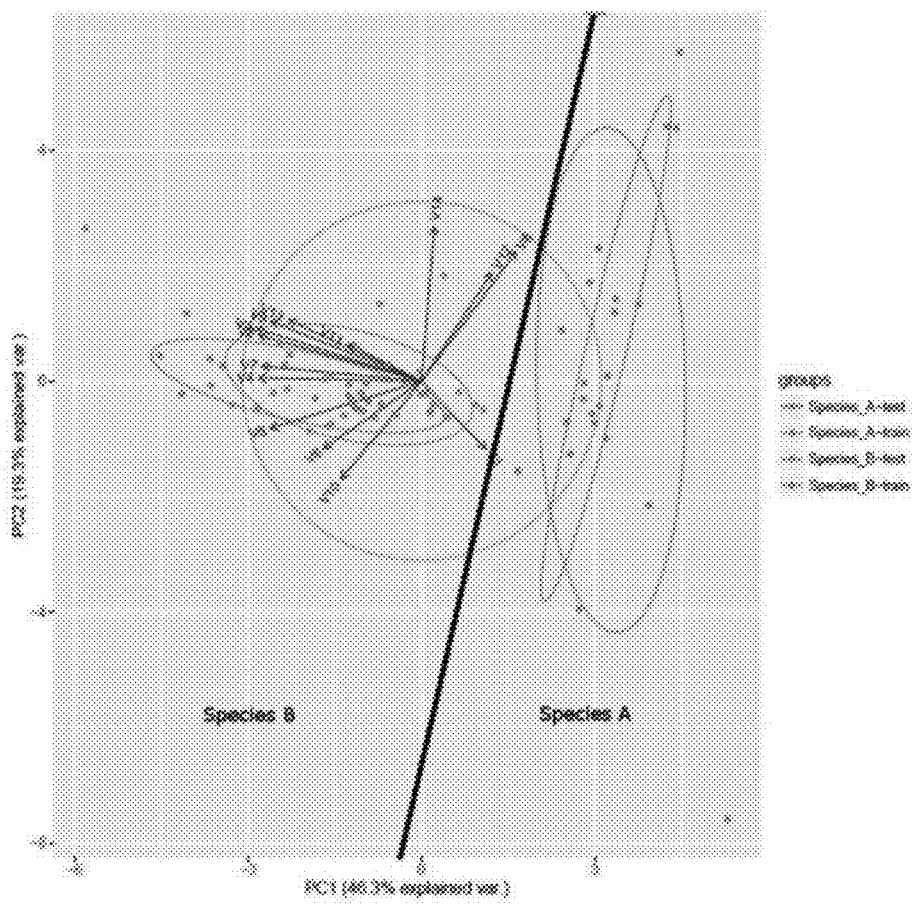
FIG. 17B illustrates the PCA result showing clear distinction in the clustering of these two fungi species into two distinct groupings.

Referring to FIG. 17A, the Raman spectra of fungi (*Cryptococcus*) of the same genus but different species. The fungi were tested on a SERS platform that used a substrate that included plasmonic nanofeatures that are formed thereon and covered by graphene. The distinction of species of fungi is performed with 100% sensitivity and 100% specificity. FIG. 17B illustrates the PCA result showing clear distinction in the clustering of these two fungi species into two distinct groupings.

Figure 18A:
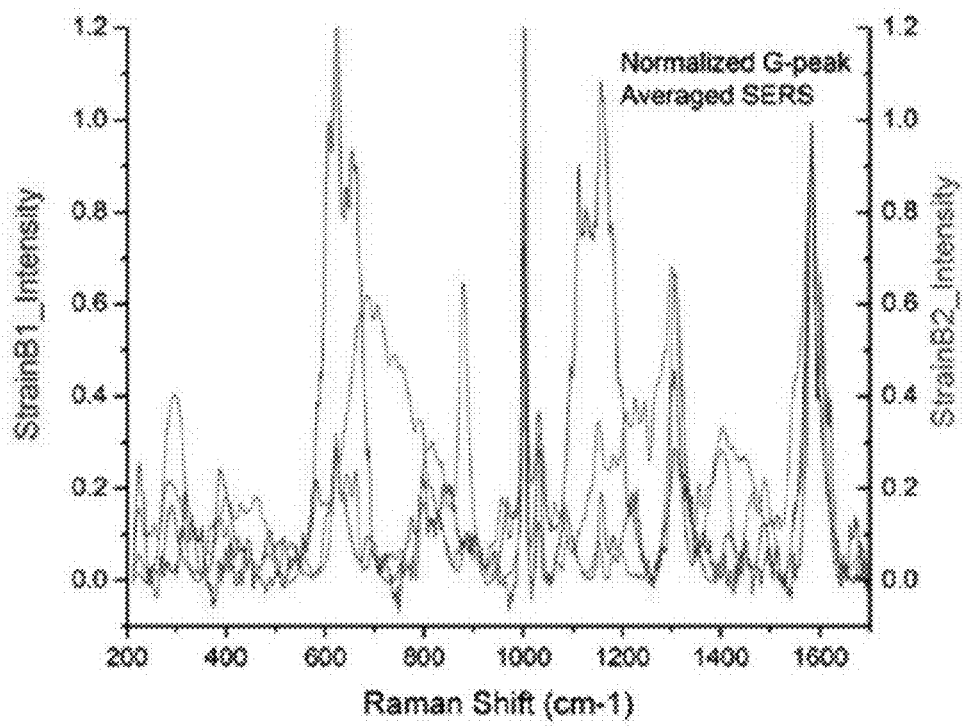
FIG. 18A illustrates the Raman spectra of fungi of the same genus (*Cryptococcus*) and species (*gattii*) but different strains: ST7(A) and ST106(B)
Figure 18B:
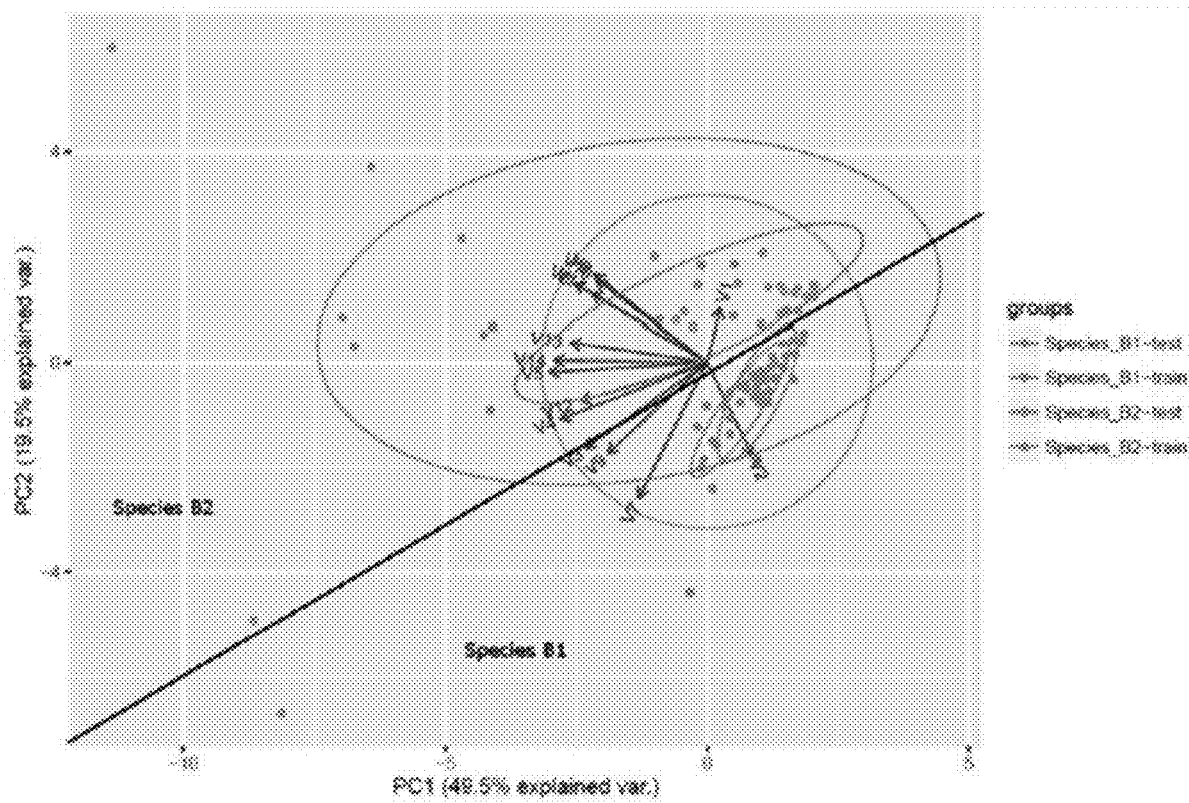
FIG. 18B illustrates the PCA results showing separation showing strain B2 generally above the angled line while strain B1 generally below the angled line.

FIG. 18A illustrates the Raman spectra of fungi of the same genus (*Cryptococcus*) and species (*gattii*) but different strains: ST7(B1) and ST106(B2). The fungi strains were tested on a SERS platform that used a substrate that included plasmonic nanofeatures that are formed thereon and covered by graphene. The distinction of strains of fungi is performed with 100% sensitivity and 97% specificity. FIG. 18B illustrates the PCA results showing separation showing strain B2 generally above the angled line while strain B1 generally below the angled line.

Figure 19A:
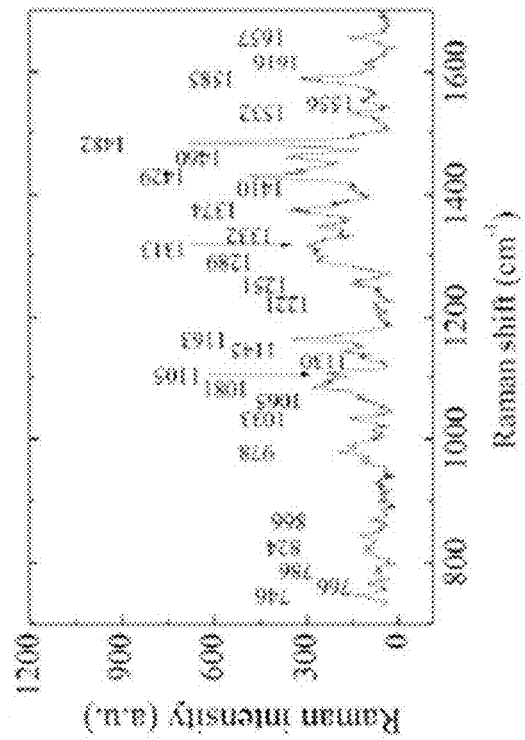
FIG. 19A illustrates the Raman spectra of exosomes of different origin based on their CMAP.
Figure 19B:
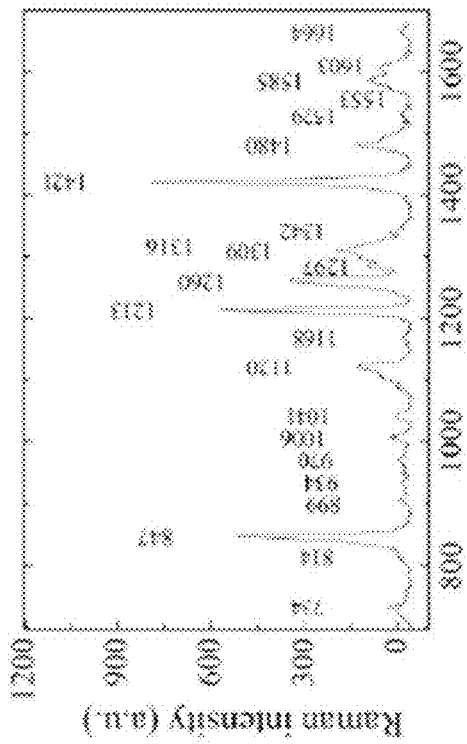
Figure 19C:
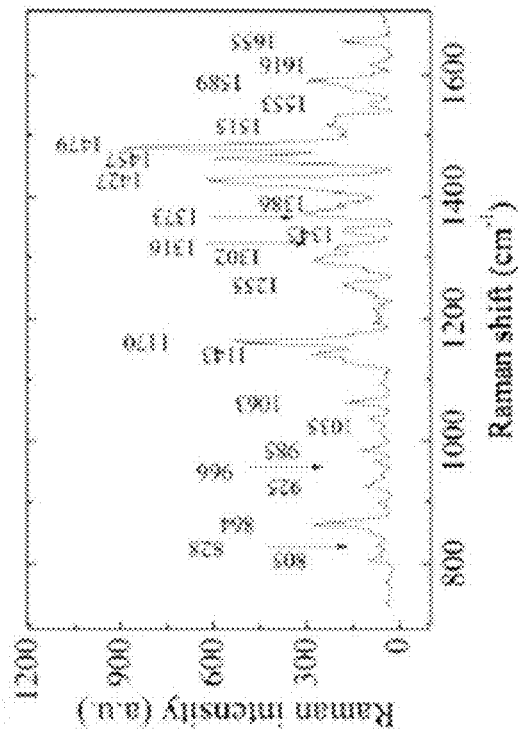
Figure 19D:
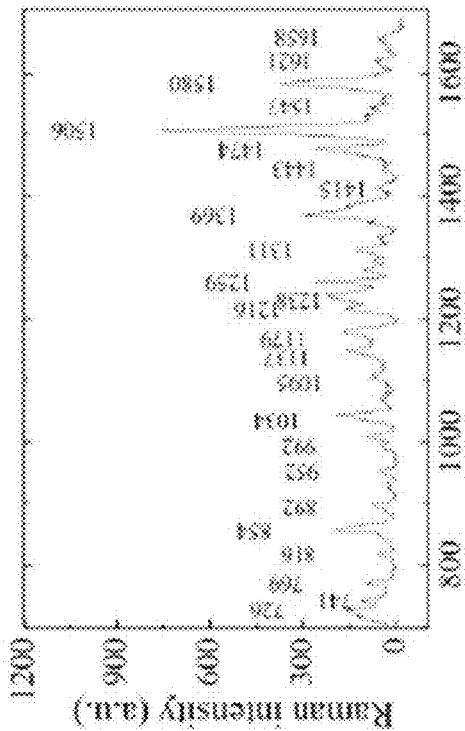
Figure 19E:
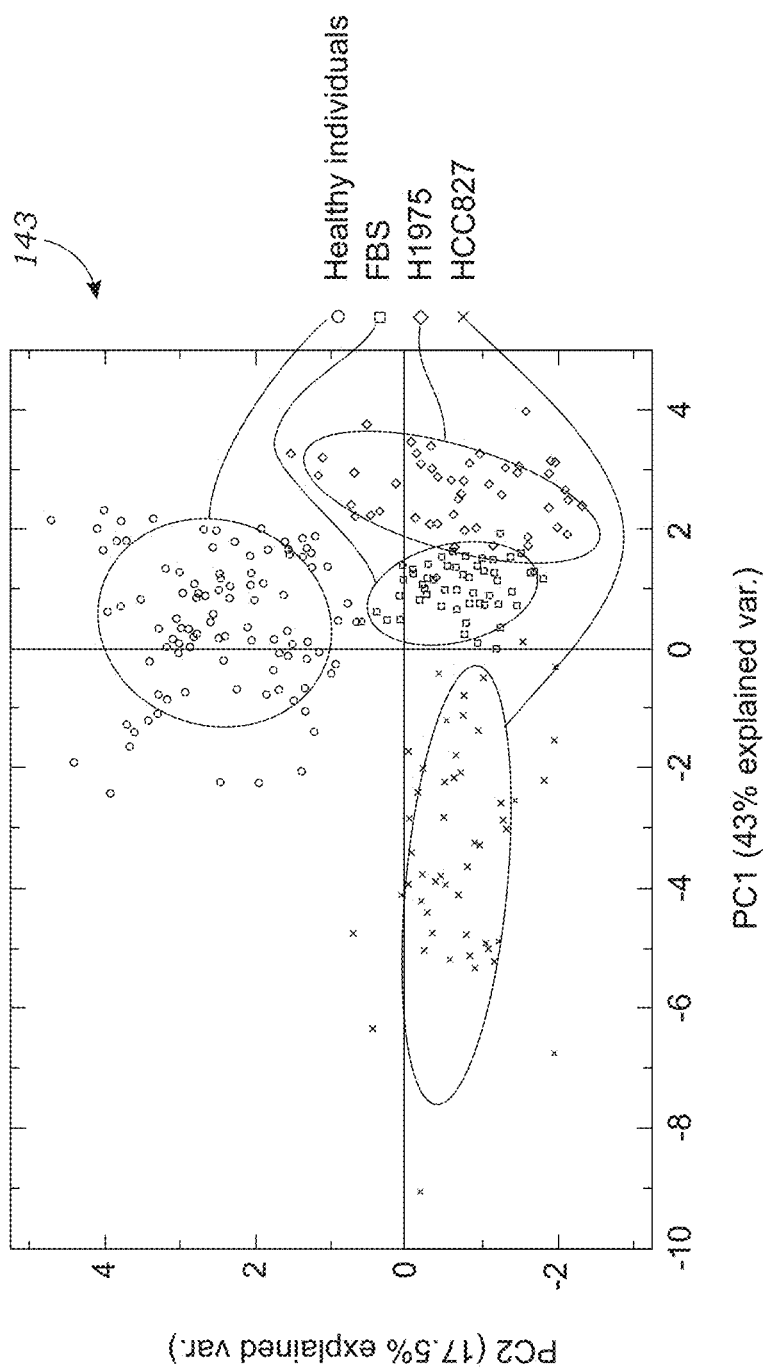
FIG. 19E shows the PCA result with lung cancer cells being clearly distinguishable though healthy cells from individuals are indistinguishable.

FIG. 19A illustrates the Raman spectra of exosomes of different origin based on their CMAP. The exosomes were tested on a SERS platform that used a substrate that included plasmonic nanofeatures that are formed thereon and covered by graphene. For human serum, peripheral blood was collected from two healthy volunteers by venipuncture using a BD Vacutainer push-button blood-collection kit and left to coagulate in silicone-coated serum-collection tubes for 20 min at room temperature. After centrifugation at 1,500 g for 15 min, serum was collected and either processed immediately or stored at −80° C.

Human lung cancer cell lines, HCC827 and H1975 were obtained from ATCC and cultured in 75 cm² tissue culture flasks. Cells were cultured in exosome-free conditioned medium, pre-cleared of exosomes and protein aggregates prior to use for cell culture by ultracentrifugation. Supernatants were collected 48-72 h after changing the medium for exosome isolation. After thawing quickly in a 37° C. water bath, protease and phosphatase inhibitors were added and the serum from either source was diluted ten times with chilled PBS. Cell culture supernatants or diluted sera were centrifuged at 2,000 g and 4° C. for 20 min and then further centrifuged at 12,000 g and 4° C. for 45 min to remove small debris particles. The supernatants were filtered using 0.22-μm pore filters, followed by ultracentrifugation (Model, L8-M70, Beckman Coulter, USA) at 110,000 g and 4° C. for 2 h The resulting pellets were re-suspended in chilled PBS and ultracentrifuged again at 110,000 g and 4° C. for 70 min. The final pellet of exosomes was re-suspended, in 50-100 μL PBS for TRPS measurement, in a 2% paraformaldehyde (PFA) solution in Milli-Q water for SERS and TEM experiments, or lysed in RIPA buffer, aliquoted, and stored at −80° C. for Western blot analysis.

Figure 9B:
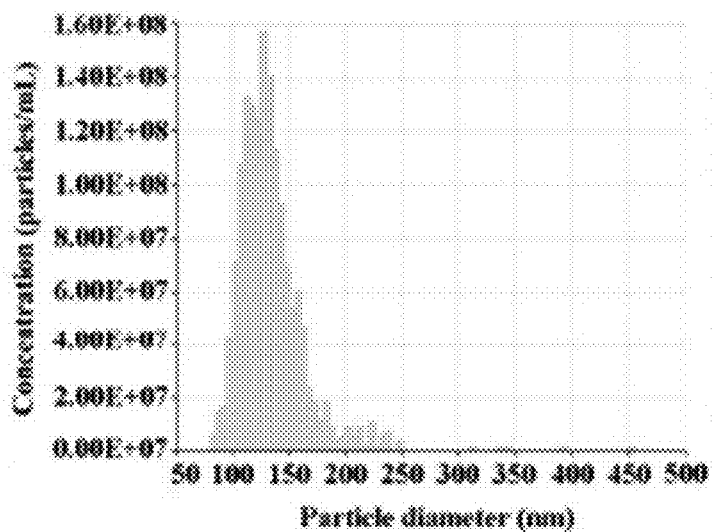
FIG. 9B illustrates TRPS analysis of exosomes.
Figure 9C:
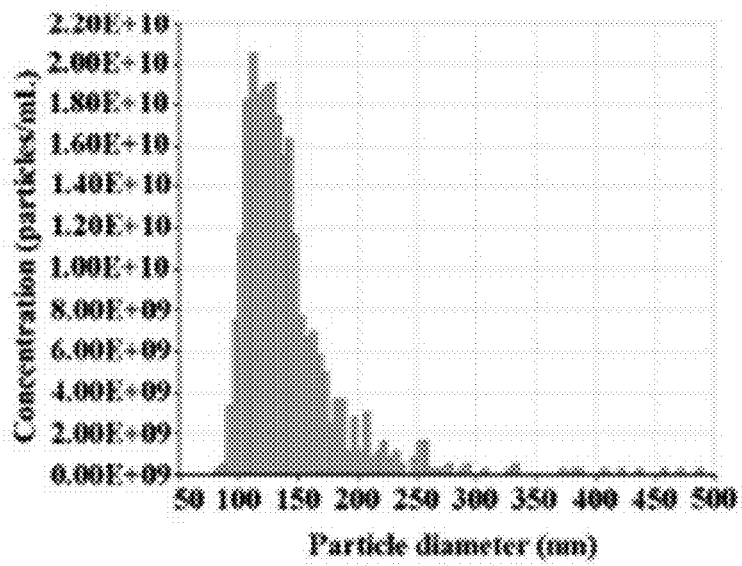
FIG. 9C illustrates TRPS analysis of EVs.
Figures 9D, 9E, 9F:
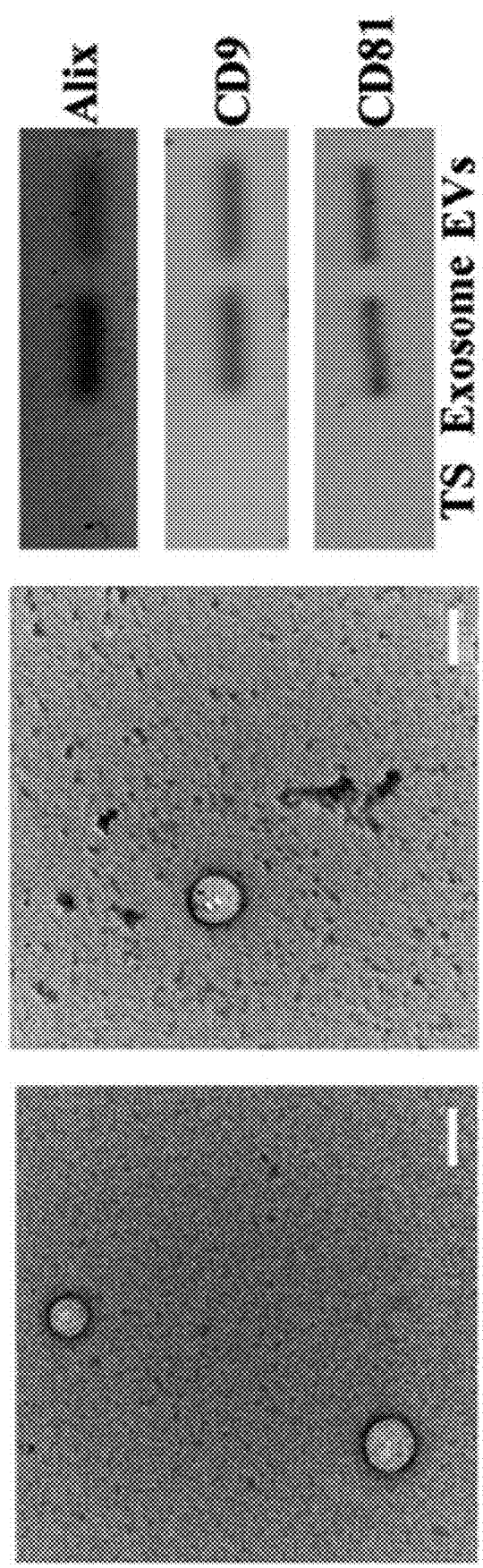
FIGS. 9D and 9E illustrate representative TEM image of exosomes (FIG. 9D) and EVs (FIG. 9E) at 80,000× magnification. The scale bars in both panels represent 200 nm.
FIG. 9F illustrates Western blot analysis with the exosomal markers alix, CD9, and CD81. TS: total serum.
Figure 9G:
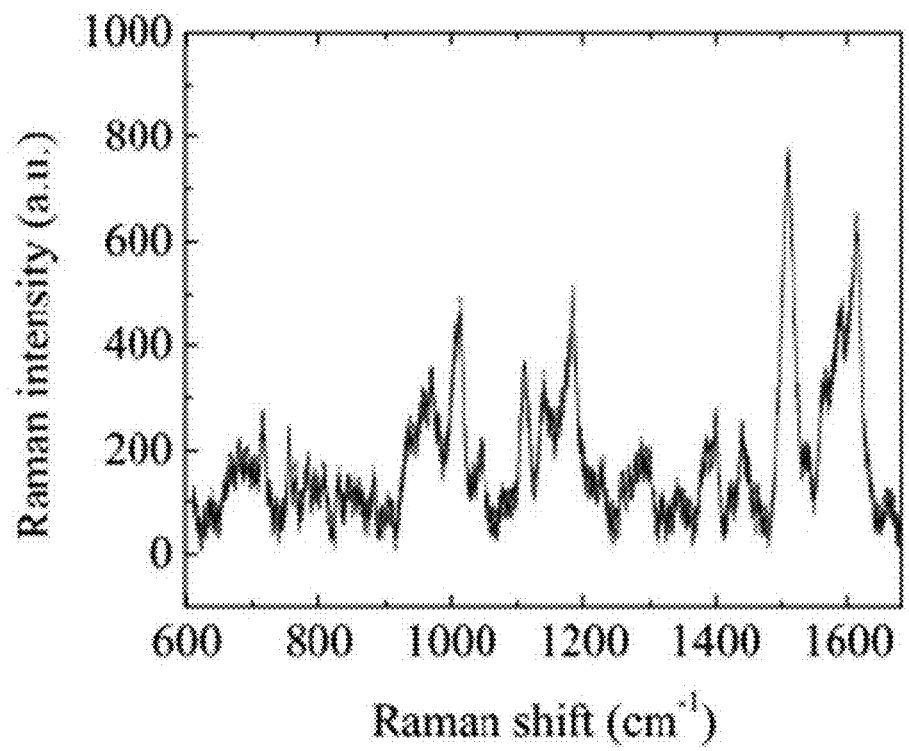
FIG. 9G illustrates Raman spectra of exosomes isolated from a Fetal Bovine Syndrome (FBS) specimen using ultracentrifugation/filtration.
Figure 9H:
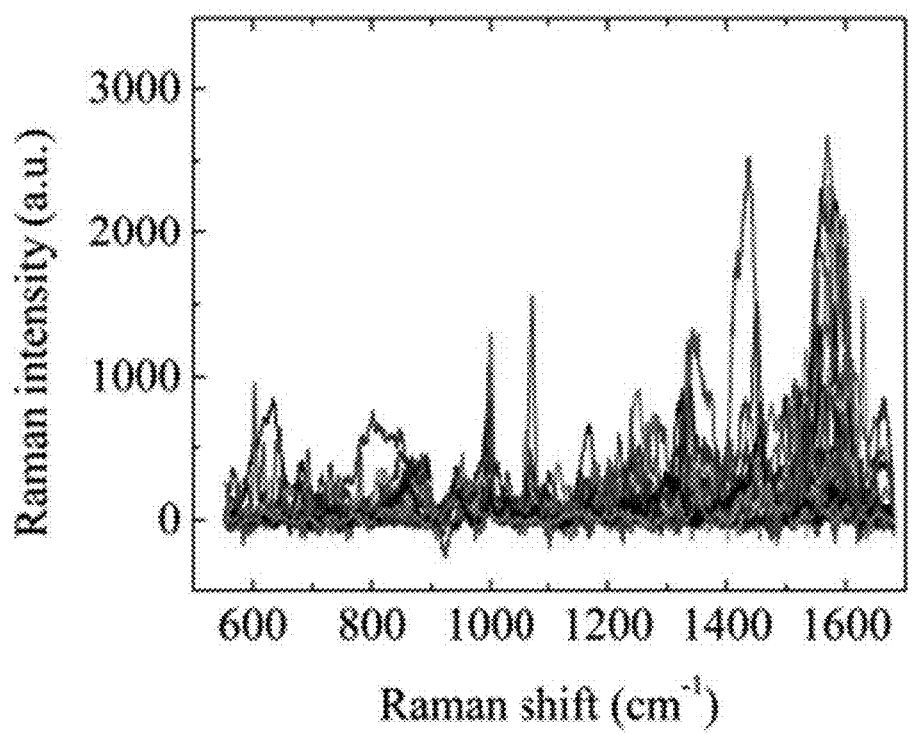
FIG. 9H illustrates Raman spectra of EVs isolated from FBS using an ExoQuick kit.

FIGS. 19A-9D are averaged Raman spectra of exosomes from four different origin: two healthy individual FIG. 9A & FIG. 9B, lung cancer cell line HCC827 (FIG. 9C) and lung cancer cell line H1975 (FIG. 9D). FIG. 9E shows the PCA result with lung cancer cells being clearly distinguishable though healthy cells from individuals are indistinguishable.

The results clearly show that the exosomes from the four different sources: serum of healthy individuals (FIG. 16A, B), and cell lines HCC827 (FIG. 16C) and H1975 (FIG. 16D) clustered into distinguishable groups with <5% overlap between the different groups on average at a sensitivity of >84%. The Raman spectra of exosomes from two healthy individuals largely overlapped, indicating that they shared many common features. These findings suggest that CMAP analysis of exosomes from different bodily fluids has the potential of becoming a disease biomarker without the need of biological labels.

Figure 20A:
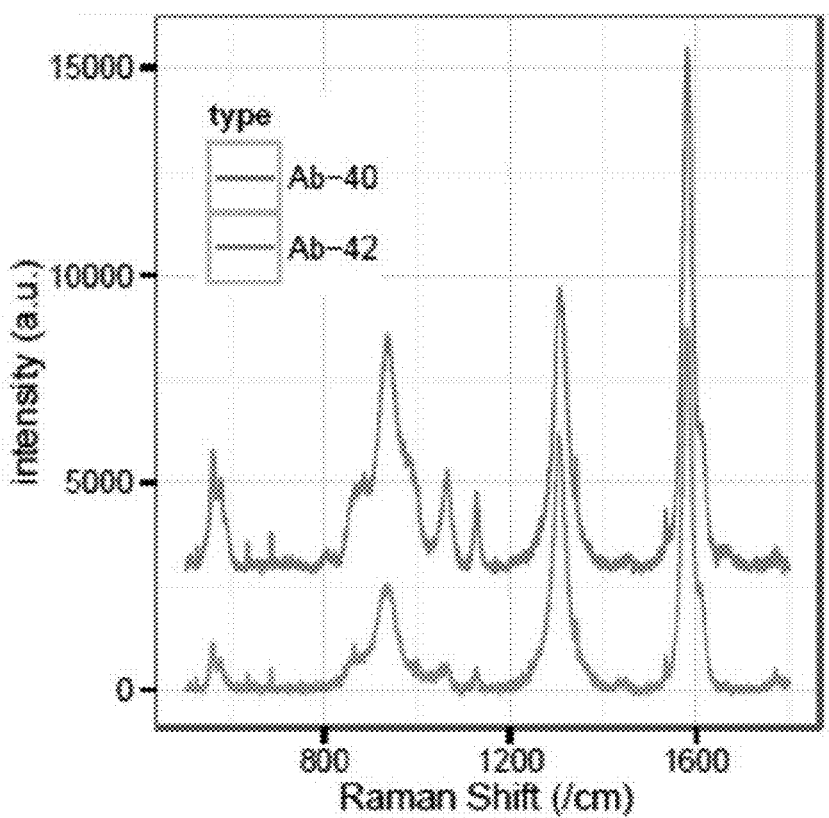
FIG. 20A illustrates the Raman spectra of amyloid-β-40 and amyloid-β-42 peptides (fragments of proteins)
Figure 20B:
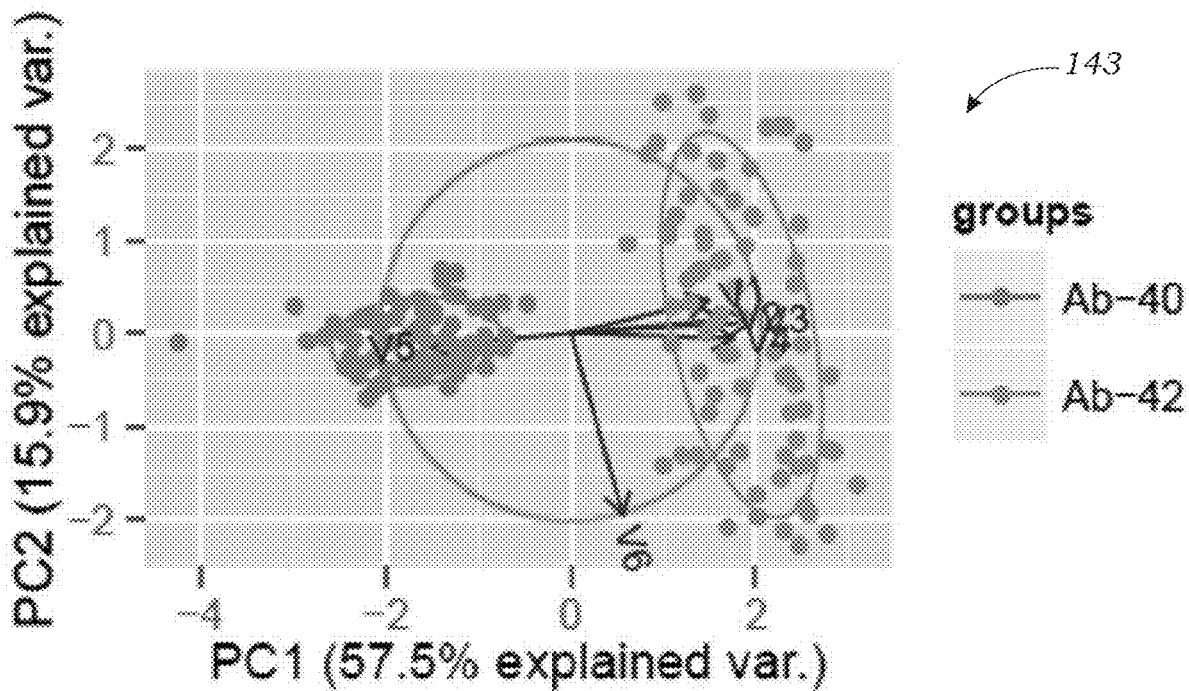
FIG. 20B shows the PCA results showing clear distinctive grouping.

FIG. 20A illustrates the Raman spectra of amyloid-β-40 and amyloid-β-42 peptides (fragments of proteins). Amyloid β-protein (Aβ) assembly into neurotoxic structures appears to be a seminal pathogenetic event in Alzheimer's disease (AD). These peptides are 40 and 42 amino acids long, respectively. Peptides were synthesized using an automated peptide synthesizer using the methods described in Walsh et al., Amyloid β-protein fibrillogenesis. Detection of a protofibrillar intermediate, J Biol Chem 272, 22364-22372 (1997).

Immediately following solubilization, 20 μL aliquots of Aβ40 or Aβ42 were applied to a graphene-coated, pyramidal gold hybrid platform and dried in vacuo. Spectra were acquired using a Renishaw inVia microscope under ambient conditions. The excitation wavelength was 785 nm and the He—Ne laser power was 0.5 mW. The 785 nm laser was chosen due to the relatively lower photon energy of excitation, which avoids thermal degradation of biomaterials. The grating used was 1800 lines/mm, and the objective lens used was 50×. We scanned the entire region on the platform occupied by the samples (≈24 μm×≈30 μm) using Raman mapping with a step size of 3 μm (i.e., independent areas of 9 μm² each). Raman data were analyzed using Renishaw WiRE 4.2 software, which provided the means to subtract the baseline signal and to remove noise. Peak intensities in each spectrum were normalized to the graphene G peak to enable spectral comparisons among samples. The fact that the mere 2 amino acids difference can be clearly distinguished once again stands witness of the power of using CMAP as biomarkers. FIG. 10A shows the characteristic spectra of A-β-40 and A-β-42. FIG. 10B shows the PCA results showing clear distinctive grouping.

While embodiments of the present invention have been shown and described, various modifications may be made without departing from the scope of the present invention. The invention, therefore, should not be limited except to the following claims and their equivalents.

For example, while certain processing and system configurations have been described with reference to processing of particular biological specimen examples, embodiments may also be used for identification or characterization of biological specimens that do not contain cells, such as a bodily fluid of cerebrospinal fluid (CSF).

Additionally, while embodiments have been described with reference to particular biomolecules or components of a biological specimen (e.g., proteome), embodiments may be applied for biological specimen characterization using various or all biomolecules of a biological specimen, including DNA, RNA, lipids, glucose etc, in other words, the entire content of cells, such that data extracted and utilized by embodiments can go beyond the "proteome". Accordingly, while certain embodiments involve processing involving proteins and amino acids, it will be understood that embodiments are not so limited.

Further, various data processing and analysis algorithms may be utilized to process data generated by a spectrometer to determine whether the database includes a matching spectra. Analysis program executed by computing device may utilize one or more types of statistical analysis algorithms such as one or more of multivariate analysis, clustering algorithms, principal component analysis, machine learning methods such as linear methods, nearest neighbor methods, ensemble methods and neural networks can be applied to process the data.

For example, the complexity of biological-analyses (such as protein, exosome and cell characterization) may lead to complicated and diverse Raman spectrums, and various factors can contribute to statistical variations. For example, statistical variations may result from factors such as biological and individual variability as well as co-factors such as a patient that is suspected of cancer but also suffering from high blood pressure or diabetes. To account for and include such variations, large number (on the order of hundreds) of spectra from each sample may be collected with their spectral features categorized and subject to thorough comparison. A large volume of data processing involved can be addressed by data analysis methods. For example, in order to make all the collected spectra comparable, a reference peak may be selected as a normalization standard (e.g., for exosome specimen, a lipid peak at 1450 cm$^{-1}$; for AP sample, a 935 cm$^{-1}$ peak may be selected) to effectively reduce the influence of enhancement factor difference. As one of the methods to interpret Raman spectra is to take the intensity of each wavenumber as a dimension, each of the spectrum can be taken as a ~1500 dimension data. Dimensionality reduction can be performed for more efficient data processing. Principal component analysis (PCA) is done based on the normalized data for the purpose of data visualization and pre-processing. As an example involving Aβ and exosome, a 2-D or 3-D space PCA analysis makes it possible to group plotted data into clusters with each cluster representing an analyte type. If the analytes cannot be separated from the PCA plot (CSF, bacteria, cancer cell, etc.), machine learning methods such as linear methods, nearest neighbor methods, ensemble methods and neural networks can be applied to process the data. The performance of those methods varies over different applications because of their difference in factors such as size of dataset and analyte composition.

What is claimed is:

1. A method of identifying a disease or health state of a subject, the method comprising:
a specimen characterization system, by a spectroscopy device, subjecting a biological specimen of the subject to spectroscopic analysis, generating spectroscopic data of the biological specimen and determining data of a relative abundance of proteins or amino acids in a biological element of the biological specimen, wherein the biological element includes a cellular structure comprising an exosome; and
the specimen characterization system, by a computing system, receiving the relative abundance data from the spectroscopy device and executing a subject analysis program that accesses a database of previously stored relative abundance data, executes a comparison of the relative abundance data of the biological specimen against previously stored relative abundance data of known specimens contained within the database, and automatically identifies a disease or health state of the subject based at least in part upon the comparison.

2. The method of claim 1, wherein the biological specimen comprises cells.

3. The method of claim 1, the spectroscopic analysis comprising scanning an x, y surface of the biological specimen by a first, coarse scan of the biological specimen and a second, fine scan of the biological specimen.

4. The method of claim 3, wherein the first, coarse scan utilizes a pixel size of about 1 micrometer and a first scan area of about 20 square micrometers, and the second, fine scan utilizes a pixel size of about 0.1 micrometers and a second scan area of about two square micrometers.

5. The method of claim 1, wherein the biological specimen comprises a biological fluid obtained from the subject.

6. The method of claim 5, wherein the bodily fluid is blood, sweat, urine, cerebrospinal fluid, saliva, semen or pleural fluid.

7. The method of claim 1, the spectroscopy device subjecting the biological specimen to spectroscopic analysis comprising Raman spectroscopy analysis, Surface Enhanced Raman Spectroscopy (SERS) analysis, mass spectrometry analysis or Fourier Transform Infrared (FTIR) spectroscopy.

8. The method of claim 1, the database comprising previously stored relative abundance data previously generated by respective types of spectroscopic analyses of known specimens.

9. The method of claim 1, the biological specimen comprising a dried biological specimen.

10. The method of claim 1, the biological specimen comprising a wet biological specimen.

11. The method of claim 1, further comprising the subject analysis program outputting the identified disease or health state to a display of the computing system for presentation of the identified disease or health state to a user of the computing system.

12. The method of claim 1, wherein the identified disease or health state is a bacterial infection, cancer or Alzheimer's disease.

13. The method of claim 1, wherein the biological specimen is a label-free biological specimen.

14. The method of claim 1, wherein the computing system receives the relative abundance data through a network from the spectroscopy device and is located remotely relative to the spectroscopy device, and the subject analysis program is executed remotely relative to the spectroscopy device.

15. The method of claim 1, wherein the disease or health state is identified by the computing system performing multivariate analysis on the relative abundance data received from the spectroscopy device.

16. The method of claim 1, wherein the disease or health state is identified by the computing system performing machine learning analysis.

17. A method of characterizing a biological specimen obtained from a subject, the method comprising:
- a specimen characterization system, by a spectroscopy device, subjecting a plasmonic substrate containing a biological specimen including one or more unlabeled cells to spectroscopic analysis, wherein the plasmonic substrate comprises a plurality of plasmonic nanofeatures disposed on a surface of the plasmonic substrate, a van der Waals (vdW) material is disposed on the plasmonic substrate and over the plasmonic nanofeatures, and the biological specimen is loaded atop the vdW material and onto the plasmonic substrate;
- the specimen characterization system, by the spectroscopy device, collecting vibrational spectra data of the one or more unlabeled cells located on or adjacent to the plasmonic substrate; and
- the specimen characterization system, by a computing system, receiving the vibrational spectra data from the spectroscopy device and a display for displaying information regarding the specimen; and
- the specimen characterization system, by a software analysis program executed by the computing system, accessing a database of previously stored vibrational spectra data, executing a comparison of the collected vibrational spectra data and the previously stored vibrational spectra data in the database, and automatically identifying the cell type of the one or more unlabeled cells in the biological specimen based at least in part upon the comparison and further outputting cellular proteome information for the one or more unlabeled cells to the display for presentation of an identified disease or health state of the subject corresponding to the cellular proteome information.

18. The method of claim 17, the cell type comprising a cell phenotype.

19. The method of claim 17, the cellular proteome information comprising cellular health information.

20. The method of claim 17, the cell type comprising a cancer cell type, a bacteria type, a fungus type, an extracellular vesicle (EV) type, or an exosome type.

21. The method of claim 17, the cell type comprising a type of circulating tumor cell (CTC).

22. The method of claim 17, the database of previously stored vibrational spectra data comprising a plurality of records, each record comprising a cell type label.

23. The method of claim 17, the biological specimen comprising a whole blood specimen.

24. The method of claim 17, wherein the identified cell type is a bacteria cell, a cancer cell or a diseased cell.

* * * * *